(12) United States Patent
Fung

(10) Patent No.: US 11,662,818 B2
(45) Date of Patent: May 30, 2023

(54) SYSTEM AND METHOD FOR EVALUATION, DETECTION, CONDITIONING, AND TREATMENT OF NEUROLOGICAL FUNCTIONING AND CONDITIONS

(71) Applicant: Blue Goji LLC, Austin, TX (US)

(72) Inventor: Coleman Fung, Spicewood, TX (US)

(73) Assignee: BLUE GOJI LLC., Austin, TX (US)

( * ) Notice: Subject to any disclaimer, the term of this patent is extended or adjusted under 35 U.S.C. 154(b) by 84 days.

(21) Appl. No.: 17/030,233

(22) Filed: Sep. 23, 2020

(65) Prior Publication Data

US 2021/0001171 A1 Jan. 7, 2021

Related U.S. Application Data

(63) Continuation-in-part of application No. 17/030,195, filed on Sep. 23, 2020, and a continuation-in-part of
(Continued)

(51) Int. Cl.
*G06F 3/01* (2006.01)
*G06T 19/00* (2011.01)
(Continued)

(52) U.S. Cl.
CPC .............. *G06F 3/015* (2013.01); *A61B 5/165* (2013.01); *A61B 5/4082* (2013.01);
(Continued)

(58) Field of Classification Search
CPC .......... G06F 3/015; G06F 1/163; G06F 3/011; G06F 3/016; A63F 13/214; A63F 13/40;
(Continued)

(56) References Cited

U.S. PATENT DOCUMENTS

| 9,084,565 B2 | 7/2015 | Mason et al. |
| 10,380,910 B2 | 8/2019 | Wu et al. |

(Continued)

FOREIGN PATENT DOCUMENTS

| BY | 20070529 | 10/2009 |
| WO | 9527439 A1 | 10/1995 |

(Continued)

*Primary Examiner* — Phong H Dang
(74) *Attorney, Agent, or Firm* — Galvin Patent Law LLC; Brian R. Galvin

(57) ABSTRACT

A system and method for evaluation, detection, conditioning, and treatment of neurological functioning and conditions which uses data obtained while a person is engaged in simultaneously in a range of primary physical tasks combined with defined types of associative activity, such as listening, reading, speaking, mathematics, logic puzzles, navigation of a virtual environment, recall of past stimuli, etc. The data from the physical and associative activities are combined to generate a composite functioning score visualization indicating the relative functioning of areas aspects of neurological functioning; including those in which deficiencies may be present, which are early indicators of possible neurological conditions. Through algorithmic recommendations combined with expert and user input, a conditioning regimen targeting neurological aspects of interest paired with periodic testing allows the user to track their progress in these areas over time.

10 Claims, 32 Drawing Sheets

Related U.S. Application Data application No. 16/927,704, filed on Jul. 13, 2020, now abandoned, which is a continuation of application No. 16/867,238, filed on May 5, 2020, now abandoned, which is a continuation-in-part of application No. 16/793,915, filed on Feb. 18, 2020, now abandoned, said application No. 17/030,195 is a continuation-in-part of application No. 16/781,663, filed on Feb. 4, 2020, now Pat. No. 11,191,996, which is a continuation-in-part of application No. 16/354,374, filed on Mar. 15, 2019, now Pat. No. 10,549,153, said application No. 16/793,915 is a continuation-in-part of application No. 16/255,641, filed on Jan. 23, 2019, now Pat. No. 10,561,900, which is a continuation of application No. 16/223,034, filed on Jan. 23, 2019, now Pat. No. 10,688,341, said application No. 16/354,374 is a continuation-in-part of application No. 16/176,511, filed on Oct. 31, 2018, now Pat. No. 10,960,264, said application No. 16/223,034 is a continuation-in-part of application No. 16/176,511, filed on Oct. 31, 2018, now Pat. No. 10,960,264, which is a continuation-in-part of application No. 15/853,746, filed on Dec. 23, 2017, now Pat. No. 10,265,578, which is a continuation of application No. 15/219,115, filed on Jul. 25, 2016, now Pat. No. 9,849,333, which is a continuation-in-part of application No. 15/193,112, filed on Jun. 27, 2016, now abandoned, which is a continuation-in-part of application No. 15/187,787, filed on Jun. 21, 2016, now Pat. No. 10,124,255, which is a continuation-in-part of application No. 15/175,043, filed on Jun. 7, 2016, now Pat. No. 9,766,696, said application No. 15/187,787 is a continuation-in-part of application No. 14/846,966, filed on Sep. 7, 2015, now Pat. No. 10,080,958, and a continuation-in-part of application No. 14/012,879, filed on Aug. 28, 2013, now Pat. No. 10,737,175.

(60) Provisional application No. 62/697,973, filed on Jul. 13, 2018, provisional application No. 62/330,602, filed on May 2, 2016, provisional application No. 62/330,642, filed on May 2, 2016, provisional application No. 62/310,568, filed on Mar. 18, 2016, provisional application No. 61/696,068, filed on Aug. 31, 2012.

(51) Int. Cl.

| | | |
|---|---|---|
| *A63B 23/04* | (2006.01) | |
| *A63B 22/00* | (2006.01) | |
| *A63B 22/02* | (2006.01) | |
| *A63F 13/65* | (2014.01) | |
| *A63F 13/40* | (2014.01) | |
| *A63B 22/06* | (2006.01) | |
| *A63F 13/214* | (2014.01) | |
| *A63F 13/212* | (2014.01) | |
| *G06F 1/16* | (2006.01) | |
| *A61B 5/00* | (2006.01) | |
| *A61B 5/16* | (2006.01) | |
| *A63B 24/00* | (2006.01) | |
| *H04W 84/18* | (2009.01) | |
| *G06F 3/03* | (2006.01) | |
| *A61B 5/11* | (2006.01) | |

(52) U.S. Cl.
CPC .......... *A61B 5/4088* (2013.01); *A61B 5/4842* (2013.01); *A63B 22/0046* (2013.01); *A63B 22/0285* (2013.01); *A63B 22/0292* (2015.10); *A63B 22/06* (2013.01); *A63B 23/04* (2013.01); *A63F 13/212* (2014.09); *A63F 13/214* (2014.09); *A63F 13/40* (2014.09); *A63F 13/65* (2014.09); *G06F 1/163* (2013.01); *G06F 3/011* (2013.01); *G06F 3/016* (2013.01); *G06T 19/006* (2013.01); *A61B 5/1124* (2013.01); *A63B 24/0003* (2013.01); *G06F 3/0304* (2013.01); *G06F 2203/012* (2013.01); *H04W 84/18* (2013.01)

(58) Field of Classification Search
CPC . A63F 13/65; A63B 22/0292; A63B 22/0046; A63B 22/0285; A63B 22/06; A63B 23/04; A61B 5/165; A61B 5/4082; A61B 5/4088; A61B 5/4842; G06T 19/006
See application file for complete search history.

(56) References Cited

U.S. PATENT DOCUMENTS

| | | | |
|---|---|---|---|
| 2004/0153129 A1 | 8/2004 | Pless et al. | |
| 2005/0092183 A1 | 5/2005 | Koslow et al. | |
| 2007/0191727 A1* | 8/2007 | Fadem | A61B 5/378 600/544 |
| 2012/0068820 A1* | 3/2012 | Mollicone | H04L 63/0861 340/5.82 |
| 2014/0276130 A1* | 9/2014 | Mirelman | A61B 5/112 600/595 |
| 2014/0370479 A1* | 12/2014 | Gazzaley | A61B 5/162 434/322 |
| 2015/0038803 A1* | 2/2015 | Uhlig | A61B 5/4023 600/301 |
| 2015/0079578 A1 | 3/2015 | Nardi | |
| 2017/0270818 A1* | 9/2017 | French | G09B 5/02 |
| 2018/0078184 A1* | 3/2018 | Yagi | A61B 5/1128 |
| 2020/0135324 A1* | 4/2020 | Roy | G16H 20/30 |
| 2020/0135325 A1* | 4/2020 | Gavas | A61B 5/162 |

FOREIGN PATENT DOCUMENTS

| | | |
|---|---|---|
| WO | 2004044994 A9 | 7/2004 |
| WO | 2005092183 A1 | 10/2005 |

* cited by examiner

SYSTEM AND METHOD FOR EVALUATION, DETECTION, CONDITIONING, AND TREATMENT OF NEUROLOGICAL FUNCTIONING AND CONDITIONS

CROSS-REFERENCE TO RELATED APPLICATIONS

| Application No. | Date Filed | Title |
|---|---|---|
| Current application | Herewith | A SYSTEM AND METHOD FOR RANGE OF MOTION ANALYSIS AND BALANCE TRAINING WHILE EXERCISING |
| | | Is a continuation-in-part of: |
| 16/927,704 | Jul. 13, 2020 | SYSTEM AND METHOD FOR RANGE OF MOTION ANALYSIS AND BALANCE TRAINING WHILE EXERCISING |
| | | which is a continuation-in-part of: |
| 16/867,238 | May 5, 2020 | SYSTEM AND METHOD FOR RANGE OF MOTION ANALYSIS AND BALANCE TRAINING WHILE EXERCISING |
| | | which is a continuation of: |
| 16/793,915 | Feb. 18, 2020 | SYSTEM AND METHOD FOR RANGE OF MOTION ANALYSIS AND BALANCE TRAINING WHILE EXERCISING |
| | | which is a continuation-in-part of: |
| 16/255,641 U.S. Pat. No. 10,561,900 | Jan. 23, 2019 Issue Date Feb. 18, 2020 | SYSTEM AND METHOD FOR RANGE OF MOTION ANALYSIS AND BALANCE TRAINING WHILE EXERCISING |
| | | which is a continuation of: |
| 16/223,034 U.S. Pat. No. 10,688,341 | Jan. 23, 2019 Issue Date Jun. 23, 2020 | SYSTEM AND METHOD FOR RANGE OF MOTION ANALYSIS AND BALANCE TRAINING WHILE EXERCISING |
| | | which claims benefit of and priority to: |
| 62/697,973 | Jul. 13, 2018 | VARIABLE-RESISTANCE EXERCISE MACHINE WITH WIRELESS COMMUNICATION FOR SMART DEVICE CONTROL AND INTERACTIVE SOFTWARE APPLICATIONS |
| | | and is also a continuation-in-part of: |
| 16/176,511 | Oct. 31, 2018 | VIRTUAL REALITY AND MIXED REALITY ENHANCED EXERCISE MACHINE |
| | | which is a continuation-in-part of: |
| 16/011,394 U.S. Pat. No. 10,155,133 | Jun. 18, 2018 Issue Date Dec. 18, 2018 | SYSTEM AND METHOD FOR A MIXED OR VIRTUAL REALITY-ENHANCED STATIONARY EXERCISE BICYCLE |
| | | which is a continuation-in-part pf: |
| 15/853,746 U.S. Pat. No. 10,265,578 | Dec. 23, 2017 Issue Date Apr. 23, 2019 | VARIABLE-RESISTANCE EXERCISE MACHINE WITH WIRELESS COMMUNICATION FOR SMART DEVICE CONTROL AND INTERACTIVE SOFTWARE APPLICATIONS |
| | | which is a continuation of: |
| 15/219,115 U.S. Pat. No. 9,849,333 | Jul. 25, 2016 Issue Date Dec. 26, 2017 | VARIABLE-RESISTANCE EXERCISE MACHINE WITH WIRELESS COMMUNICATION FOR SMART DEVICE CONTROL AND VIRTUAL REALITY APPLICATIONS |
| | | which claims benefit of and priority to: |
| 62/330,642 | May 2, 2016 | VARIABLE-RESISTANCE EXERCISE MACHINE WITH WIRELESS COMMUNICATION FOR SMART DEVICE CONTROL AND VIRTUAL REALITY APPLICATIONS |
| | | and is also a continuation of: |
| 15/193,112 | Jun. 27, 2016 | NATURAL BODY INTERACTION FOR MIXED OR VIRTUAL REALITY APPLICATIONS |
| | | which claims benefit of and priority to: |
| 62/330,602 | May 2, 2016 | NATURAL BODY INTERACTION FOR MIXED OR VIRTUAL REALITY APPLICATIONS |
| | | and is also a continuation-in-part of: |
| 15/187,787 U.S. Pat. No. 10,124,255 | Jun. 21, 2016 Issue Date Nov. 13, 2018 | MULTIPLE ELECTRONIC CONTROL AND TRACKING DEVICES FOR MIXED-REALITY INTERACTION |
| | | which is a continuation-in-part of: |
| 15/175,043 U.S. Pat. No. | Jun. 7, 2016 Issue Date | APPARATUS FOR NATURAL TORSO TRACKING AND FEEDBACK FOR |

-continued

| Application No. | Date Filed | Title |
| --- | --- | --- |
| 9,766,696 | Sep. 19, 2017 | ELECTRONIC INTERACTION |
| | | which claims benefit of and priority to: |
| 62/310,568 | Mar. 18, 2016 | APPARATUS FOR NATURAL TORSO TRACKING AND FEEDBACK FOR ELECTRONIC INTERACTION |
| Current application | Herewith | A SYSTEM AND METHOD FOR RANGE OF MOTION ANALYSIS AND BALANCE TRAINING WHILE EXERCISING |
| | | Is a continuation-in-part of: |
| 17/030,195 | Sep. 23, 2020 | APPARATUS FOR NATURAL TORSO AND LIMBS TRACKING AND FEEDBACK FOR ELECTRONIC INTERACTION |
| | | which is a continuation-in-part of: |
| 16/781,663 | Feb. 4, 2020 | BODY JOYSTICK FOR INTERACTING WITH VIRTUAL REALITY OR MIXED REALITY MACHINES OR SOFTWARE APPLICATIONS |
| | | which is a continuation in-part-of: |
| 16/354,374 | Mar. 15, 2019 | VIRTUAL REALITY AND MIXED REALITY ENHANCED ELLIPTICAL EXERCISE TRAINER |
| | | which is a continuation-in-part of: |
| 16/176,511 | Oct. 31, 2018 | VIRTUAL REALITY AND MIXED REALITY ENHANCED EXERCISE MACHINE |
| | | which is a continuation-in-part of: |
| 16/011,394 U.S. Pat. No. 10,155,133 | Jun. 18, 2018 Issue Date Dec. 18, 2018 | SYSTEM AND METHOD FOR A MIXED OR VIRTUAL REALITY-ENHANCED STATIONARY EXERCISE BICYCLE |
| | | which is a continuation-in-part pf: |
| 15/853,746 U.S. Pat. No. 10,265,578 | Dec. 23, 2017 Issue Date Apr. 23, 2019 | VARIABLE-RESISTANCE EXERCISE MACHINE WITH WIRELESS COMMUNICATION FOR SMART DEVICE CONTROL AND INTERACTIVE SOFTWARE APPLICATIONS |
| | | which is a continuation of: |
| 15/219,115 U.S. Pat. No. 9,849,333 | Jul. 25, 2016 Issue Date Dec. 26, 2017 | VARIABLE-RESISTANCE EXERCISE MACHINE WITH WIRELESS COMMUNICATION FOR SMART DEVICE CONTROL AND VIRTUAL REALITY APPLICATIONS |
| | | which is a continuation of: |
| 15/193,112 | Jun. 27, 2016 | NATURAL BODY INTERACTION FOR MIXED OR VIRTUAL REALITY APPLICATIONS |
| | | which is a continuation-in-part of: |
| 15/187,787 U.S. Pat. No. 10,124,255 | Jun. 21, 2016 Issue Date Nov. 13, 2018 | MULTIPLE ELECTRONIC CONTROL AND TRACKING DEVICES FOR MIXED-REALITY INTERACTION |
| | | which is a continuation-in-part of: |
| 14/846,966 U.S. Pat. No. 10,080,958 | Sep. 7, 2015 Issue Date Sep. 25, 2018 | MULTIPLE ELECTRONIC CONTROL DEVICES |
| | | and is also a continuation-in-part of: |
| 14/012,879 U.S. Pat. No. 10,737,175 | Aug. 28, 2013 Issue Date Aug. 11, 2020 | Mobile and Adaptable Fitness System |
| | | which claims benefit of and priority to: |
| 61/696,068 | Aug. 31, 2012 | Mobile and Adaptable Fitness System | the entire specification of each of which is incorporated herein by reference.

BACKGROUND OF THE INVENTION

Field of the Art

The disclosure relates to the field of health devices, and more particularly to devices and methods for evaluation, detection, conditioning, and treatment of neurological functioning and conditions.

Discussion of the State of the Art

Research increasingly highlights the importance of continued neurological stimulation throughout all stages of life including physical activity, social connection, and frequent cognitive challenge, especially when combined, in preventing early cognitive decline and onset of neurological disorders including Dementia. As well, athletes and competitors in various fields such as physical, digital, and cognitive competitions are increasingly seeking well rounded methods of neurological evaluation and conditioning for tasks directly and indirectly related to their mode of competition. Many games and tools exist to train specific aspects of competition or neurological function or improve physical activity while gaming, but none integrate a virtual environment with combined biometric and neurological performance data to evaluate, condition, and track progress in multiple aspects of neurological functioning.

What is needed is a system and method for evaluation and conditioning relative neurological functioning which uses simultaneous engagement in primary physical tasks and associative activities as an evaluation, conditioning, and performance tracking tool.

SUMMARY OF THE INVENTION

Accordingly, the inventor has conceived and reduced to practice, a system and method for evaluation, detection, conditioning, and treatment of neurological functioning and conditions which uses data obtained while a person is engaged simultaneously in a primary physical task and an associative activity. The system and method involve having a subject engage in defined types of physical activity, wherein data is gathered concerning indicators of physical function such as posture, balance, gait symmetry and stability, and consistency and strength of repetitive motion (e.g., walking or running pace and consistency, cycling cadence and consistency, etc.). Simultaneously, the person is asked to engage in a range of associative activities that will each stimulate a specific neurological function or region and collectively cover a comprehensive range of aspects of the nervous system. These associative activities include mental, other physical activities, as well as emotional experiences such as listening, reading, speaking, fine and gross motor movements, mathematics, logic puzzles, executive decisions, navigation, short- and longer-term memory challenges, empathic and traumatic scenarios, etc. The biometric and performance data from the primary physical tasks and the performance on associative activities are combined to generate a composite functioning score map indicating the relative performance on the primary physical tasks and the associative areas, which can then be analyzed and compared against the population averages (from a larger population dataset) and benchmarks fora relative neurological functioning profile and identify potential deficits and conditions.

According to a preferred embodiment, a system for detection of neurological functioning and conditions is disclose, comprising: a physical activity data capture device, configured to capture movement and other biometric data of an individual during performance of a primary task; a software application, comprising a first plurality of programming instructions stored in a memory of, and operating on a processor of, a computing device, wherein the first plurality of programming instructions, when operating on the processor, cause the computing device to: assign a primary task to an individual under assessment; while the individual engages in the primary task, record performance data on the primary activity and biometric data of the individual, using the physical activity data capture device; assign an associative activity to the individual which corresponds to a specific neurological function or region; while the individual engages in the associative activity, record performance data of the individual on the associative activity; assign a dual task to the individual, the dual task comprising simultaneous performance of the primary task and the associative activity; while the individual engages in the dual task, record performance data and biometric data of the individual while performing the primary task, using the physical activity data capture device, and record performance data of the individual on the associative activity; and send the recorded data to a neurological functioning analyzer; and a neurological functioning analyzer, comprising a second plurality of programming instructions stored in the memory of, and operating on the processor of, the computing device, wherein the second plurality of programming instructions, when operating on the processor, cause the computing device to: receive the recorded data; calculate a composite functioning score for the recorded data, the composite functioning score comprising an indication of the level of functionality of an aspect of the individuals' nervous system; and generate a neurological condition profile of the individual comprising an indication of relative functioning of the aspect of the individual's nervous system.

According to another preferred embodiment, a method for detection of neurological functioning and conditions is disclosed, comprising the steps of: assigning a primary task to an individual under assessment; while the individual engages in the primary task, recording performance data on the primary activity and biometric data of the individual, using the physical activity data capture device; assigning an associative activity to the individual which corresponds to a specific neurological function or region; while the individual engages in the associative activity, recording performance data of the individual on the associative activity; assigning a dual task to the individual, the dual task comprising simultaneous performance of the primary task and the associative activity; while the individual engages in the dual task, recording performance data and biometric data of the individual while performing the primary task, using the physical activity data capture device, and recording performance data of the individual on the associative activity; and calculating a composite functioning score for the recorded data, the composite functioning score comprising an indication of the level of functionality of an aspect of the individuals' nervous system; and generating a neurological condition profile of the individual comprising an indication of relative functioning of the aspect of the individual's nervous system.

According to an aspect of an embodiment, one or more primary tasks and one or more associative activities are assigned to the individual, a plurality of composite functioning scores are calculated comprising indications of the level of functionality of a plurality of aspects of the individuals' nervous system, and the neurological functioning profile comprises indications of relative functioning of the plurality of aspects of the individual's nervous system. According to an aspect of an embodiment, a neurological functioning analyzer is used to create a composite functioning score spatial map based on the neurological functioning profile.

According to an aspect of an embodiment, the composite functioning score is compared to a history of composite functioning scores for the individual to determine changes in the composite functioning score over time.

According to an aspect of an embodiment, the composite functioning score is compared to statistical composite functioning score data for a larger population to determine the individual's relative position in the larger population with respect to the composite functioning score.

According to an aspect of an embodiment, the primary task is continuous exercise.

According to an aspect of an embodiment, the primary task is discontinuous, interval-based, or variable effort exercise.

According to an aspect of an embodiment, the associative activity involves overcoming a computer or video game-like challenge or a computer simulation of a life-like scenario or challenge.

According to an aspect of an embodiment, the recorded data is stored as a historical record of the individual's performance on primary tasks, associative activities, and dual tasks.

According to an aspect of an embodiment, the neurological condition profile is used to select the primary task and associative task to improve the individual's performance over time.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

DETAILED DESCRIPTION

Figure 1:
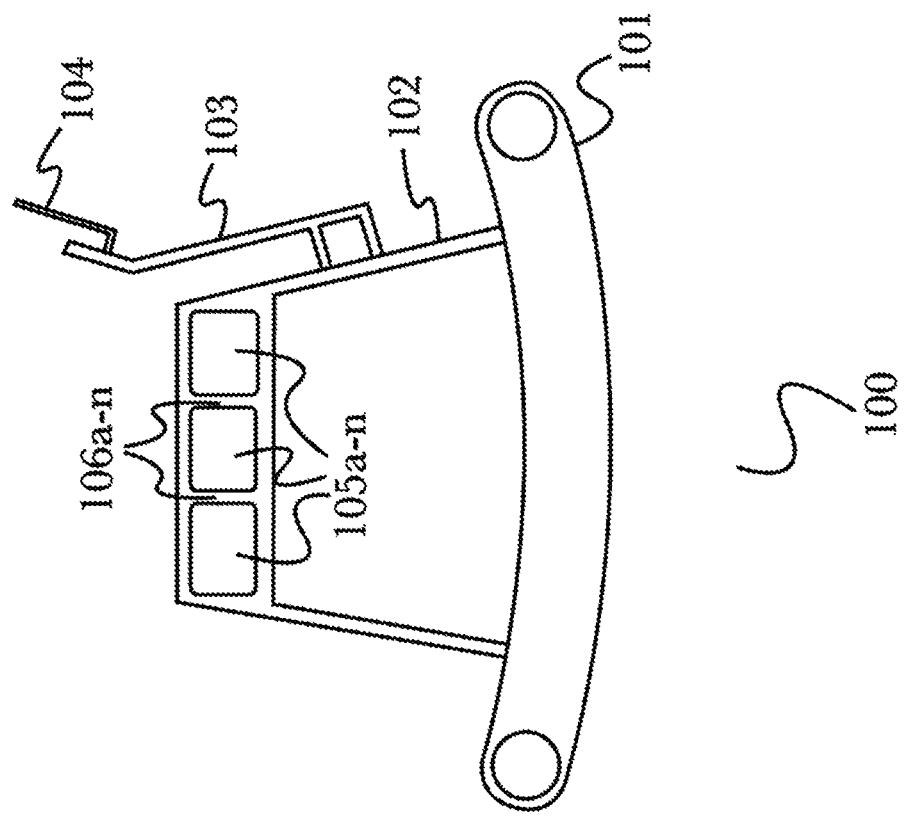
FIG. 1 is a side view of an exemplary variable-resistance exercise machine with an embedded or a wireless computing device controlling the interactive software applications of the invention.

The inventor has conceived, and reduced to practice, a system and method for evaluation, detection, conditioning, and treatment of neurological functioning and conditions which uses data obtained while a person is engaged in simultaneously in a primary physical task and an associative activity. The system and method involve having a subject engage in a primary physical task, wherein movement data is gathered concerning indicators of physical function such as posture, balance, gait symmetry and stability, and consistency and strength of repetitive motion (e.g., walking or running pace and consistency, cycling cadence and consistency, etc.) along with other biometric data (eg., heart rate, heart rate variability, galvanic skin response, pupil dilation, facial expression, electroencephalogram, etc). Simultaneously, the person is asked to engage in a range of associative activities that will each stimulate a specific neurological function or region and collectively cover all aspects of the nervous system. These associative activities include mental activities, other physical activities, as well as emotional experiences, such as listening, reading, speaking, fine and gross motor movements, mathematics, logic puzzles, executive decisions, navigation, short- and longer-term memory challenges, empathic and traumatic scenarios, etc. The biometric and performance data from the primary physical task and the associative activities are combined to generate a composite functioning score visualization indicating the relative functioning of primary physical tasks and the associative neurological functions and, which can then be analyzed and compared against the population averages (from a larger population dataset) and benchmarks. In addition to seeing the calculated composite function score, in some cases experts and users may be given discretionary access to all or aspects of the underlying data used in computing the score.

As lifespans have improved in the past few decades, particularly in more developed countries, the mean and median age of populations have increased. The greatest risk factor for neurodegenerative diseases is aging, so older persons are more likely to suffer from degenerative diseases and conditions affecting the nervous system such as amyotrophic lateral sclerosis, Parkinson's disease, Alzheimer's disease, fatal familial insomnia, Huntington's disease, Friedreich's ataxia, Lewy body disease, and spinal muscular atrophy. It has been estimated that some 20-40% of healthy people between 60 and 78 years old experience discernable decrements in cognitive performance in one or more areas including working, spatial, and episodic memory, and cognitive speed. Early stages of neurodegenerative diseases are difficult to detect, the causes of such diseases are not well understood, and treatments for such diseases are non-existent.

Without using one of the costly brain scan technologies, it remains difficult to detect, assess, and treat poor functioning of the nervous system, whether such poor functioning is due to injury to the brain, neurodegenerative disease, psychological or physical trauma, or changes in brain chemistry, diet, stress, substance abuse, or other factors. For certain neurological conditions, such as Chronic Traumatic Encephalopathy (CTE), none of the current brain scan technologies are able to reliably capture diagnostic data. Other neurological deficits and conditions can be evaluated or diagnosed using assessments using readily available equipment and observational analysis, such as the Cognitive Performance Test (CPT) and Timed Up and Go Test (TUG) but lack the sensitivity suitable for nuanced or early deficit detection. Each of these types of poor nervous system function can impact different parts of the brain and/or nervous system in different ways. Due to the complexity of interactions in the nervous system and the brain's ability to adapt its function in many areas, it remains difficult to detect poor functioning and to identify which neurological functions and anatomical aspects and regions are impacted early enough to implement an effective treatment protocol.

However, recent research studies have demonstrated that physical activity, especially aerobic exercise, can improve neurogenesis and other neurological functions, whether related to physical brain and nervous system impairments or mental health/emotional issues. In addition, evolutionary biologists have hypothesized that early humans began their cognitive revolution when they ventured into the African savannah and started walking upright. In fact, more recent research studies on the cerebellum, an ancient part of the brain that coordinates the motor control, have discovered unexpected connections between the cerebellum and other parts of the brain. Specifically, according to a team of researchers from the University of Washington, only 20 percent of the cerebellum connections was dedicated to areas involved in physical motion, while 80 percent was connected to areas involved in functions such as abstract thinking, planning, emotion, memory and language. The cerebellum doesn't actually execute tasks like thinking, just as it doesn't directly control movement. Instead, it monitors and coordinates the brain areas that are doing the work and makes them perform better.

Therefore, simultaneous testing of primary physical tasks such as walking or running and the associative activities that include various mental, other physical activities as well as emotional experiences (commonly known as a dual task assessment), and the correlation of results therefrom can be used to evaluate specific neurological functional areas to create a profile of relative neurological functioning and see where deficiencies may be present. Therefore, changes in a person's walking gait while the person is engaged in other associative activities like solving a logic puzzle could be analyzed and compared against the normal or average dual-tasking costs of the same population group for relative functioning as well as anomalies. Such anomalies for the given brain functions or regions could be indicative of abnormal central nervous system functions. Further, the combination of the dual-tasked physical and associative activities can help identify the abnormally-performing neurological functions or even help isolate affected neurological regions. For example, a walking gait/logic puzzle dual-task activity may indicate normal functioning in a given individual, indicating that autonomous physical activity and cognition are not affected. However, in the same individual another dual task of walking and listening within a virtual reality (VR) environment may result in gait changes or a complete stop of the walk as the neurological functions required for these tasks are different from walking and logic. In this case, it may indicate that there may be injury to or degeneration of the auditory cortex of the temporal lobe, potentially informing further diagnostic procedures. As a result, a system combining numerous combinations of various dual-tasking activities, covering all neurological functions or regions, may be able to evaluate, detect, and treat neurological deficits and conditions even before they become noticeably symptomatic. For individuals for whom symptoms are already present, such a system can evaluate and track changes over time, and potentially slow down or reverse the progression of such deficits and conditions.

Using this same dual-tasking analysis, it is also possible to evaluate, detect, and treat neurological conditions and changes involving mental health and emotional issues. For example, elevated heart rate, elevated blood pressure, or chest pain during exercise that are higher than an individual's normal history for these indicators can indicate emotional stress. The addition of story-telling or emotional experiences through computer games and/or simulations (and especially when such experiences are virtual-reality experiences) can help to elicit emotional and physiological responses or lack thereof. For example, a veteran suffering from PTSD (Post-Traumatic Stress Disorder) could be trained inside such a dual-tasking VR environment so that s/he can gradually regain her/his agency by overcoming progressively challenging physical and emotional scenarios—reactivating her/his dorsolateral prefrontal cortex and lateral nucleus of thalamus with the help of these combined physical and emotional activities (likely using parallel but not war-based scenarios). As a result, the veteran could potentially extricate herself or himself from such traumatic experiences by developing her/his closure stories.

The integration of a primary physical task with an associative activity is also especially well-suited for the evaluation and conditioning of specific aspects of neurological functioning in individuals training for physical, mental, or combined forms of competition. After an initial array of primary physical challenges and associated tasks designed to evaluate specific neurological functioning areas to create a profile of relative functioning a more thorough understanding of the competitor's strengths and weaknesses in their specific mode of competition can be achieved. With the help of a conditioning recommendation algorithm, expert input, and competitor input a regimen of physical and associative tasks specifically suited to improve performance of that competitor and mode of competition can be administered at prescribed or chosen frequency. Digital challenges can further be customized for competition and competitor specificity as the conditioning recommendation algorithm analyzes the efficacy of conditioning regimens for users aiming to improve in similar neurological functions, the specific user's response to conditioning inputs over time, and expert recommendations for users with similar neurological functioning profiles and objectives.

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an embodiment with several components in communication with each other does not imply that all such components are required. To the contrary, a variety of optional components may be described to illustrate a wide variety of possible embodiments of one or more of the inventions and in order to more fully illustrate one or more aspects of the inventions. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments of one or more of the inventions need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

Definitions

The phrases "neurological functioning" and "neurological function" as used herein mean any and all aspects of neuroscience and neurology where input, output, processing, or combination thereof involve aspects of the nervous system. These include but are not limited to functional as well as anatomical aspects of cognitive, sensory, motor, emotional, and behavioral functions and experiences.

The term "expert" as used herein means an individual with specialization in an area via formal training, credentials, or advanced proficiency in a modality of interest to the user or with regard to neurological functioning. This includes but is not limited to physicians, psychiatrists, physical therapists, coaches, fitness trainers, high level athletes or competitors, and teachers.

The term "conditioning" as used herein means all aspects of the system that can be used for the improvement, training, treatment of or exposure to aspects of neurological functioning. This could be in the form of a prescribed regimen from an expert, recommendation algorithm, self-selected experiences, or combination thereof.

The phrase "composite function score" as used herein means a indicative of a relative level of neurological functioning comprised of weighted input of combined movement, biometric, and performance data sources collected by a given embodiment of the system, input by the user or an expert, historical performance and life history data from various sources, etc.

The phrase "dual task assessment" as used herein means measurement of baseline performance on a set of tasks and/or activities performed individually, as well as performance of the same set of tasks and/or activities simultaneously. While this is typically a single primary task (usually motor) combined with a single associative activity (typically a neurological activity such as cognitive task), it should be taken herein to include other combinations of multiplexed tasks in combinations including, but not limited to, combinations in excess of two tasks and combinations that target a single or multiple aspects of neurological functioning.

The phrase "dual task cost" as used herein means any method for quantifying the difference in performance of a dual task assessment between the set of tasks performed individually and the same set of tasks performed simultaneously. Typically includes a comparison of each task performed in isolation to the performance on each of those tasks when performed simultaneously, either for a pair or larger combination of tasks.

The term "biometrics" as used herein mean data that can be input, directly measured, or computed using directly measured data from a user. This data includes but is not limited to physical and virtual movement, physiological, biological, behavioral, navigational, cognitive, alertness and attention, emotional, and brainwave measurements and patterns.

The phrase "primary task" as used herein means a first task or activity to be engaged in by an individual under assessment. The primary task will often, but not always, be a physical task or exercise such as walking on a treadmill.

The phrase "associative activity" as used herein means a second task or activity to be engaged in by an individual under assessment. The associative activity will often, but not always, be a mental or cognitive task such as performing arithmetic or identifying objects on a display.

Conceptual Architecture

FIG. 1 is a side view of a variable-resistance exercise machine with wireless communication for smart device control and interactive software applications 100 of the invention. According to the embodiment, an exercise machine 100 may have a stable base 101 to provide a platform for a user to safely stand or move about upon. Additional safety may be provided through the use of a plurality of integrally-formed or detachable side rails 102, for example having safety rails on the left and right sides (with respect to a user's point of view) of exercise machine 100 to provide a stable surface for a user to grasp as needed. Additionally, side rails 102 may comprise a plurality of open regions 105a-n formed to provide additional locations for a user to grasp or for the attachment of additional equipment such as a user's smart device (not shown) through the use of a mountable or clamping case or mount. Formed or removable supports 106a-n may be used for additional grip or mounting locations, for example to affix a plurality of tethers (not shown) for use in interaction with software applications while a user is using exercise machine 100 (as described below, referring to FIG. 3).

Exercise machine 100 may further comprise a rigid handlebar 103 affixed or integrally-formed on one end of exercise machine 100, for a user to hold onto while facing forward during use. Handlebar 103 may further comprise a stand or mount 104 for a user's smart device such as (for example) a smartphone or tablet computer, so they may safely support and stow the device during use while keeping it readily accessible for interaction (for example, to configure or interact with a software application they are using, or to select different applications, or to control media playback during use, or other various uses). Handlebar 103 may be used to provide a stable handle for a user to hold onto during use for safety or stability, as well as providing a rigid point for the user to "push off" during use as needed, for example to begin using a moving treadmill surface (described below in FIG. 2). During use, a user may also face away from handlebar 103, using exercise machine 100 in the reverse without their view or range of motion being obscured or obstructed by handlebar 103 (for example, for use with a virtual reality game that requires a wide degree of movement from the user's hands for interaction).

As illustrated, the base 101 of exercise machine 100 may be formed with a mild, symmetrical curvature, to better approximate the natural range of movement of a user's body during use. Common exercise machines such as treadmills generally employ a flat surface, which can be uncomfortably during prolonged or vigorous use, and may cause complications with multi-directional movement or interaction while a user's view is obscured, as with a headset (described below in FIG. 3). By incorporating a gradual curvature, a user's movements may feel more natural and require less reorientation or accommodation to become fluid and proficient, and stress to the body may be reduced.

Figure 3:
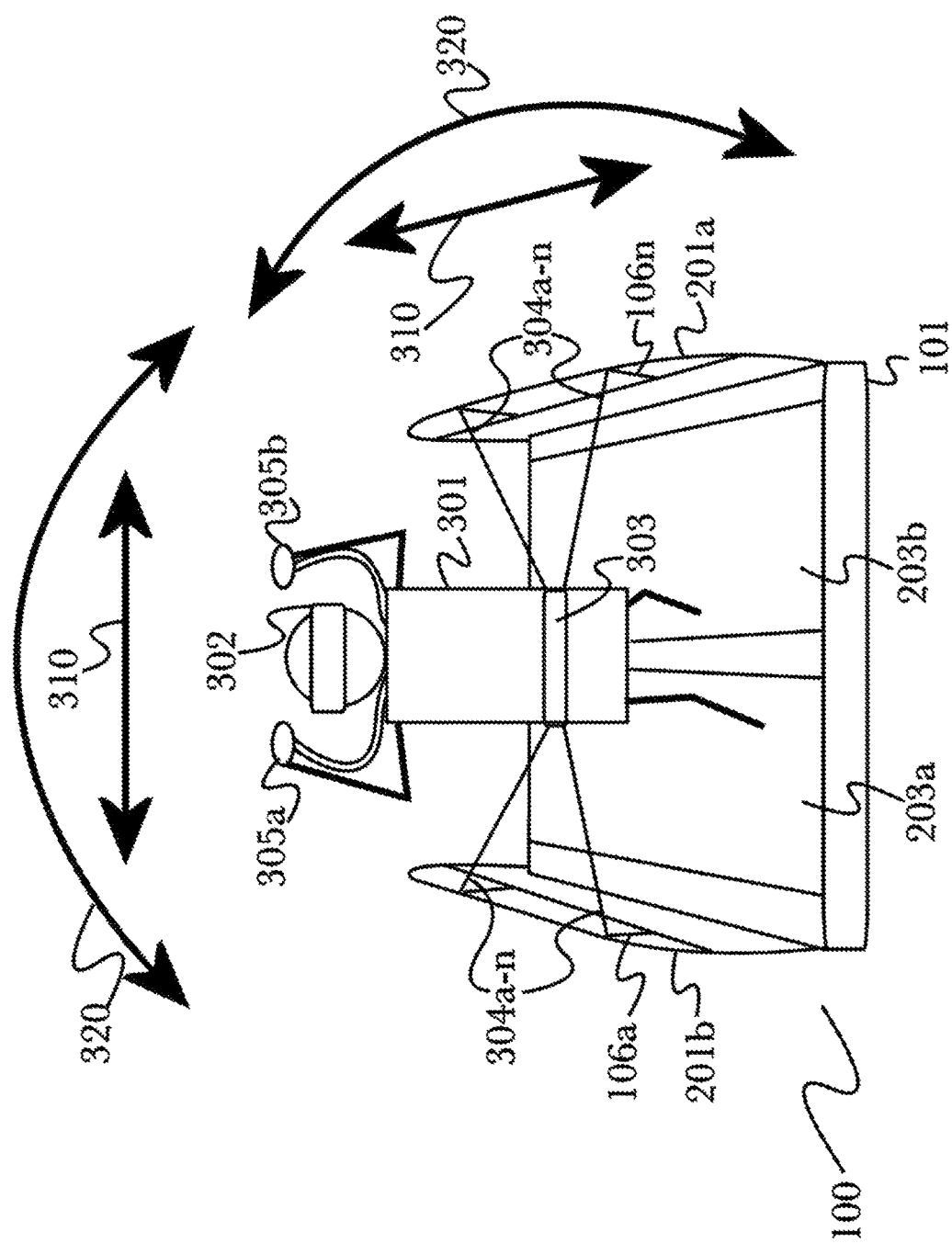
FIG. 3 is a diagram illustrating an exemplary system for a virtual reality or mixed reality enhanced exercise machine, illustrating the use of a plurality of connected smart devices and tethers, and showing interaction via the user's body as a control stick.

FIG. 3 is a diagram illustrating an exemplary system for a virtual reality or mixed reality enhanced exercise machine 100 with wireless communication for smart device control and interactive software applications using a smart device, illustrating the use of a plurality of connected smart devices and tethers, and showing interaction via the user's body as a control stick. According to the embodiment, a user 301 may be standing, walking, or running on a variable-resistance exercise machine 100 with wireless communication for smart device control and virtual reality applications with a stable base 101 and two separate moveable surfaces 203a, 203b for separate movement of the user's legs. Exercise machine 100 may have fixed handlebars with affixed or integrally-formed controllers 305a, 305b for use as connected smart devices for interaction, and support rails 201a, 201b for a user to hold onto or affix tethers for safety or interaction when needed. User 401 may interact with software applications using a variety of means, including manual interaction via controller devices 305a, 305b that may be held in the hand for example to use as motion-input control devices or (as illustrated) may be affixed or integrally-formed into exercise machine 100. This may provide a user with traditional means of interacting with software applications while using exercise machine 100. Additionally, a user's body position or movement may be tracked and used as input, for example via a plurality of tethers 304a-n affixed to handlebars 201a, 201b and a belt, harness or saddle 303 worn by user 301, or using a headset device 302 that may track the position or movement of a user's head as well as provide video (and optionally audio) output to the user, such as a virtual reality headset that displays images while blocking the user's view of the outside world, or an augmented reality or mixed reality headset that combines presented information with the user's view using transparent or semitransparent displays (for example, using transparent OLED displays, hologram displays, projected displays, or other various forms of overlaying a display within a user's normal field of vision without obstructing the user's view). Body tracking may be used to recognize additional input data from user 301 (in addition to manual input via controllers 305a, 305b), by tracking the position and movement of user 301 during use. For example, motion tracking within a headset device 302 may be used to recognize a variety of translational 310 or rotational 320 movement of user's 301 head, such as leaning to the side, or looking over the shoulder. Tethers 304a-n may recognize a variety of movement of user's 301 torso, such as leaning, crouching, side-stepping, or other body movement. This body tracking may then be utilized either as feedback to rehab programs (for example, to track a user's posture for physical therapy coaching or exercises such as holding yoga poses) or input similar to a control stick or joystick in manual controller arrangements, for example by interpreting the user's entire body as the "stick" and processing their body movements as if they were stick movements done manually (such as to control in-game character posture or movement, or to direct movement in certain applications such as vehicle simulations that may turn or accelerate in response to stick movements).

For example, a user 301 on exercise machine 100 may be playing a virtual reality skiing game or rehab program wherein they are given audio and video output via a headset 302 to immerse them in a virtual ski resort. When user 301 is not skiing, they may be able to use manual controls 305a, 305b for such operations as selecting from an on-screen menu, or typing text input such as to input their name or to chat with other players using text. When they begin skiing within the game, user 301 may be instructed in proper ski posture or technique, and may then use their body to control various aspects of their virtual skiing, such as leaning to the side 320 to alter their course and avoid trees or other skiers, or jumping 310 to clear rocks or gaps. Movement of their head may be detected by a headset 302 and used to control their view independently of their body as it is tracked by tethers 304a-n, allowing user 301 to look around freely without interfering with their other controls. In this manner, the user's entire body may serve as an input control device for the game, allowing and encouraging them to use natural body movements to control their gameplay in an immersive manner while still retaining the option to use more familiar manual control means as needed. Alternatively, specific body functions such as hip twisting are used as user feedback for rehabilitating programs, including rehab games.

Figure 12:
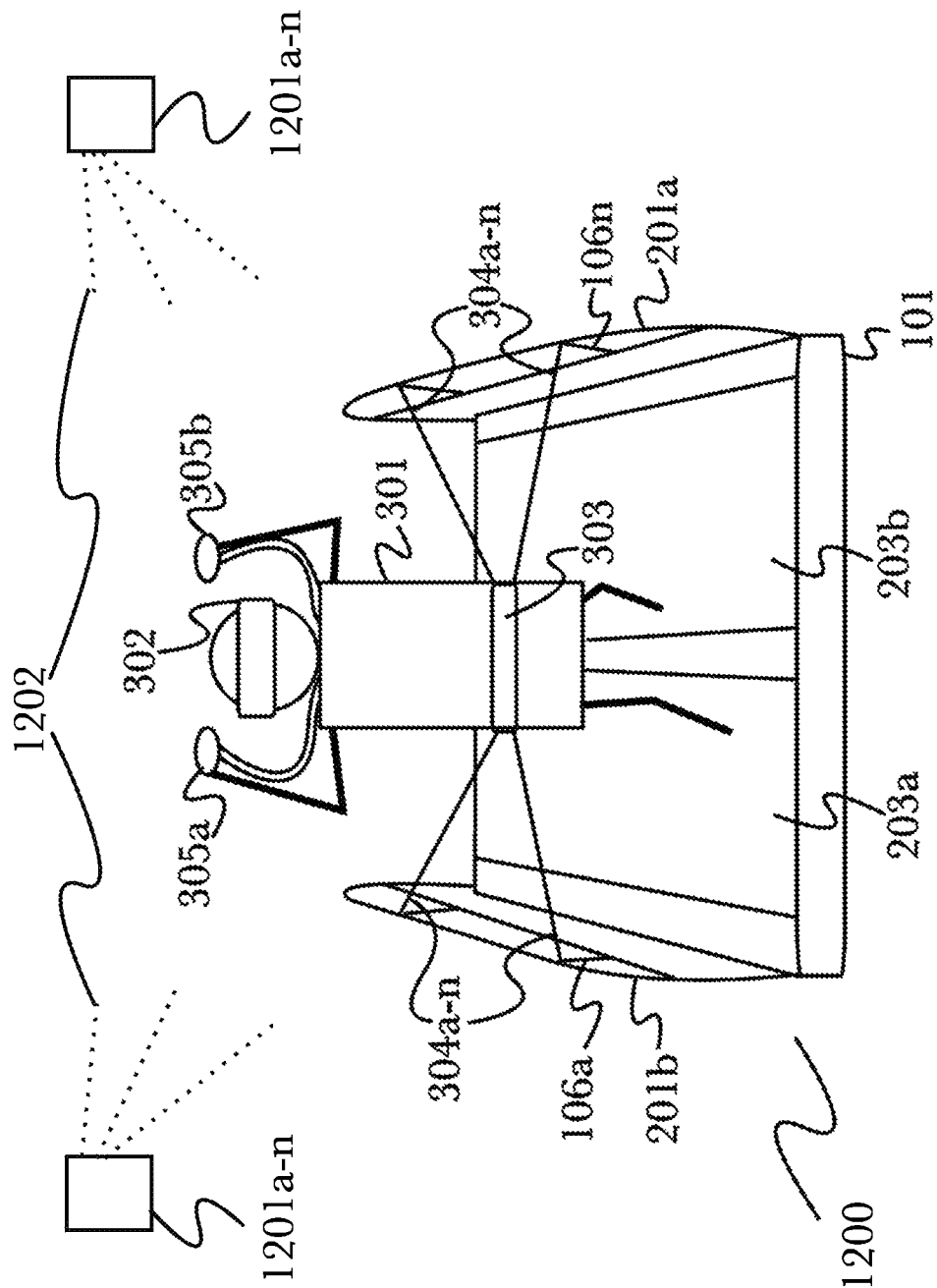
FIG. 12 is a diagram illustrating an exemplary virtual reality or mixed reality enhanced exercise machine, illustrating the use of a plurality of optical sensors to detect body movement of a user during use of an exercise machine.

FIG. 12 is a diagram illustrating an exemplary system 1200 for a virtual reality or mixed reality enhanced exercise machine 100, illustrating the use of a plurality of optical sensors to detect body movement of a user during use of an exercise machine. As above (with reference to FIG. 3), a user 301 may be standing, walking or running, sitting, or otherwise physically active during use of an exercise machine 100. During use, the user's position, posture, movement, cadence, technique, or any other movement or position-related information may be detected, observed, or measured using a plurality of body movement sensors such as (for example, including but not limited to) tethers 304a-n that may optionally be affixed to handlebars 201a-b or other features of an exercise machine 100, hardware sensors integrated into controllers 305a-b or a headset 302 the user may be using during exercise for virtual reality or mixed reality applications, or using a plurality of optical sensors 1201a-n that may be affixed to an exercise machine 100 or adjacent equipment, or that may be affixed to or positioned within an environment around exercise machine 100 to observe the user 301 during use. Optical sensors 1201a-n may be used in a variety of configurations or arrangements, such as using a single wide-angle sensor positioned to observe a user's movement or posture from a particular angle (which may be useful for coaching or physical therapy applications), or using more than one sensor placed about a user to observe their movement in three-dimensional space. A variety of hardware may be utilized in optical sensors 1201a-n, for example including (but not limited to) an infrared or other optical camera that may directly observe the user's movement, a structured-light emitter that projects a structured-light grid 1202 or other arrangement onto the user, exercise machine, or environment (and corresponding scanner or receiver that may observe the user's movement through detected changes in the structured-light projection), or a light-field sensor that detects or measures depth to observe a user's movement in three-dimensions. It should also be appreciated that various combination of optical sensors 1201a-n may be utilized to achieve a desired effect, for example using both structured light and a light-field sensor to observe a user's movement in precise detail in three dimensions. Additionally, some or all optical sensors 1201a-n utilized in some arrangements may be integrated into a user's headset 302 or an exercise machine 100 to provide "inside-out" tracking where tracking sensors are associated with the user rather than the environment, or they may be external devices as illustrated that may be introduced to enhance an existing exercise machine or environment.

Utilizing an exercise machine 100 in this manner allows for a variety of novel forms of user interaction within virtual reality or mixed reality applications. For example, a user's body movement during exercise may be tracked in three dimensions and along or around various axes to record movement with six degrees of freedom (6DOF) comprising both translation along, and rotation about, each of three spatial axes. This may be used with torso tracking as described above (referring to FIGS. 3-7) to produce a 6DOF "torso joystick" virtual device that directs movement or other inputs within a software application. This may be used in a number of ways, for example including but not limited to aiding exercise through interactive coaching (either with a human coach or using software to simulate a coach by providing feedback to detected user movements), providing physical therapy, interacting with games or other applications during exercise, or using exercise combined with software interaction for an immersive virtual reality or mixed reality experience. For example, a user may control movement or expression of a virtual avatar or other user representation within a software application, such as using their own body movements to direct movement of a virtual character. Physical therapy or fitness coaching may utilize detected movements to assist a user with improving their abilities or technique, or to measure progress. Social interaction applications may utilize body movements during exercise, for example a chat or voice call application may utilize body movement as a form of nonverbal expression similar to emoji or other icons. Safety may also be enhanced by controlling the operation of software in response to detected user movements, for example displaying caution information or pausing an application if a user is detected to move outside a configured safety parameter (such as stepping off a running treadmill, for example).

Figure 8:
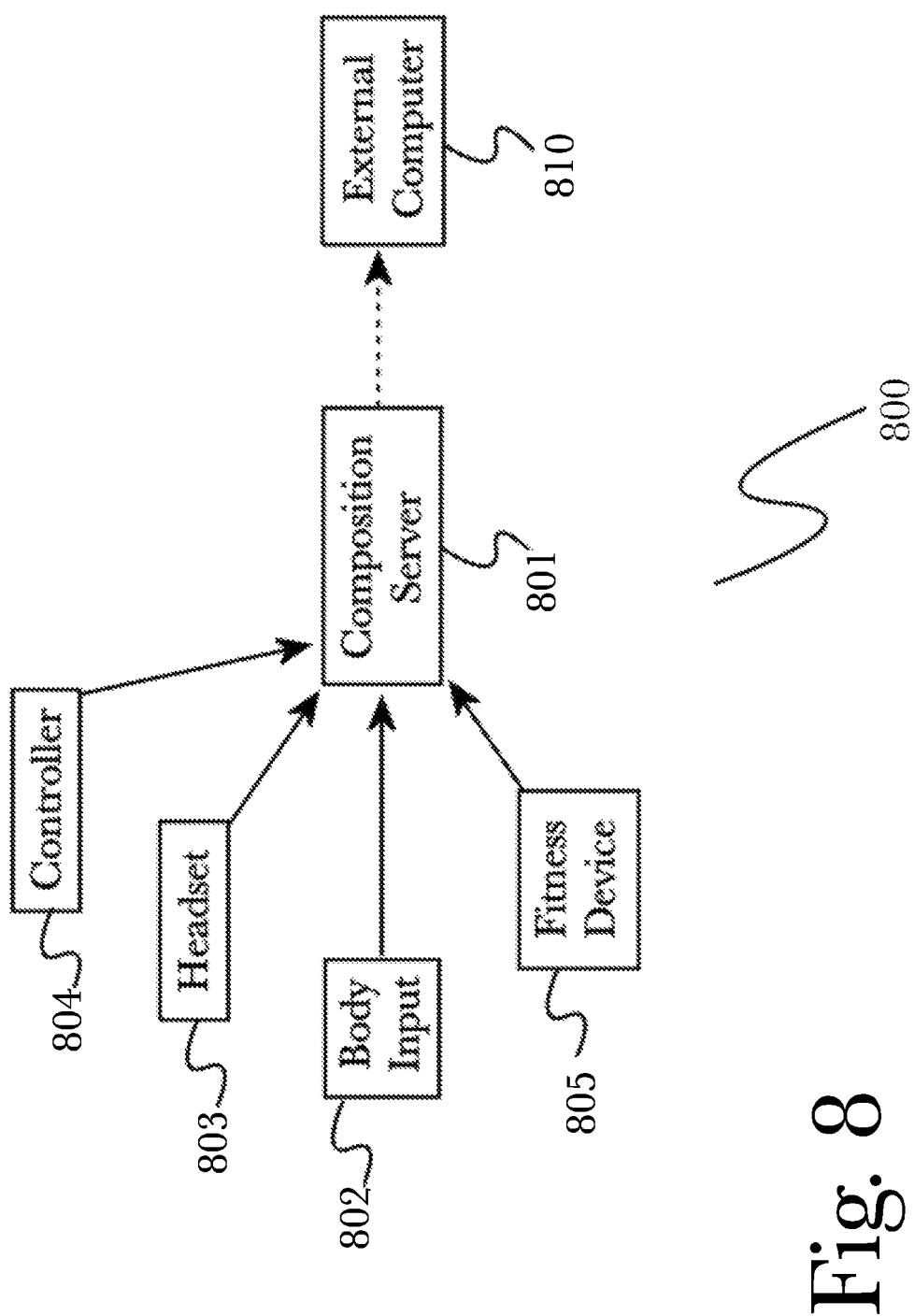
FIG. 8 is a block diagram of an exemplary system architecture for natural body interaction for mixed or virtual reality applications.

FIG. 8 is a block diagram of an exemplary system architecture 800 for natural body interaction for mixed or virtual reality applications of the invention. According to the embodiment, a composition server 801 comprising programming instructions stored in a memory 11 and operating on a processor 12 of a computing device 10 (as described below, with reference to FIG. 13), may be configured to receive a plurality of input data from various connected devices. Such input devices may include (but are not limited to) a variety of hardware controller devices 804 (such as a gaming controller [such as GOJI PLAY™ controllers], motion tracking controller, or traditional computer input devices such as a keyboard or mouse), a headset device 803 such as an augmented reality or mixed or virtual reality headset (for example, OCULUS RIFT™, HTC VIVE™, SAMSUNG GEAR VR™, MICROSOFT MIXED REALITY™, or other headset devices), a variety of fitness devices 805 (for example, fitness tracking wearable devices such as FITBIT™, MICROSOFT BAND™, APPLE WATCH™, or other wearable devices), or a variety of body input 802 tracking devices or arrangements, such as using a plurality of tethers attached to the environment and a harness worn by a user, configured to track movement and position of the user's body.

Various input devices may be connected to composition server 801 interchangeably as desired for a particular arrangement or use case, for example a user may wish to use a controller 804 in each hand and a headset 803, but omit the use of fitness devices 805 altogether. During operation, composition server 801 may identify connected devices and load any stored configuration corresponding to a particular device or device type, for example using preconfigured parameters for use as a default configuration for a new controller, or using historical configuration for a headset based on previous configuration or use. For example, a user may be prompted (or may volunteer) to provide configuration data for a particular device, such as by selecting from a list of options (for example, "choose which type of device this is", or "where are you wearing/holding this device", or other multiple-choice type selection), or composition server 801 may employ machine learning to automatically determine or update device configuration as needed. For example, during use, input values may be received that are determined to be "out of bounds", for example an erroneous sensor reading that might indicate that a user has dramatically shifted position in a way that should be impossible (for example, an erroneous reading that appears to indicate the user has moved across the room and back again within a fraction of a second, or has fallen through the floor, or other data anomalies). These data values may be discarded, and configuration updated to reduce the frequency of such errors in the future, increasing the reliability of input data through use.

Composition server 801 may receive a wide variety of input data from various connected devices, and by comparing against configuration data may discard undesirable or erroneous readings as well as analyze received input data to determine more complex or fine-grained measurements. For example, combining input from motion-sensing controllers 804 with a motion-sensing headset 803 may reveal information about how a user is moving their arms relative to their head or face, such as covering their face to shield against a bright light or an attack (within a game, for example), which might otherwise be impossible to determine with any reliability using only the controllers themselves (as it may be observed that a user is raising their hands easily enough, but there is no reference for the position or movement of their head). These derived input values may then be combined into a single composite input data stream for use by various software applications, such as augmented reality or mixed or virtual reality productivity applications (for example, applications that assist a user in performing manual tasks by presenting virtual information overlays onto their field of vision, or by playing audio directions to instruct them while observing their behavior through input devices, or other such applications), or mixed or virtual reality applications or games, such as simulation games that translate a user's movement or position into in-game interaction, for example by moving a user's in-game character or avatar based on their physical movements as received from input devices. In some arrangements, composition server 801 may operate such software applications in a standalone manner, functioning as a computer or gaming console as needed. In other arrangements, composition server 801 may provide the composite data for use by an external computer 810, such as a connected gaming console, mixed or virtual reality device, personal computer, or a server operating via a network in the cloud (such as for online gaming arrangements, for example). In this manner, the composite data functions of the embodiment may be utilized with existing hardware if desired, or may be provided in a standalone package such as for demonstrations or public use, or for convenient setup using a single device to provide the full interaction experience (in a manner similar to a household gaming console, wherein all the functions of computer components may be prepackaged and setup to minimize difficulty for a new user).

It should be appreciated that while reference is made to virtual reality applications, a wide variety of use cases may be possible according to the embodiment. For example, torso tracking may be used for fitness and health applications, to monitor a user's posture or gait while walking, without the use of additional virtual reality equipment or software. In some arrangements, some or all interaction between a user and a software application may be nonvisual, and in some arrangements no display device may be present. In such an arrangement, a user may interact with software entirely using feedback and movement of a worn harness 420 or tethers 304a-n, using resistance or software-guided actuation of tethers 304a-n (as described below, with reference to FIGS. 4-7) or other elements. In other arrangements, various combinations of display devices and other electronic devices may be used for a mixed-reality setup, for example where a user's movement and interaction may be used by software to incorporate elements of the physical world into a digital representation of the user or environment. For example, a user may interact with games or fitness applications, participate in social media such as chat, calls, online discussion boards, social network postings, or other social content, or they may use body tracking to navigate user interface elements of software such as a web browser or media player. Software used in this manner may not need to be specially-configured to utilize body tracking, for example to navigate a web browser a user's body movements or reactions to feedback may be processed by a composition server 801 and mapped to generic inputs such as keystrokes or mouse clicks, for use in any standard software application without the need for special configuration.

It should be further appreciated that while reference is made to a treadmill-type exercise machine 100, such an exercise machine is exemplary and any of a number of exercise machines may be utilized according to the aspects disclosed herein, for example including (but not limited to) a treadmill, a stationary bicycle, an elliptical machine, a rowing machine, or even non-electronic exercise equipment such as a pull-up bar or weight machine. Traditional exercise equipment may be outfitted with additional components to facilitate virtual reality or mixed reality interaction according to the aspects disclosed herein, for example by affixing a plurality of tethers 304*a-n* to a weight machine so that a user's movement during exercise may be used as interaction as described below (with reference to FIGS. 3-7).

Figure 25:
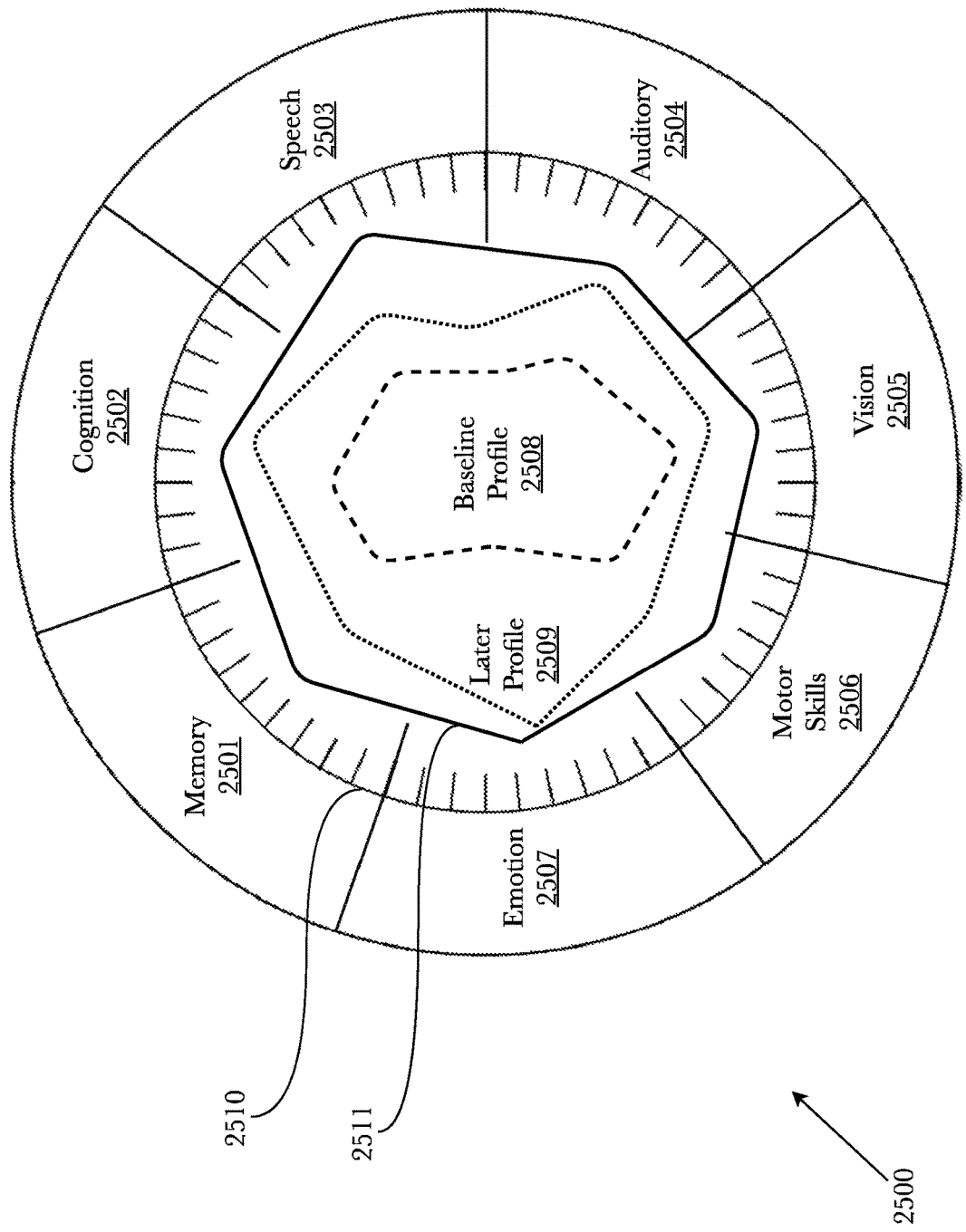
FIG. 25 is a composite functioning score spatial map showing the relative ability of an individual in several physical and mental functional measurement areas.

FIG. 25 is a composite functioning score spatial map 2500 showing the relative ability of a user in several physical and mental functional measurement areas (also referred to herein as "composite functioning scores" or "composite functioning score groups") 2501-2507. The composite functioning score spatial map is a visual representation of a person's ability in several functional measurement areas 2501-2507. The center of the composite functioning score spatial map 2500 represents zero ability, while the inner circle 2510 of the composite functioning score spatial map 2500 represents full ability (i.e., maximum functionality of a healthy individual while not dual-tasking). Greater functionality in a given composite functioning score 2501-2507 is represented by a greater profile coverage area in the direction of that functional measurement area. The average profile area of a representative population of individuals (e.g., of the same age as the individual being tested) is shown as the solid line profile average 2511 of the composite functioning score spatial map 2500. The composite functioning score spatial map 2500 is a visual representation of data obtained from other components of the system and placed into a composite functioning score matrix or other data structure (not shown) which organizes the data relative to the various composite functioning scores.

In this example, there are seven groups of composite functioning scores, each representing either a physical ability, a mental ability, or a combined ability, and all of which together represent a picture of an individual's nervous system function. The memory 2501 and cognition 2502 composite functioning score groups represent purely mental activities, and present a picture of the individual's ability to think clearly. The speech 2503, auditory 2504, and vision 2505 composite functioning score groups represent combined physical/mental activities, as each represents some physical/mental interaction on the part of the individual. For example, speech requires the individual not only to mentally generate words and phrases on a mental level, but also to produce those words and phrases physically using the mouth and vocal cords. It is quite possible, for example, that the individual is able to think of the words, but not produce them, which represents one type of neurological condition. The speech 2503 composite functioning score group represents that combined ability, and the auditory 2504 and vision 2505 composite functioning score groups represent a similar combined ability. The motor skills 2506 composite functioning score group represents a mostly-physical ability to move, balance, touch, hold objects, or engage in other non-cognitive activities (recognizing, of course, that the nervous system controls those movements, but is not engaged in higher-level thinking). The emotional biomarker 2507 group represents the individual's emotional responses to certain stimuli during testing, as would be indicated by lack of empathetic responses to virtual reality characters in a story, responses indicating sadness or depression, etc.

From the data obtained from other components of the system, a profile of an individual's functional ability may be created and displayed on the composite functioning score spatial map. For example, a baseline profile 2508 may be established for an individual during the initial use or uses of the system (e.g., pre-treatment evaluation(s)), showing a certain level of ability for certain composite functioning scores. In the baseline profile 2508 example, all composite functioning scores indicate significant impairment relative to the population average 2511, but the composite functioning scores for cognition 2502 and auditory 2504 ability are relatively stronger than the composite functioning scores for memory 2501, speech 2503, vision 2505, and motor skills 2506, and the emotional biomarker group 2507 indicates substantial impairment relative to the population average 2511. Importantly, changes in the profile can show improvements or regressions in functionality, and changes over time in the profile can be tracked to show trends in improvement or regression. For example, a later profile 2509 for the same individual shows improvement in all biomarker groups, with substantial improvement in the cognition 2502, auditory 2504, motor skill 2506 biomarker groups, and dramatic improvement in the emotion 2507 composite functioning score groups, relative to the baseline profile 2508. The biomarker group for emotion 2507 in the later profile 2509 shows performance matching or nearly matching that of the population average 2511.

Figure 26:
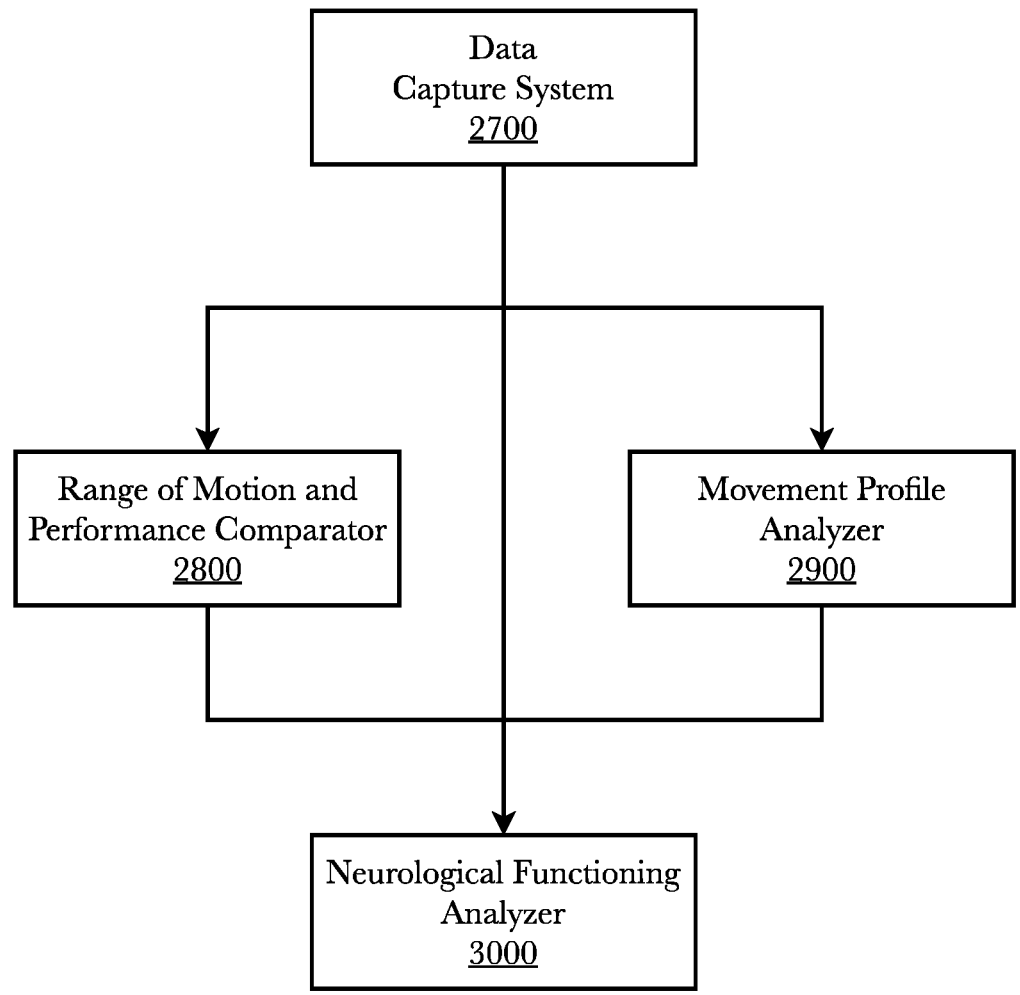
FIG. 26 is an overall system architecture diagram for a neurological functioning analyzer.

FIG. 26 is an overall system architecture diagram for a system for analyzing neurological functioning. In this example, the system comprises a data capture system 2700, a range of motion comparator 2800, a movement profile analyzer 2900, and a neurological functioning analyzer 3000. The data capture system 2700 captures data from sensors on the system such as motor speed sensors, angle sensors, accelerometers, gyroscopes, cameras, and other sensors which provide data about an individual's movement, balance, and strength, as well as information from software systems about tasks being performed by the individual while engaging in exercise. The range of motion comparator 2800 evaluates data from the data capture system 2700 to determine an individual's range of motion relative to the individual's personal history and relative to statistical norms, and to population averages. The movement profile analyzer 2900 evaluates data from the data capture system 2700 to generate a profile of the individual's physical function such as posture, balance, gait symmetry and stability, and consistency and strength of repetitive motion (e.g., walking or running pace and consistency, cycling cadence and consistency, etc.). The neurological functioning analyzer evaluates data from the data capture system 2700, the range of motion comparator 2800, and the movement profile analyzer 2900 to generate a profile of the user's nervous system function as indicated by composite functioning scores which indicate relative ability of an individual in one or more physical and mental functional measurement areas (also referred to herein as "composite functioning scores").

Figure 27:
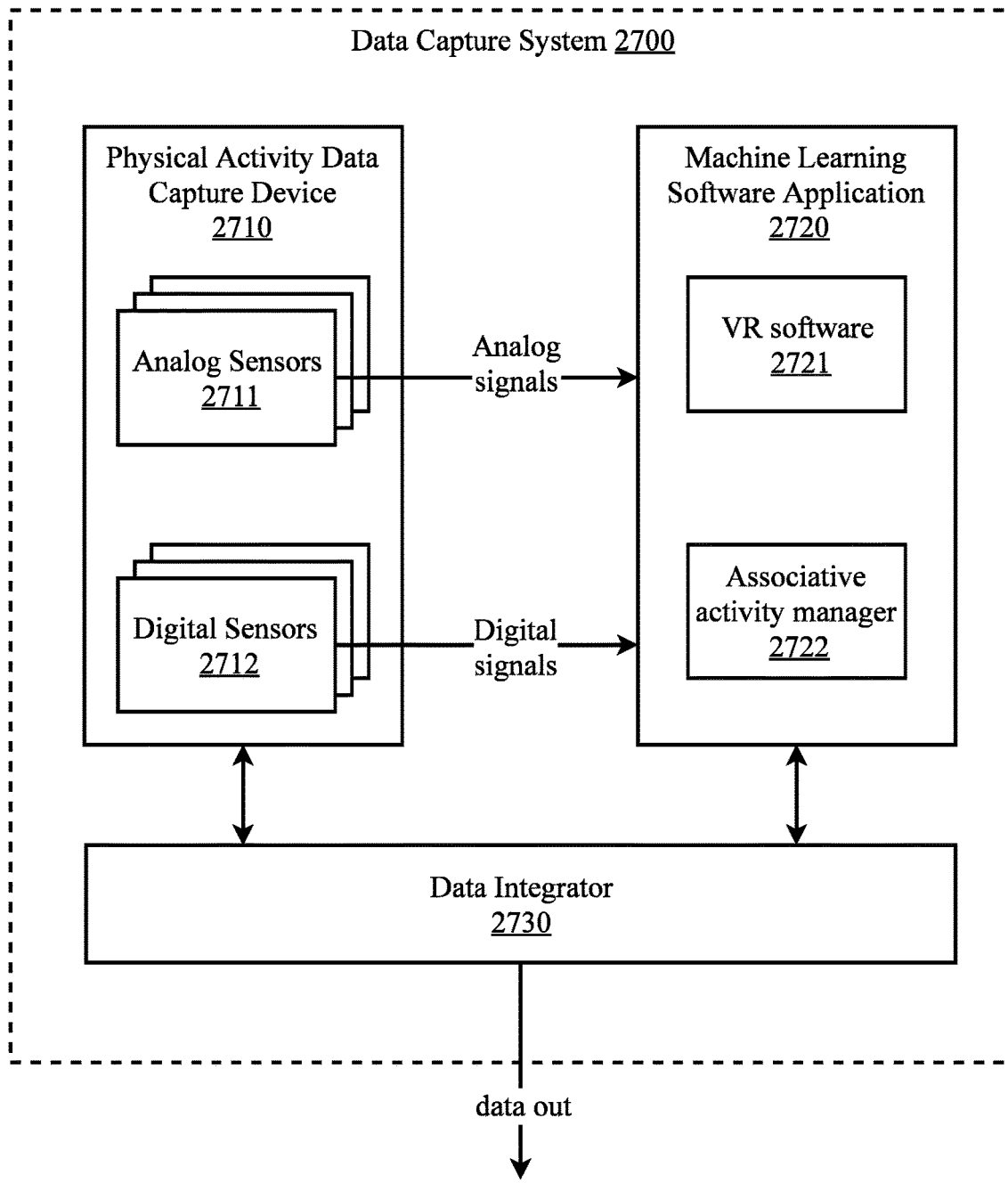
FIG. 27 is a system architecture diagram for the data capture system aspect of a neurological functioning analyzer.

FIG. 27 is a system architecture diagram for the data capture system aspect of a neurological functioning analyzer. In this embodiment, the data capture system 2700 comprises a physical activity data capture device 2710 designed to capture information about an individual's movements while the individual is engaged in a primary physical activity and a software application 2720 designed to assign physical tasks and associative activities, to engage the user in the physical tasks and associative activities, and track and store responses to tasks and activities, as well as a data integrator 2730 configured to convert, calibrate, and integrate data streams from the physical activity data capture device 2710 and software application 2720. The data capture system 2700 captures data from sensors 2711, 2712 on the physical activity data capture device 2710 such as motor speed sensors, angle sensors, accelerometers, gyroscopes, cameras, and other sensors which provide data about the speed, operation, direction and angle of motion of the equipment, and about an individual's movement, balance, and strength.

The physical activity data capture device 2710 may be any type of device that captures data regarding the physical movements and activity of a user. In some embodiments, the physical activity data capture device 2710 may be a stand-alone device not associated with the activity being performed (e.g. a camera, ultrasonic distance sensor, heat sensor, pedometer, or other device not integrated into exercise equipment). In other embodiments, the physical activity data capture device 2710 may be exercise equipment or peripherals that captures motion and activity information of a user engaged in physical activity while using the device. For example, the physical activity data capture device 2710 may be in the form of exercise equipment such as stand-on or ride-on exercise machines like treadmills, stair stepping machines, stationary bicycles, rowing machines, and weight-lifting or resistance devices, or may be other equipment wherein the user stands separately from the equipment and pulls or pushes on ropes, chains, resistance bands, bars, and levers. The physical activity data capture device 2710 may be in the form of computer peripherals (e.g., game controllers, virtual reality headsets, etc.) that capture data while the user is performing physical movements related to a game or virtual reality environment, or exercise equipment that engage the user in physical activity, such as barbells, free weights, etc., which are configured to provide location and/or motion information such an integrated motion sensors or external cameras configured to detect the peripheral. The physical activity data capture device 2710 may be in the form of exercise equipment or peripherals and may be referred to as an exercise device. Sensors in the physical activity data capture device 2710 may be either analog 2711 or digital 2712. Non-limiting examples of analog sensors 2711 are motor voltages and currents, resistors, potentiometers, thermistors, light sensors, and other devices that produce an analog voltages or currents. Most digital sensors are analog sensors 2711 with integrated analog-to-digital converters which output a digital signal, although some sensors are digital in the sense that they measure only discrete steps (e.g., an on/off switch). In most cases, signals from analog sensors 2711 will be converted to digital signals using an analog to digital converter 2701. For signals from digital sensors 2712, conversion is not necessary. In some cases, signals may need to be calibrated by a sensor calibrator, which corrects for sensor drift, out of range errors, etc., by comparing signals to known good values or to other devices.

The software application 2720 is any software designed to assign physical tasks and associative activities, to engage the user in the physical tasks and associative activities, and track and store data from physical tasks and responses to associative activities. The software application 2720 may have, or may use or access, a number of different software components such as a virtual reality game or environment generator 2721, an associative activity manager 2722 which designs, selects, and/or implements testing protocols based on the user's profile. Many different configurations of the software are possible. The software application 2720 may be configured to present tasks to the user independent of inputs from the physical activity data capture device 2710, such as performing playing games, performing math computations, remembering where certain symbols are located, visually following an object on a screen, or reading and speaking a given text. Alternatively, the software application 2720 may be configured to engage the user in mental or combined activities that correspond in some way to the inputs from the physical activity data capture device 2710. For example, the user might be running on a treadmill, and the speed of the treadmill might be used as an input to a virtual reality environment which shows the user virtually running at a rate corresponding to the rate of the real world treadmill speed. The software application 2720 is configured to record data regarding, or evaluate and assign scores or values to, the user's responses and reactions to the tasks presented by the software application 2720. For example, if the user is assigned the task of performing a mathematical calculation, the correctness of the user's response may be evaluated, scored, and recorded as data. As another example, the user may be presented with the task of speeding up or slowing down a running motion in response to a visual cue, and the speed of the user's reaction may be recorded as data. In such cases, a data integrator 2730 may be used to integrate the data from the physical activity data capture device 2710 with the data from the software application 2720. In some embodiments, the data from the physical activity data capture device 2710 may be used to change the operation of the software application 2720, and vice versa (i.e., the software application 2720 may also be used change the operation of the exercise equipment, for example, providing additional resistance or speeding up the operation of a treadmill). In some embodiments, the data integrator may not be a separate component, and its functionality may be incorporated into other components, such as the software application 2720.

In some embodiments, the software application 2720, another machine-learning based software application such as a task assignment software application (not shown), may be configured to assign physical tasks to the user to be performed in conjunction with the associative activities assigned. Rather than simply performing continuously performing physical activity and recording the impact on the physical activity of performance of the associative activities, the user may be assigned discrete physical tasks to perform while a mental activity is being performed. For example, the user may be assigned the physical task of pointing to a fixed spot on a display screen while reading aloud a text, and the steadiness of the user's pointing may be measured before, during, and after the reading, thus indicating an impact on the user's physical activity of the mental effort. Such dual-task testing may allow for more precise measurement and evaluation of relative functioning as different combinations of physical and associative activities are evaluated together. In some embodiments, the associative activity may be a second physical task or activity assigned to be performed simultaneously with a primary physical task or activity. Note that the terms "task" and "activity" as used herein are interchangeable, although the phrases "physical task" and "associative activity" are often used for purposes of clarity and convenience.

Figure 28:
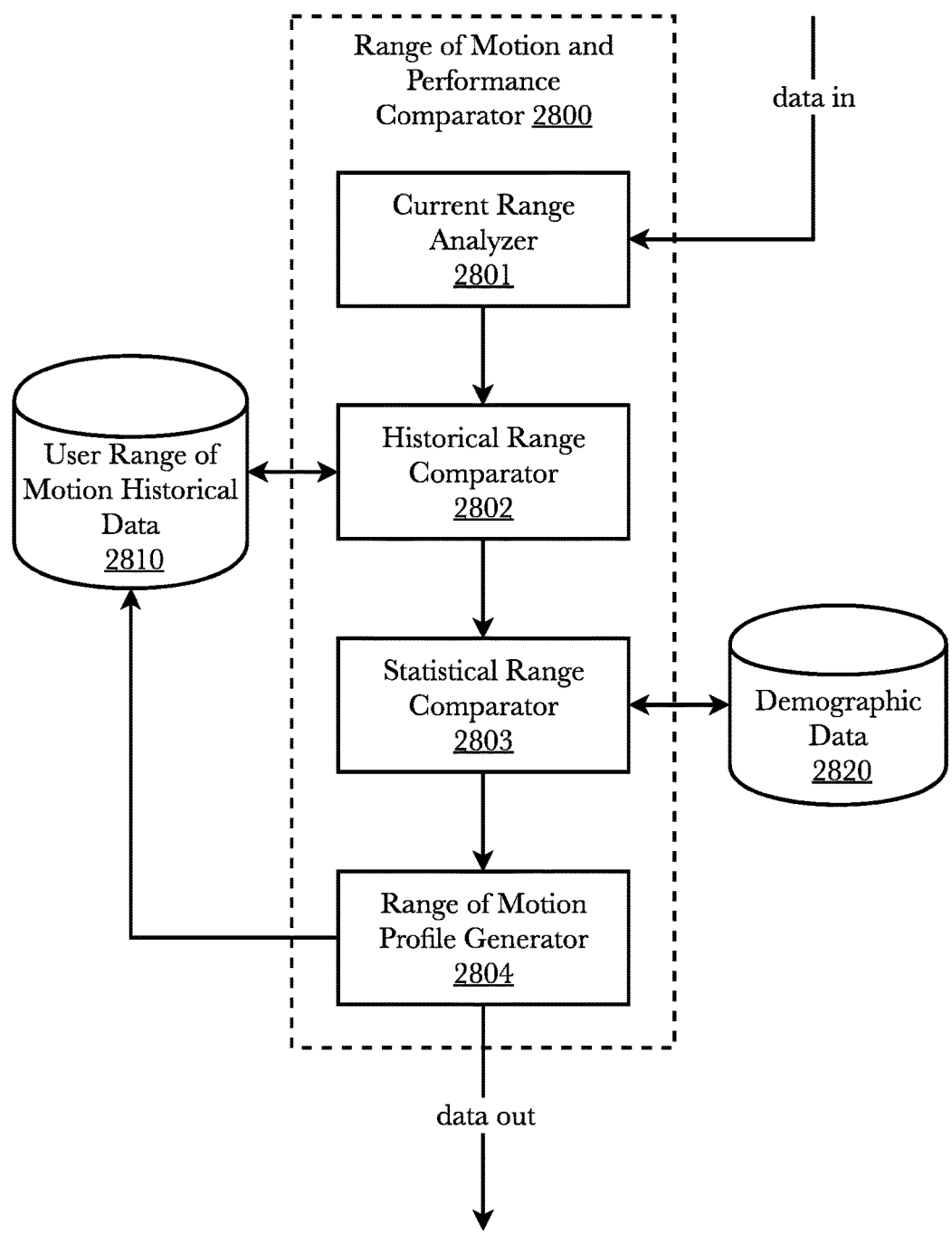
FIG. 28 is a system architecture diagram for the range of motion comparator aspect of a neurological functioning analyzer.

FIG. 28 is a system architecture diagram for the range of motion comparator aspect of a neurological functioning analyzer. The range of motion and performance comparator 2800 evaluates data from the data capture system 2700 to determine an individual's range of motion and performance for the given associative activity relative to the individual's personal history and relative to statistical norms. The range of motion and performance comparator 2800 comprises a current range analyzer 2801, a historical range comparator 2802, a statistical range comparator 2803, and a range of motion and performance profile generator 2804, as well as databases for user range of motion and performance historical data 2810 and demographic data 2820. The current range analyzer 2801 ingests data related to an individual's movement and performance, and calculates a range of motion and performance of that individual while performing versus not performing the given associative activity. For example, if an individual is given a primary physical task of standing in balance and an associative activity of popping a virtual balloon of a specific color as it appears randomly in the VR environment, the current range analyzer 2801 will start tracking the individual's balance while performing the associative activity and measure the accuracy and timing of balloon popping (for testing the individual's gross motor and executive functions). To conclude, the individual is instructed to start walking to warm up, and then repeat the same balloon popping activity while walking. The current range analyzer 2801 will finish capturing all the motion and performance data—the differences in the individual's accuracy and timing of balloon popping between standing and walking as well as the nuanced changes in the individual's walking movement during warmup and while balloon popping—and forwarding its analysis to the historical range comparator 2801. The historical range comparator 2802 retrieves historical data for the individual (if such exists) from a user range of motion and performance historical data database 2810, and compares the current data with historical data to determine trends in the individual's motion and performance over time. The statistical range comparator 2803 retrieves statistical range data for populations similar to the individual from a demographic data database 2820, and determines a range of motion and performance of the individual relative to similar individuals by sex, age, height, weight, health conditions, etc. The range of motion and performance profile generator 2804 takes the data from the prior components, and generates and stores a range of motion profile for the individual which integrates these analyses into a comprehensive picture of the individual's range of motion functionality.

Figure 29:
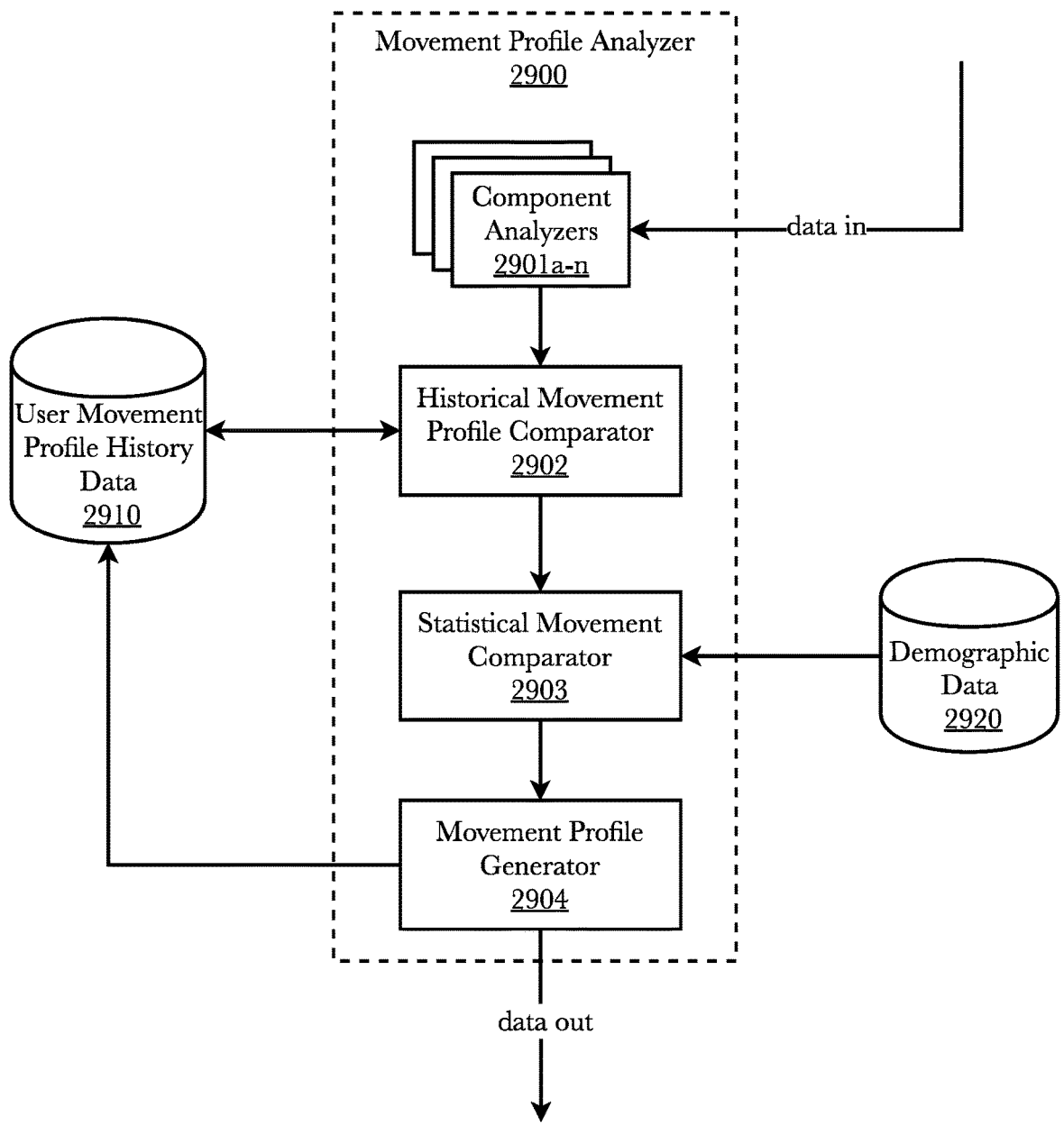
FIG. 29 is a system architecture diagram for the movement profile analyzer aspect of a neurological functioning analyzer.

FIG. 29 is a system architecture diagram for the movement and performance profile analyzer aspect of a neurological functioning analyzer. The movement and performance profile analyzer 2900 evaluates data from the data capture system 2700 to generate a profile of the individual's physical function such as posture, balance, gait symmetry and stability, and consistency and strength of repetitive motion (e.g., walking or running pace and consistency, cycling cadence and consistency, etc.) and mental performance such as executive function, cognitive response, visual and auditory functions, emotional or empathetic reactions, etc. The movement and performance profile analyzer 2900 comprises a number of component analyzers 2901*a-n*, a historical movement and performance profile comparator 2902, a statistical movement and performance comparator 2903, and a movement and performance profile generator 2904, as well as a user movement and performance profile history data database 2910 and a demographic data database 2920.

Many different aspects of movement and performance may be analyzed by the movement and performance profile analyzer 2900 through one or more of its many component analyzers 2901*a-n* such as the gait analyzer, balance analyzer, gross motor analyzer, fine motor analyzer, depth perception analyzer, executive function analyzer, visual function analyzer, auditory function analyzer, memory function analyzer, emotional response analyzer, etc. For example, the gait analyzer of the component analyzers 2901 ingests sensor data related to an individual's ambulatory movements (walking or running) while performing the given associative activity, and calculates a step frequency, step symmetry, weight distribution, and other metrics related to an individual's gait. These calculations are then compared to expected calculations for an individual without performing the given the associative activity. If an individual exhibits a limp while performing the given associative activity (e.g., popping virtual balloons), the step frequency, step symmetry, and weight distribution will all be skewed with the impaired side showing a shorter step duration and less weight applied. The expected calculations may be determined from the full range of sensor values, per-exercise calibrations, statistical data, or other means appropriate to the specific application. The balance analyzer of the component analyzer 2901 performs a similar function with respect to an individual's balance. Wobbling, hesitation, or partial falls and recoveries while performing a range of associative activities can be calculated from the data. The historical movement and performance comparator 2902 retrieves historical data for the individual (if such exists) from a user movement and performance historical data database 2910, and compares the current movement and performance data with historical data to determine trends in the movements and performances over time. The statistical movement and performance comparator 2903 retrieves statistical range of motion and performance data for populations similar to the individual from a demographic data database 2920, and compares movements and performances of the individual to similar individuals by sex, age, height, weight, health conditions, etc. The movement and performance profile generator 2905 takes the data from the prior components, and generates and stores a movement and performance profile for the individual which integrates these analyses into a comprehensive picture of the individual's movement and performance functionality.

Figure 30:
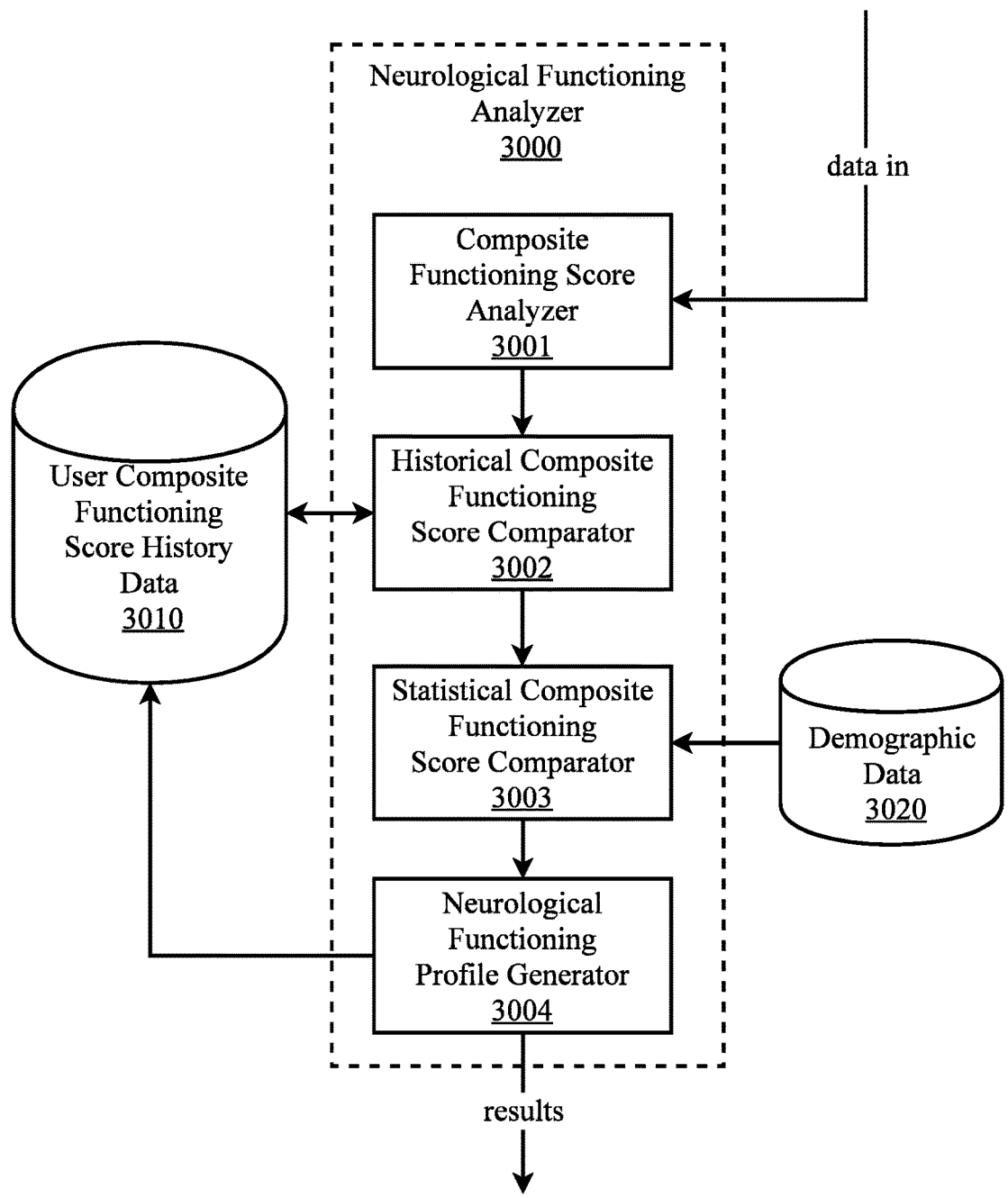
FIG. 30 is a system architecture diagram for the neurological functioning analyzer aspect of a neurological condition evaluator.

FIG. 30 is a system architecture diagram for the neurological functioning analyzer aspect of a neurological condition evaluator. The neurological functioning analyzer evaluates data from the data capture system 2700, the range of motion and performance comparator 2800, and the movement and performance profile analyzer 2900 to generate a profile of the user's nervous system function as indicated by composite functioning scores which indicate relative ability of an individual in one or more physical and mental functional measurement areas (also referred to herein as "composite functioning scores"). The current composite functioning score analyzer 3001 ingests sensor data related to an individual's movement and performance, and calculates a set of current composite functioning scores for that individual based on the sensor data, the range of motion and performance profile, the movement and performance profile, and input from the software 2720 regarding associative activities associated with physical movement data. The historical composite functioning score comparator 3002 retrieves historical data for the individual (if such exists) from a user composite functioning score historical data database 3010, and compares the current composite functioning score data with historical data to determine trends in the individual's bio-makers over time. The statistical composite functioning score comparator 3003 retrieves statistical composite functioning score data for populations similar to the individual from a demographic data database 3020, and determines a range of composite functioning score functionality of the individual relative to similar individuals by sex, age, height, weight, health conditions, etc. The neurological functioning profile generator 3004 takes the data from the prior components, and generates and stores a neurological functioning profile for the individual which integrates these analyses into a comprehensive picture of the individual's composite functioning score functionality. In some embodiments, one or more of the composite functioning scores may be determined from dual-task testing, in which a physical task and a mental task are performed simultaneously to detect areas of abnormal nervous system function, and/or identify which areas of the nervous system may be affected. For example, while performing mathematical tasks, an individual slows down significantly in his/her walk compared to the population data. It will indicate that the individual's composite functioning score for logical and mathematic functions is worse than his/her population cohort (by sex, age, height, weight, health conditions, etc.). The neurological functioning profile may include a composite functioning score spatial map as described above. In some embodiments, the neurological functioning analyzer may receive data directly from the data capture system 2700 and may perform independent neurological analyses without inputs from the range of motion and performance comparator 2800 or the movement and performance profile analyzer 2900, or may incorporate some or all of the functionality of those components.

Detailed Description of Exemplary Aspects

Figure 2:
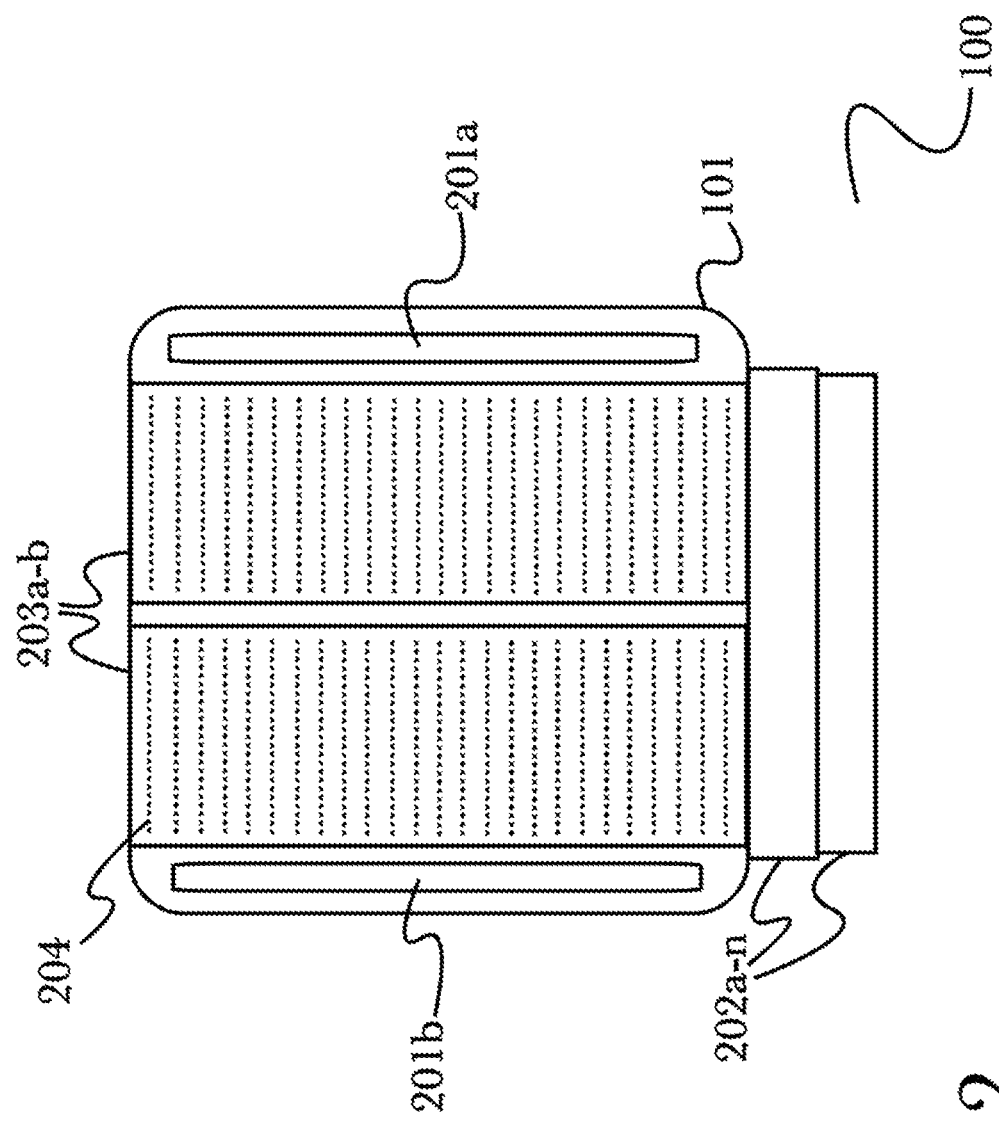
FIG. 2 is a top-down view of an exemplary variable-resistance exercise machine with an embedded or a wireless computing device controlling the interactive software applications of the invention.

FIG. 2 is a top-down view of a variable-resistance exercise machine 100 with wireless communication for smart device control and interactive software applications of the invention. According to the embodiment, exercise machine 100 may comprise a stable base 101 to provide a platform for a user to safely stand or move about upon. Exercise machine 100 may further comprise right 201*a* and left 201*b* hand rails for a user to brace against or grip during use, to provide a stable support for safety as well as a mounting point for external devices such as a plurality of tethers, as described below with reference to FIG. 3. A plurality of steps 202*a-n* may be used to provide a user with a safe and easy means to approach or dismount exercise machine 100, as well as a nonmoving "staging area" where a user may stand while they configure operation or wait for exercise machine 100 to start operation. Unlike traditional treadmill machines common in the art, exercise machine 100 may be made with greater width to accommodate a wider range of free movement of a user's entire body (whereas traditional treadmills are designed to best accommodate only a jogging or running posture, with minimal lateral motion), and a plurality of separate moving surfaces 203*a-b* may be utilized to provide multiple separate surfaces that may move and be controlled independently of one another during use. For example, a user may move each of their legs independently without resistance applied, with separate moving surfaces 203*a-b* moving freely underfoot as a user applies pressure during their movement. This may provide the illusion of movement to a user while in reality they remain stationary with respect to their surroundings. Another use may be multiple separate moving surfaces 203*a-b*, with separate speeds of movement or degrees of resistance, so that as a user moves about during use they may experience physical feedback in the form of changing speed or resistance, indicating where they are standing or in what direction they are moving (for example, to orient a user wearing a virtual reality headset, as described below with reference to FIG. 3). Moving surfaces 203*a-b* may be formed with a texture 204 to increase traction, which may improve user safety and stability during use as well as improve the operation of moving surfaces 203*a-b* for use in multidirectional movement (as the user's foot is less likely to slide across a surface rather than taking purchase and applying directional pressure to produce movement). Use of multiple, multidirectional moving surfaces 203*a-b* may also be used in various therapeutic or rehabilitation roles, for example to aid a user in developing balance or range of motion. For example, a user who is recovering from an injury or surgery (such as a joint repair or replacement surgery) may require regular physical therapy during recovery. Use of multidirectional moving surfaces 203*a-b* along with appropriate guidance from a rehabilitation specialist or physical therapist (or optionally a virtual or remote coach using a software application) may make regular therapy more convenient and accessible to the user, rather than requiring in-home care or regular visits to a clinic. For example, by enabling a therapist or coach to manually vary the movement and resistance of the moving surfaces 203*a-b*, they can examine a user's ability to overcome resistance to different movements such as at odd angles or across varying range of motion, to examine the user's physical health or ability. By further varying the resistance it becomes possible to assist the user with rehabilitation by providing targeted resistance training to specific movements, positions, or muscle groups to assist in recovery and development of the user's abilities.

Exercise machine 100 may be designed without a control interface commonly utilized by exercise machines in the art, instead being configured with any of a variety of wireless network interfaces such as Wi-Fi or BLUETOOTH™ for connection to a user's smart device, such as a smartphone or tablet computer. When connected, a user may use a software application on their device to configure or direct the operation of exercise machine 100, for example by manually configuring a variety of operation settings such as speed or resistance, or by interacting with a software application that automatically directs the operation of exercise machine 100 without exposing the particular details of operation to a user. Additionally, communication may be bi-directional, with a smart device directing the operation of exercise machine 100 and with exercise machine 100 providing input to a smart device based at least in part on a user's activity or interaction. For example, a user may interact with a game on their smart device, which directs the operation of exercise machine 100 during play as a form of interaction with, and feedback to, the user. For example, in a racing game, exercise machine 100 may alter the resistance of moving surfaces 203*a-b* as a user's speed changes within the game. In another example, a user may be moving about on moving surfaces 203*a-b* while playing a simulation or roleplaying game, and their movement may be provided to the connected smart device for use in controlling an in-game character's movement. Another example may be two-way interactive media control, wherein a user may select media such as music for listening on their smart device, and then while using exercise machine 100 their level of exertion (for example, the speed at which they run or jog) may be used to provide input to their smart device for controlling the playback of media. For example, if the user slows down music may be played slowly, distorting the audio unless the user increases their pace. In this manner, exercise machine 100 may be used interchangeably as a control and feedback device or both simultaneously, providing an immersive environment for a wide variety of software applications such as virtual reality, video games, fitness and health applications, or interactive media consumption.

Figure 4:
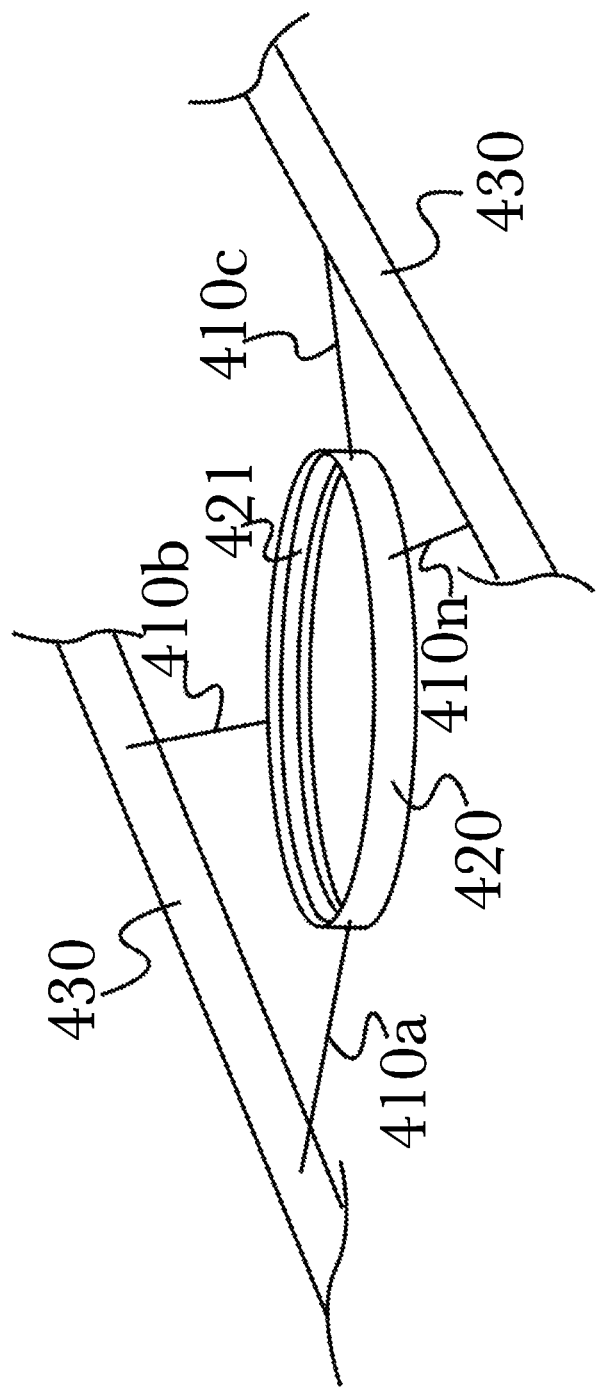
FIG. 4 is a diagram of an exemplary apparatus for natural torso tracking and feedback for electronic interaction, illustrating the use of multiple tethers and a movable torso harness.

FIG. 4 is a diagram of an exemplary hardware arrangement 400 for natural torso tracking and feedback for electronic interaction according to a preferred embodiment of the invention, illustrating the use of multiple tethers 410a-n and a movable torso harness 420. According to the embodiment, a plurality of tethers 410a-n may be affixed or integrally-formed as part of a handle or railing 430, such as handlebars found on exercise equipment such as a treadmill, elliptical trainer, stair-climbing machine, or the like. In alternate arrangements, specifically-designed equipment with integral tethers 410a-n may be used, but it may be appreciated that a modular design with tethers 410a-n that may be affixed and removed freely may be desirable for facilitating use with a variety of fitness equipment or structural elements of a building, according to a user's particular use case or circumstance. Tethers 410a-n may then be affixed or integrally-formed to a torso harness 420, as illustrated in the form of a belt, that may be worn by a user such that movement of their body affects tethers 410a-n and applies stress to them in a variety of manners. It should be appreciated that while a belt design for a torso harness 420 is shown for clarity, a variety of physical arrangements may be used such as including (but not limited to) a vest, a series of harness-like straps similar to climbing or rappelling equipment, a backpack, straps designed to be worn on a user's body underneath or in place of clothing (for example, for use in medical settings for collecting precise data) or a plurality of specially-formed clips or attachment points that may be readily affixed to a user's clothing. Additionally, a torso harness 420 may be constructed with movable parts, for example having an inner belt 421 that permits a user some degree of motion within the harness 420 without restricting their movement. Movement of inner belt 421 (or other movable portions) may be measured in a variety of ways, such as using accelerometers, gyroscopes, or optical sensors, and this data may be used as interaction with software applications in addition to data collected from tethers 410a-n as described below. In some embodiments, a saddle-like surface on which a user may sit may be used, with motion of the saddle-like surface measured as described generally herein.

As a user moves, his or her body naturally shifts position and orientation. These shifts may be detected and measured via tethers 410a-n, for example by detecting patterns of tension or strain on tethers 410a-n to indicate body orientation, or by measuring small changes in strain on tethers 410a-n to determine more precise movements such as body posture while a user is speaking, or specific characteristics of a user's stride or gait. Additionally, through varying the quantity and arrangement of tethers 410a-n, more precise or specialized forms of movement may be detected and measured (such as, for example, using a specific arrangement of multiple tethers connected to a particular area of a user's body to detect extremely small movements for medical diagnosis or fitness coaching). This data may be used as interaction with software applications, such as for virtual reality applications as input for a user to control a character in a game. In such an arrangement, when a user moves, this movement may be translated to an in-game character or avatar to convey a more natural sense of interaction and presence. For example, in a multiplayer roleplaying game, this may be used to facilitate nonverbal communication and recognition between players, as their distinct mannerisms and gestures may be conveyed in the game through detection of natural torso position and movement. In fitness or health applications, this data may be used to track and monitor a user's posture or ergonomic qualities, or to assist in coaching them for specific fitness activities such as holding a pose for yoga, stretching, or proper running form during use with a treadmill. In medical applications, this data may be used to assist in diagnosing injuries or deficiencies that may require attention, such as by detecting anomalies in movement or physiological adaptations to an unrecognized injury (such as when a user subconsciously shifts their weight off an injured foot or knee, without consciously realizing an issue is present).

Through various arrangements of tethers 410a-n and tether sensors (as described below, referring to FIGS. 5-7), it may be possible to enable a variety of immersive ways for a user to interact with software applications, as well as to receive haptic feedback from applications. For example, by detecting rotation, tension, stress, or angle of tethers a user may interact with applications such as virtual reality games or simulations, by using natural body movements and positioning such as leaning, jumping, crouching, kneeling, turning, or shifting their weight in various directions to trigger actions within a software application configured to accept torso tracking input. By applying haptic feedback of varying form and intensity (as is described in greater detail below, referring to FIG. 5), applications may provide physical indication to a user of software events, such as applying tension to resist movement, pulling or tugging on a tether to move or "jerk" a user in a direction, or varying feedback to multiple tethers such as tugging and releasing in varying order or sequence to simulate more complex effects such as (for example, in a gaming use case) explosions, riding in a vehicle, or walking through foliage.

Figure 5:
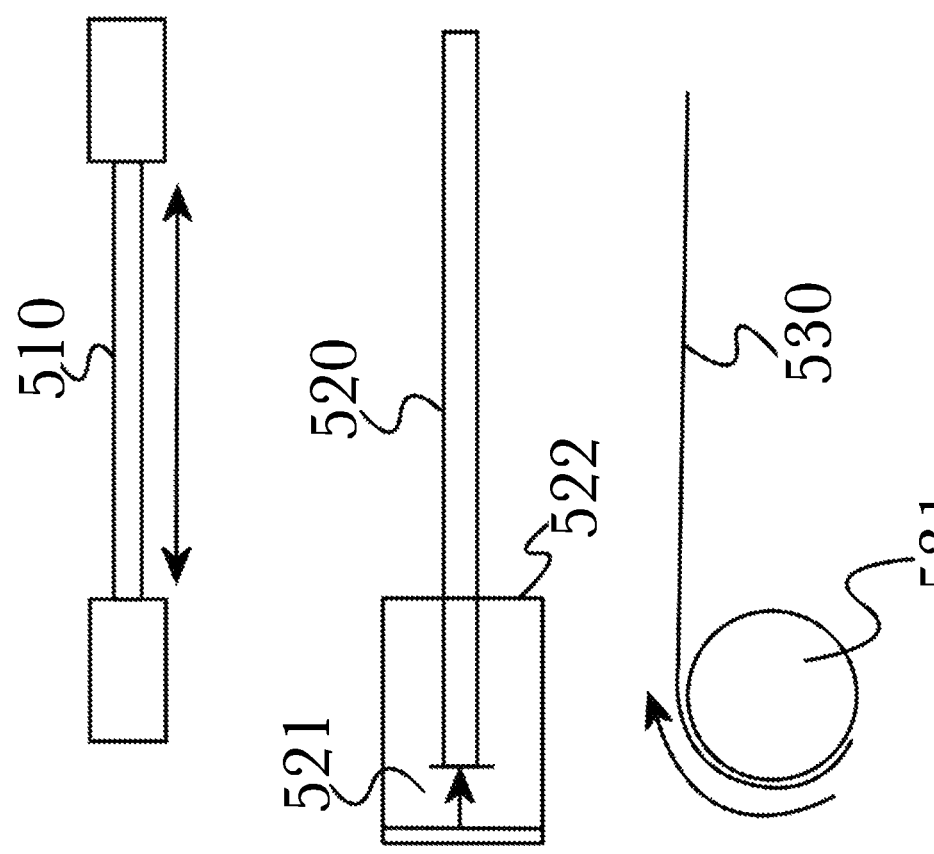
FIG. 5 is a diagram illustrating a variety of alternate tether arrangements.

FIG. 5 is a diagram illustrating a variety of alternate tether arrangements. According to various use cases and hardware arrangements, tethers 410a-n may utilize a variety of purpose-driven designs as illustrated. For example, a "stretchable" tether 510 may be used to measure strain during a user's movement, as the tether 510 is stretched or compressed (for example, using piezoelectric materials and measuring electrical changes). Such an arrangement may be suitable for precise measurements, but may lack the mechanical strength or durability for gross movement detection or prolonged use. An alternate construction may utilize a non-deforming tether 520 such as a steel cable or similar non-stretching material. Instead of measuring strain on the tether 520, instead tether 520 may be permitted a degree of movement within an enclosure 522 (for example, an attachment point on a torso harness 420 or handlebar 430), and the position or movement 521 of the tether 520 may be measured such as via optical sensors. In a third exemplary arrangement, a tether 530 may be wound about an axle or pulley 531, and may be let out when force is applied during a user's movement. Rotation of the pulley 531 may be measured, or alternately a tension device such as a coil spring may be utilized (not shown) and the tension or strain on that device may be measured as tether 530 is extended or retracted. In this manner, it may be appreciated that a variety of mechanical means may be used to facilitate tethers and attachments for use in detecting and measuring natural torso position and movement, and it should be appreciated that a variety of additional or alternate hardware arrangements may be utilized according to the embodiments disclosed herein.

Additionally, through the use of various hardware construction it becomes possible to utilize both "passive" tethers that merely measure movement or strain, as well as "active" tethers that may apply resistance or movement to provide haptic feedback to a user. For example, in an arrangement utilizing a coiled spring or pulley 531, the spring or pulley 531 may be wound to retract a tether and direct or impede a user's movement as desired. In this manner, various new forms of feedback-based interaction become possible, and in virtual reality use cases user engagement and immersion are increased through more natural physical feedback during their interaction.

By applying various forms and intensities of feedback using various tether arrangements, a variety of feedback types may be used to provide haptic output to a user in response to software events. For example, tension on a tether may be used to simulate restrained movement such as wading through water or dense foliage, walking up an inclined surface, magnetic or gravitational forces, or other forms of physical resistance or impedance that may be simulated through directional or non-directional tension. Tugging, retracting, or pulling on a tether may be used to simulate sudden forces such as recoil from gunfire, explosions, being grabbed or struck by a software entity such as an object or character, deploying a parachute, bungee jumping, sliding or falling, or other momentary forces or events that may be conveyed with a tugging or pulling sensation. By utilizing various patterns of haptic feedback, more complex events may be communicated to a user, such as riding on horseback or in a vehicle, standing on the deck of a ship at sea, turbulence in an aircraft, weather, or other virtual events that may be represented using haptic feedback. In this manner, virtual environments and events may be made more immersive and tangible for a user, both by enabling a user to interact using natural body movements and positioning, as well as by providing haptic feedback in a manner that feels natural and expected to the user. For example, if a user is controlling a character in a gaming application through a first-person viewpoint, it would seem natural that when their character is struck there would be a physical sensation corresponding to the event; however, this is not possible with traditional interaction devices, detracting from any sense of immersion or realism for the user. By providing this physical sensation alongside the virtual event, the experience becomes more engaging and users are encouraged to interact more naturally as their actions results in natural and believable feedback, meeting their subconscious expectations and avoiding excessive "immersion-breaking" moments, which in turn reduces the likelihood of users adopting unusual behaviors or unhealthy posture as a result of adapting to limited interaction schema.

Haptic feedback may be provided to notify a user of non-gaming events, such as for desktop notifications for email or application updates, or to provide feedback on their posture for use in fitness or health coaching. For example, a user may be encouraged to maintain a particular stance, pose, or posture while working or for a set length of time (for example, for a yoga exercise application), and if their posture deviates from an acceptable range, feedback is provided to remind them to adjust their posture. This may be used in sports, fitness, health, or ergonomic applications that need not utilize other aspects of virtual reality and may operate as traditional software applications on nonspecialized computing hardware. For example, a user at their desk may use an ergonomic training application that monitors their body posture throughout the work day and provides haptic reminders to correct poor posture as it is detected, helping the user to maintain a healthy working posture to reduce fatigue or injuries due to poor posture (for example, repetitive-stress injuries that may be linked to poor posture while working at a computer).

Figure 6:
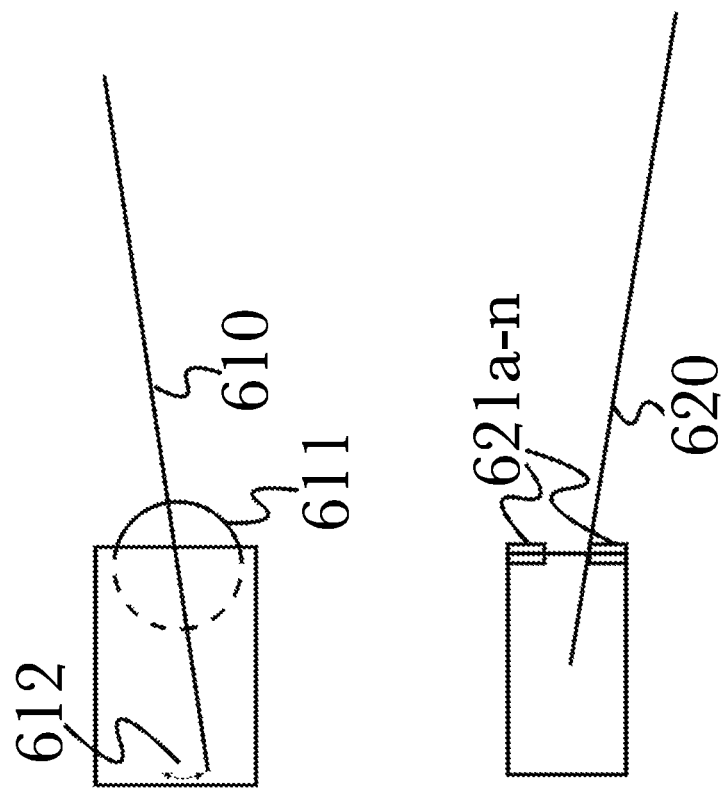
FIG. 6 is a diagram of an additional exemplary apparatus for natural torso tracking and feedback for electronic interaction, illustrating the use of angle sensors to detect angled movement of tethers.

FIG. 6 is a diagram of an additional exemplary hardware arrangement 600 for natural torso tracking and feedback for electronic interaction according to a preferred embodiment of the invention, illustrating the use of angle sensors 612, 621*a*-*n* to detect angled movement of a tether 620. According to one exemplary arrangement, a tether 610 may be affixed to or passed through a rotating joint such as a ball bearing 611 or similar, to permit free angular movement. During movement, the angular movement or deflection 612 of a protruding bar, rod, or tether segment 613 may be measured (for example, using optical, magnetic, or other sensors) to determine the corresponding angle of tether 610. In this manner, precise angle measurements may be collected without impeding range of motion or introducing unnecessary mechanical complexity.

In an alternate hardware arrangement, the use of angle sensors 621*a*-*n* enables tracking of a vertical angle of a tether 620, to detect and optionally measure vertical movement or orientation of a user's torso. When tether 620 contacts a sensor 621*a*-*n*, this may be registered and used to detect a general vertical movement (that is, whether the tether is angled up or down). For more precise measurements, the specific hardware construction of a sensor 621*a*-*n* may be varied, for example using a pressure-sensing switch to detect how much force is applied and use this measurement to determine the corresponding angle (as may be possible given a tether 620 of known construction). It should be appreciated that various combinations of hardware may be used to provide a desired method or degree of angle detection or measurement, for example using a conductive tether 620 and a capacitive sensor 621*a*-*n* to detect contact, or using a mechanical or rubber-dome switch (as are commonly used in keyboard construction) to detect physical contact without a conductive tether 620.

The use of angle detection or measurement may expand interaction possibilities to encompass more detailed and natural movements of a user's body. For example, if a user crouches, then all tethers 410*a*-*n* may detect a downward angle simultaneously. Additionally, data precision or availability may be enhanced by combining input from multiple available sensors when possible (for example, utilizing adaptive software to collect data from any sensors that it detects, without requiring specific sensor types for operation), for example by combining data from tethers 410*a*-*n* and hardware sensors such as an accelerometer or gyroscope, enabling multiple methods of achieving similar or varied types or precision levels of position or movement detection. Similarly, when a user jumps then all tethers may detect an upward angle simultaneously. However, if a user leans in one direction, it may be appreciated that not all tethers 410*a*-*n* will detect the same angle. For example, tethers 410*a*-*n* in the direction the user is leaning may detect a downward angle, while those on the opposite side would detect an upward angle (due to the orientation of the user's torso and thus a worn torso harness 420). In this manner, more precise torso interaction may be facilitated through improved detection and recognition of orientation and movement. Additionally, it may be appreciated that sensors 621*a*-*n* may be utilized for other angle measurements, such as to detect horizontal angle. For example, if a user is wearing a non-rotating torso harness 420, when they twist their body a similar stress may be applied to all attached tethers 410*a*-*n*. Without angle detection the precise nature of this movement will be vague, but with horizontal angle detection it becomes possible to recognize that all tethers 410*a*-*n* are being strained in a similar direction (for example, in a clockwise pattern when viewed from above, as a user might view tethers 410a-n during use), and therefore interpret the interaction as a twisting motion (rather than, for example, a user squatting or kneeling, which might apply a similar stress to the tethers 410a-n but would have different angle measurements).

Figure 7:
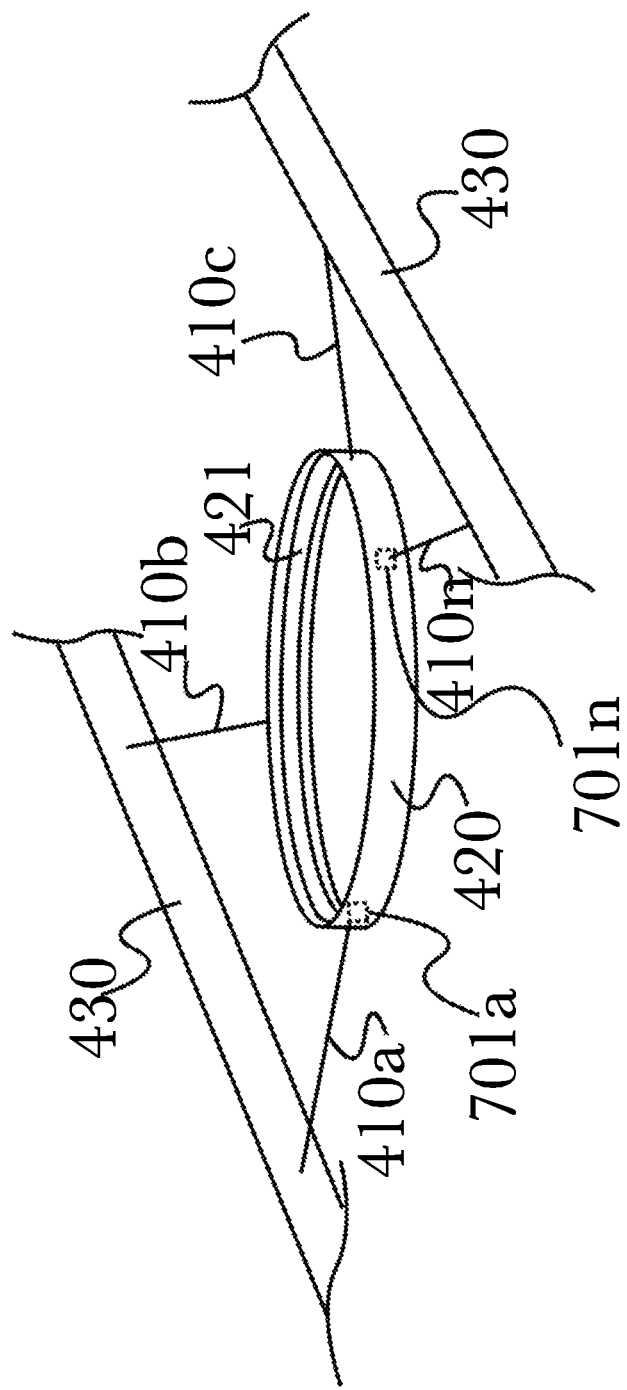
FIG. 7 is a diagram illustrating an exemplary apparatus for natural torso tracking and feedback for electronic interaction, illustrating the use of multiple tethers and a movable torso harness comprising a plurality of angle sensors positioned within the movable torso harness.

FIG. 7 is a diagram illustrating an exemplary hardware arrangement of an apparatus for natural torso tracking and feedback for electronic interaction according to a preferred embodiment of the invention, illustrating the use of multiple tethers 410a-n and a movable torso harness 420 comprising a plurality of angle sensors 701a-n positioned within the movable torso harness 420. According to the embodiment, a plurality of tethers 410a-n may be affixed or integrally-formed as part of a handle or railing 430, such as handlebars found on exercise equipment such as a treadmill, elliptical trainer, stair-climbing machine, or the like. In alternate arrangements, specifically-designed equipment with affixed or integral tethers 410a-n may be used, but it may be appreciated that a modular design with tethers 410a-n that may be affixed and removed freely may be desirable for facilitating use with a variety of fitness equipment or structural elements of a building, according to a user's particular use case or circumstance as well as weight-holding strength of the tethers. Tethers 410a-n may then be affixed or integrally-formed to angle sensors 701a-n placed within or integrally-formed as a component of torso harness 420 (as illustrated in the form of a belt) that may be worn by a user such that movement of their body affects tethers 410a-n and applies detectable or measurable stress to tethers 410a-n and angular motion to angle sensors 701a-n. In this manner, it may be appreciated that angle sensors 701a-n may be utilized as integral or removable components of a torso harness 420, as an alternative arrangement to utilizing angle sensors 701a-n placed or formed within railings 430 or other equipment components connected to distal ends of tethers 410a-n (with respect to the user's torso). According to various embodiments, sensors may be placed optionally on a belt, vest, harness, or saddle-like surface or at attachment points on safety railings, or indeed both.

Figure 9:
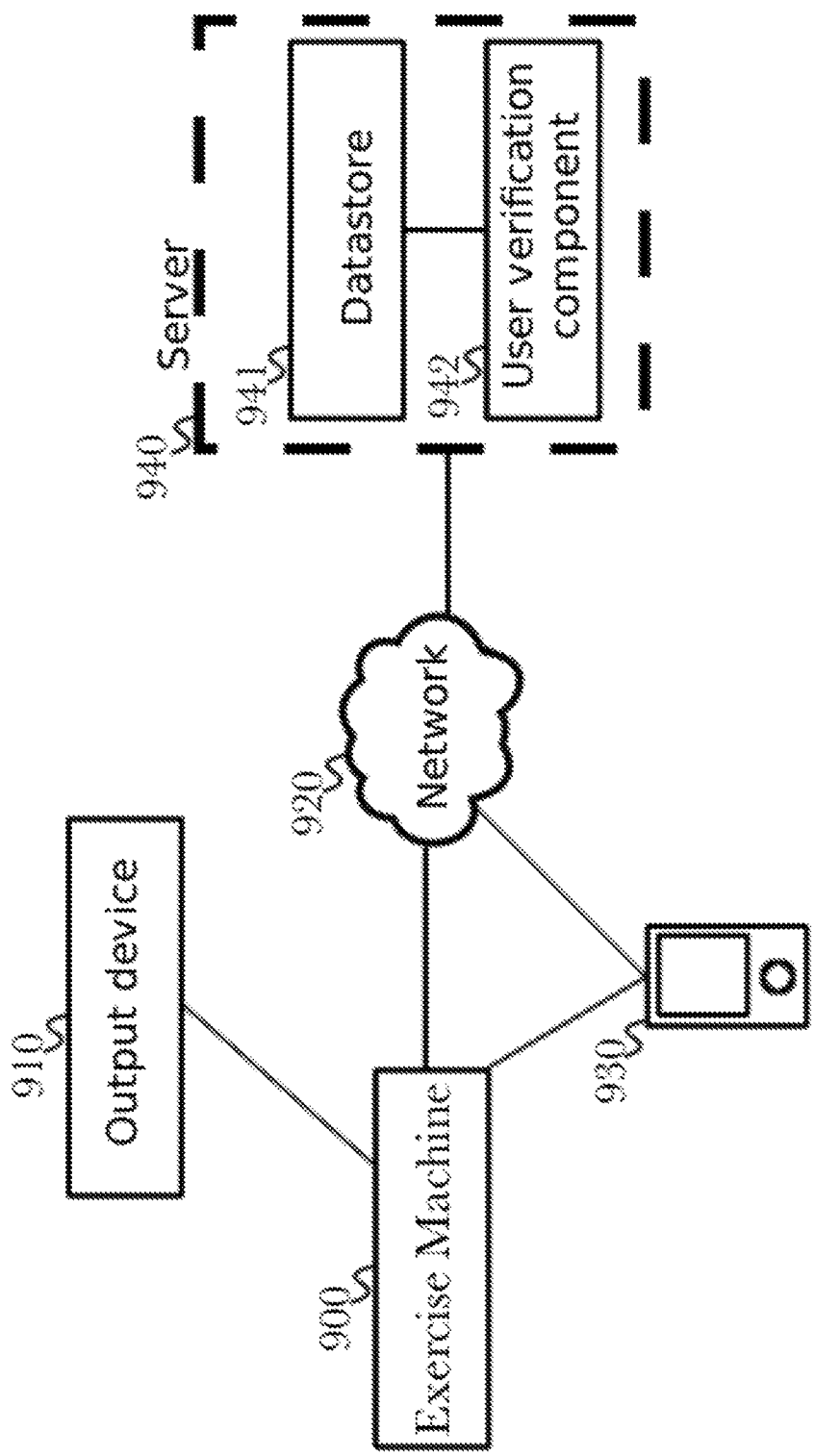
FIG. 9 is a block diagram of an exemplary system architecture for a stationary exercise bicycle being connected over local connections to a smartphone, an output device other than a phone, and a server over a network, according to an aspect.

FIG. 9 is a block diagram of an exemplary system architecture 900 of an exercise machine 100 being connected over local connections to a smartphone or computing device 930, an output device other than a phone 910, and a server over a network 940. An exercise machine 100 may connect over a network 920, which may be the Internet, a local area connection, or some other network used for digital communication between devices, to a server 940. Such connection may allow for two-way communication between a server 940 and an exercise machine 800. An exercise machine 100 may also be connected over a network 920 to a smartphone or computing device 930, or may be connected directly to a smartphone or computing device 930 either physically or wirelessly such as with Bluetooth connections. An exercise machine 100 also may be connected to an output device 910 which may display graphical output from software executed on an exercise machine 100, including Mixed or virtual reality software, and this device may be different from a smartphone or computing device 930 or in some implementations may in fact be a smartphone or computing device 930. A remote server 940 may contain a data store 941, and a user verification component 942, which may contain typical components in the art used for verifying a user's identity from a phone connection or device connection, such as device ID from a smartphone or computing device or logging in with a user's social media account.

Figure 10:
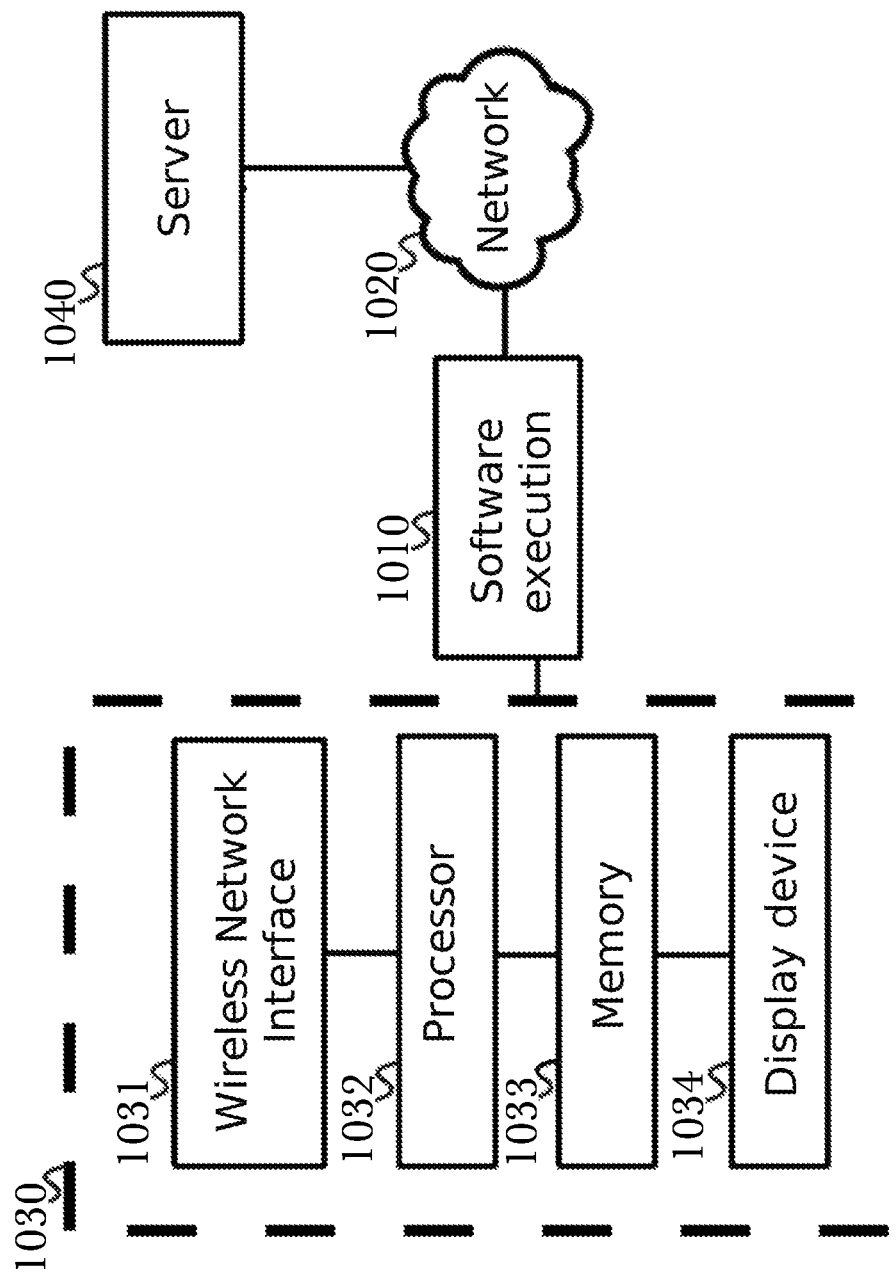
FIG. 10 is a diagram of an exemplary hardware arrangement of a smart phone or computing device running a user identification component and communicating over a network, according to an aspect.

FIG. 10 is a diagram of an exemplary hardware arrangement of a smart phone or computing device 1030 executing software 1010 and communicating over a network 1020. In an exemplary smart phone or computing device 1030, key components include a wireless network interface 1031, which may allow connection to one or a variety of wireless networks including Wi-Fi and Bluetooth; a processor 1032, which is capable of communicating with other physical hardware components in the computing device 1030 and running instructions and software as needed; system memory 1033, which stores temporary instructions or data in volatile physical memory for recall by the system processor 1032 during software execution; and a display device 1034, such as a Liquid Crystal Display (LCD) screen or similar, with which a user may visually comprehend what the computing device 1030 is doing and how to interact with it. It may or may not be a touch enabled display, and there may be more components in a computing device 1030, beyond what are crucially necessary to operate such a device at all. Software 1010 operating on a processor 1033 may include a mixed or virtual reality application, a user verification system, or other software which may communicate with a network-enabled server 1040 and exercise machine 100 software for the purposes of enhanced mixed or virtual reality.

Figure 11:
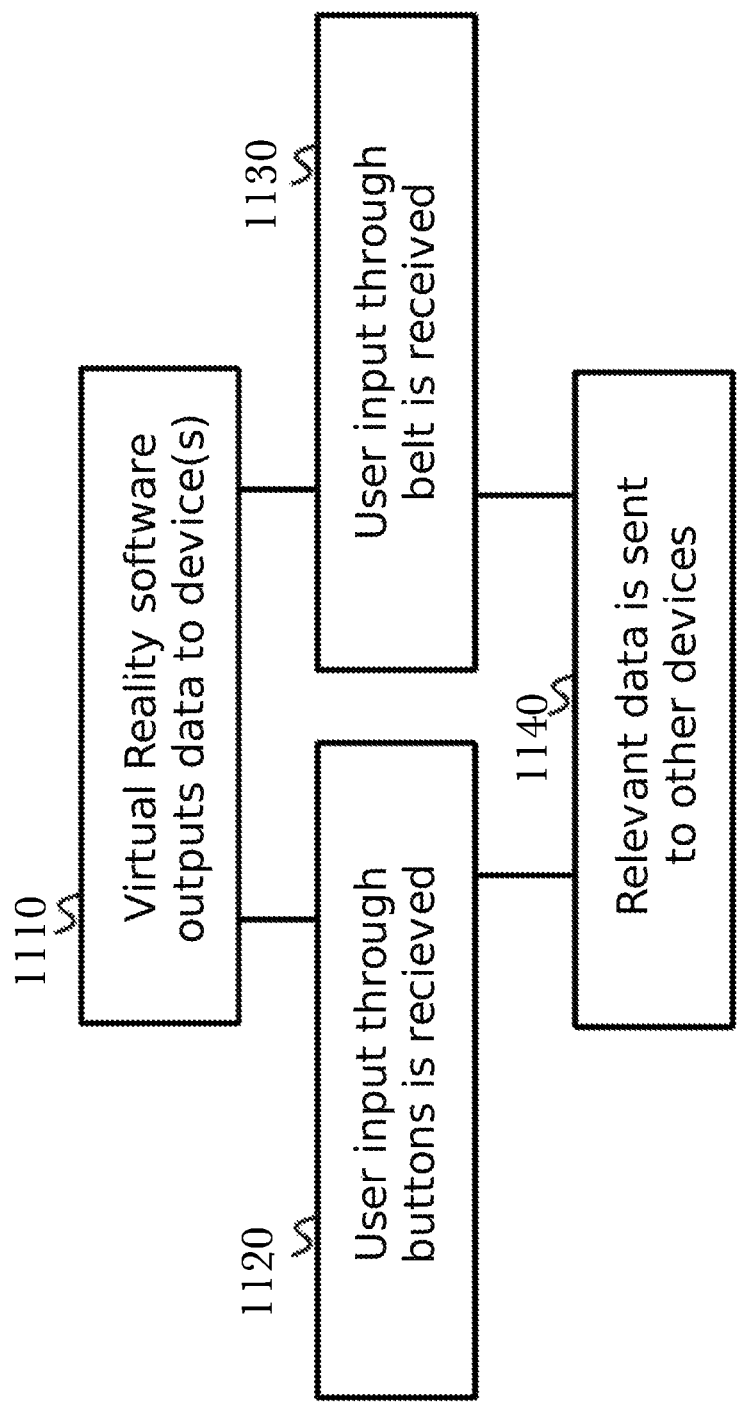
FIG. 11 is a block diagram of a method of mixed or virtual reality software operating to receive input through different sources, and send output to devices, according to an aspect.

FIG. 11 is a block diagram of a method of mixed or virtual reality software operating to receive input through different sources, and send output to devices. Mixed or virtual reality software which may be run on a phone or computing device 1030 or another device, outputs data to a visual device for the purpose of graphically showing a user what they are doing in the software 1110. Such display may be a phone display 1034, or a separate display device such as a screen built into an exercise machine 100 or connected some other way to the system, or both display devices. During software execution, user input may be received either through buttons 1130 on the exercise machine 100, 1120, or through input from a belt-like harness 420, such as user orientation or movements. Such received data may be sent 1140 to either a mobile smart phone or computing device 1030, or to a server 1040 over a network 1020, or both, for processing, storage, or both. Data may be stored on a server with a data store device 1041 and may be processed for numerous uses including user verification with a user verification component 1042. Data may be processed either by software running on an exercise machine 100, a smart phone or computing device 1030, or some other connected device which may be running mixed or virtual reality software, when input is received from a user using either buttons on an exercise machine 100, a belt-like harness 420, or both, and optionally using hardware features of an exercise machine 100 such as handlebars, pedals, or other features in mixed or virtual reality software for tasks such as representing movement in a simulation.

Figure 17:
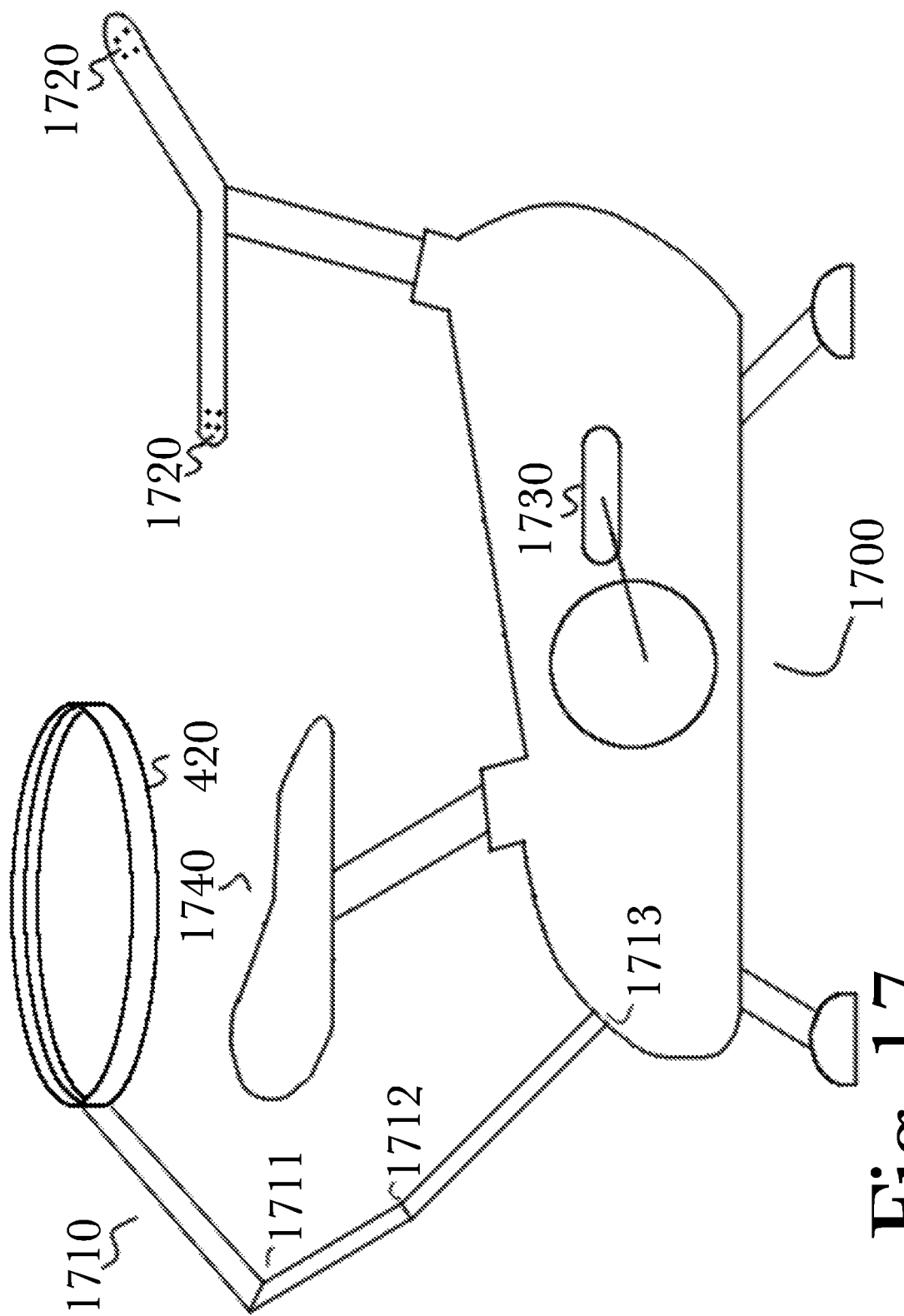
FIG. 17 is a block diagram of an exemplary virtual reality or mixed reality enhanced exercise machine, illustrating the use of a stationary bicycle with hand controls on the handles, and a belt-like harness attachment.

FIG. 17 is a block diagram of an exemplary virtual reality or mixed reality enhanced exercise machine, illustrating the use of a stationary bicycle 1700 with hand controls on the handles 1720, and a belt-like harness attachment 420. A stationary exercise bicycle device 1700, which may be of any particular design including a reclining, sitting, or even unicycle-like design, possesses two pedals 1730 as is common for stationary exercise bicycles of all designs. On handlebars of a stationary exercise bicycle may exist buttons and controls 1720 for interacting with a virtual reality or mixed reality augmented piece of software, allowing a user to press buttons in addition to or instead of pedaling, to interact with the software. A belt-like harness attachment 420 is attached via a mechanical arm 1710 to a stationary exercise bicycle 1700, which may monitor motion and movements from a user during the execution of virtual reality software. A mechanical arm 1710 may have an outer shell composed of any material, the composition of which is not claimed, but must have hinges 1711, 1712, 1713 which allow for dynamic movement in any position a user may find themselves in, and angular sensors inside of the arm at the hinge-points 1711, 1712, 1713 for measuring the movement in the joints and therefore movement of the user. A stationary bicycle device 1700 may also have a pressure sensor in a seat 1740, the sensor itself being of no particularly novel design necessarily, to measure pressure from a user and placement of said pressure, to detect movements such as leaning or sitting lop-sided rather than sitting evenly on the seat.

Figure 18:
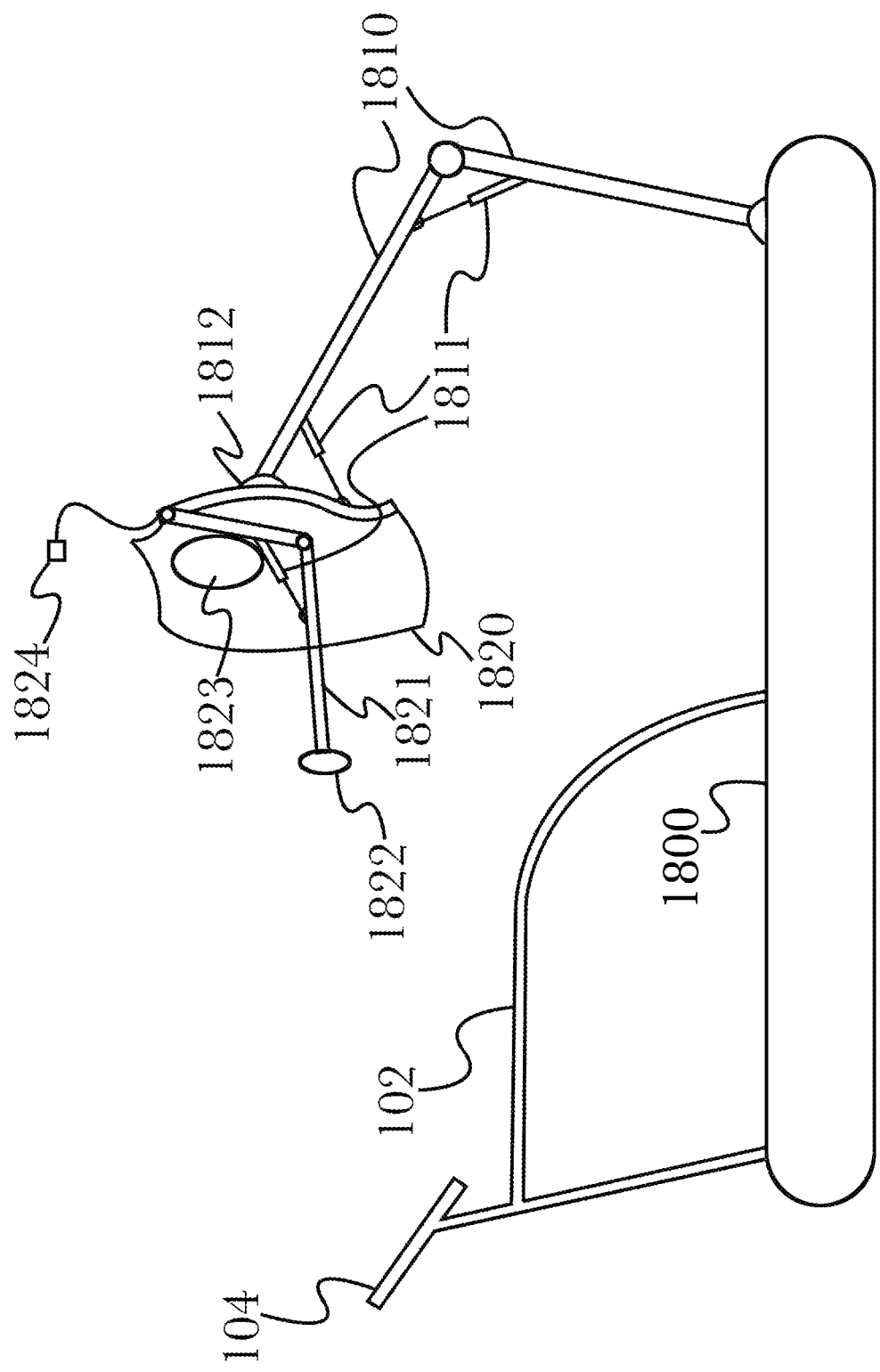
FIG. 18 is a diagram of another exemplary virtual reality or mixed reality enhanced exercise machine, illustrating the use of a treadmill exercise machine with a vest-type harness with a plurality of pistons to provide a hardware-based torso joystick with full-body tracking.

FIG. 18 is a diagram of another exemplary virtual reality or mixed reality enhanced exercise machine, illustrating the use of a treadmill exercise machine 100, 1800 a vest-type harness 1820 with a plurality of pistons 1811 to provide a hardware-based torso joystick with full-body tracking. According to this embodiment, a treadmill or other exercise machine 100, 1800 may comprise a plurality of rigid side rails 102 for a user to grip for support as needed during use (for example, as a balance aid or to assist getting on the machine and setting up other equipment properly) as well as a rigid stand or mount 104 for a user's smartphone or other computing device, that may be used to operate a virtual reality or mixed reality software application. Exercise machine 100, 1800 may further comprise a jointed arm 1810 or similar assembly that may be integrally-formed or removably affixed to or installed upon exercise machine 100, 1800. Arm 1810 may utilize a plurality of pistons 1811 to provide for movement during use in order to follow the movements of a user's body, as well as to provide tension or resistance to motion when appropriate (for example, to resist a user's movements or to provide feedback) and motion detection of a user's movement during use, according to various aspects described previously (referring to FIGS. 3-7, for example) by measuring movement of a piston 1811 or arm 1810 and optionally applying tension or resistance to piston 1811 to retard movement of arm 1810 and constrain user movement or simulate specific forms of physical feedback. For example, if a user is moving an avatar in a virtual reality software application, when the avatar encounters an obstacle such as another avatar, object, or part of the environment, resistance may be applied to piston 1811 to prevent the user from moving further, so that their avatar is effectively prevented from moving through the obstacle and thereby facilitating the immersive experience of a solid object in a virtual environment. Additional arms may be used for a user's limbs 1921 and may incorporate straps 1922 to be affix about a user's arm, wrist, or other body part, to incorporate more detailed movement tracking of a user's arms and/or legs rather than just torso-based tracking. A vest-type harness 1920 may be used in place of a belt 420, to allow for more natural movement or to provide greater area upon which to affix additional arms 1821, pistons 1811, or any of a variety of sensors, for example such as accelerometers 1822 or gyroscopes 1823 for detecting body orientation (not all optional sensors are shown for the sake of clarity). For example, a vest 1820 may have integrated feedback actuators 1812 for use in first-person software applications to simulate impacts or recoil, or it may incorporate heating or cooling elements to simulate different virtual environments while worn. Additionally, vest 1820 may incorporate electrical connectors 1824 for various peripheral devices such as controllers 305*a-b* or a headset 302, reducing the risk of tangles or injury by keeping cables short and close to the user so they cannot cause issues during movement or exercise.

Figure 19:
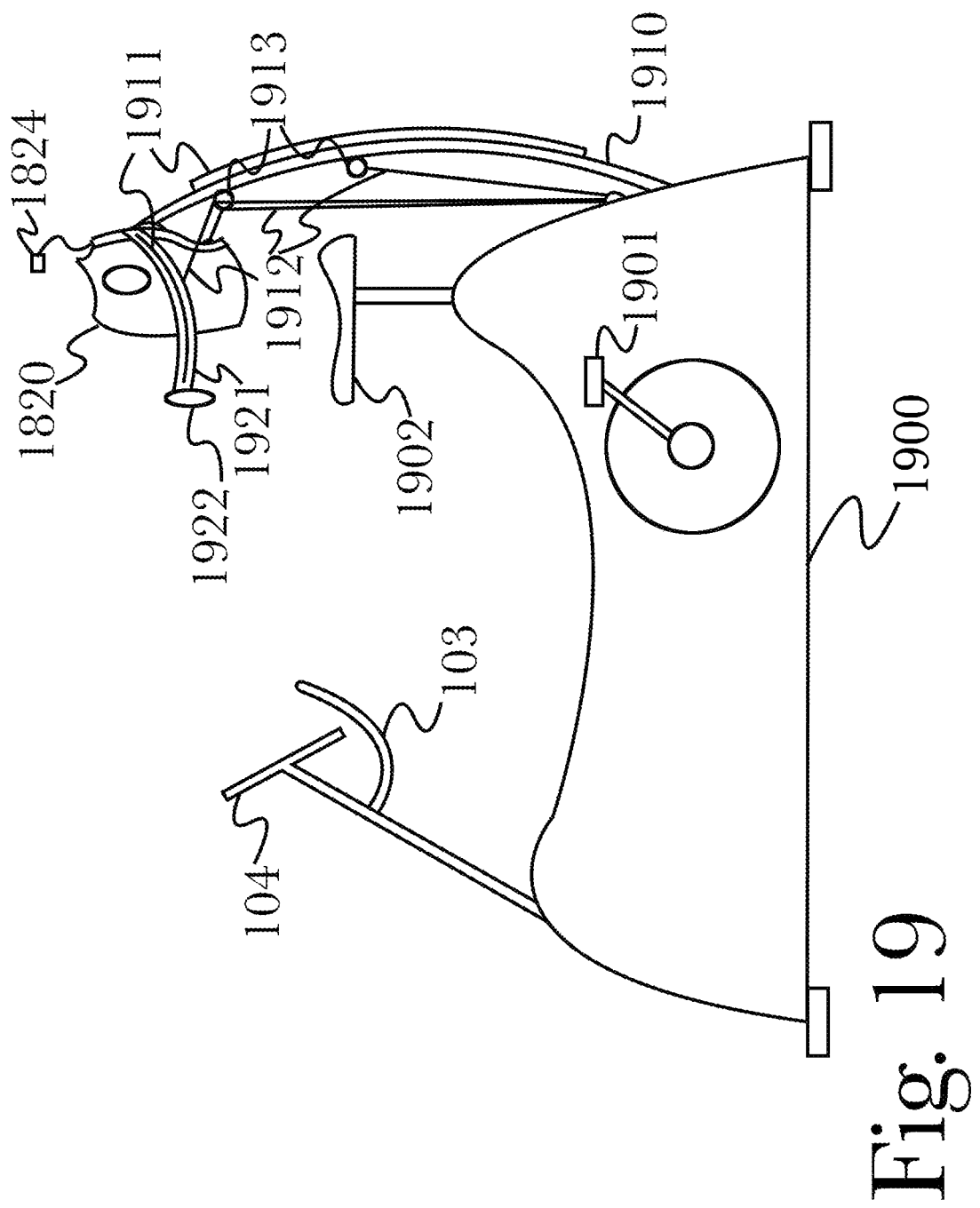
FIG. 19 is a diagram of another exemplary virtual reality or mixed reality enhanced exercise machine, illustrating the use of a stationary bicycle with a vest-type harness with a plurality of strain sensors and tethers.

FIG. 19 is a diagram of another exemplary virtual reality or mixed reality enhanced exercise machine, illustrating the use of a stationary bicycle This present application is a continuation-in-part of Ser. No. 16/176,511, titled "VIRTUAL REALITY AND MIXED REALITY ENHANCED EXERCISE MACHINE", and filed on Oct. 31, 2018, which with a vest-type harness 1820 with a plurality of strain sensors 1911 and tethers 1912, according to an aspect of the invention. According to this embodiment, rather than a jointed arm 1810 and pistons 1811, a solid flexible arm 1910 may be used to detect user movement while positioned on a seat 1902 to use exercise machine 100, for example while the user is seated to use pedals 1901 on a stationary bike or elliptical training machine. Through a plurality of strain gauges 1911 that detect the flexion or extension of the solid arm. Tethers 1912 may be used for either movement tracking or providing feedback to a user, or both, and may optionally be connected or routed through joints or interconnects 1913 to allow for a greater variety of attachment options as well more precise feedback (for example, by enabling multiple angles from which a tether 1912 may apply force, to precisely simulate different effects). Additional arms may be used for a user's limbs 1921 and may incorporate straps 1922 to be affix about a user's arm, wrist, or other body part, to incorporate more detailed movement tracking of a user's arms and/or legs rather than just torso-based tracking. Additional arms 1921 may also incorporate additional tethers 1912 and strain sensors 1911 to track movement and apply feedback to specific body parts during use, further increasing precision and user immersion. A vest-type harness 1820 may be used in place of a belt 420, to allow for more natural movement or to provide greater area upon which to affix additional arms 1921, tether 1912, or any of a variety of sensors, for example such as accelerometers or gyroscopes for detecting body orientation (not all optional sensors are shown for the sake of clarity). For example, a vest 1820 may have integrated feedback actuators for use in first-person software applications to simulate impacts or recoil, or it may incorporate heating or cooling elements to simulate different virtual environments while worn. Additionally, vest 1820 may incorporate electrical connectors 1914 for various peripheral devices such as controllers 305*a-b* or a headset 302, reducing the risk of tangles or injury by keeping cables short and close to the user so they cannot cause issues during movement or exercise.

Figure 20:
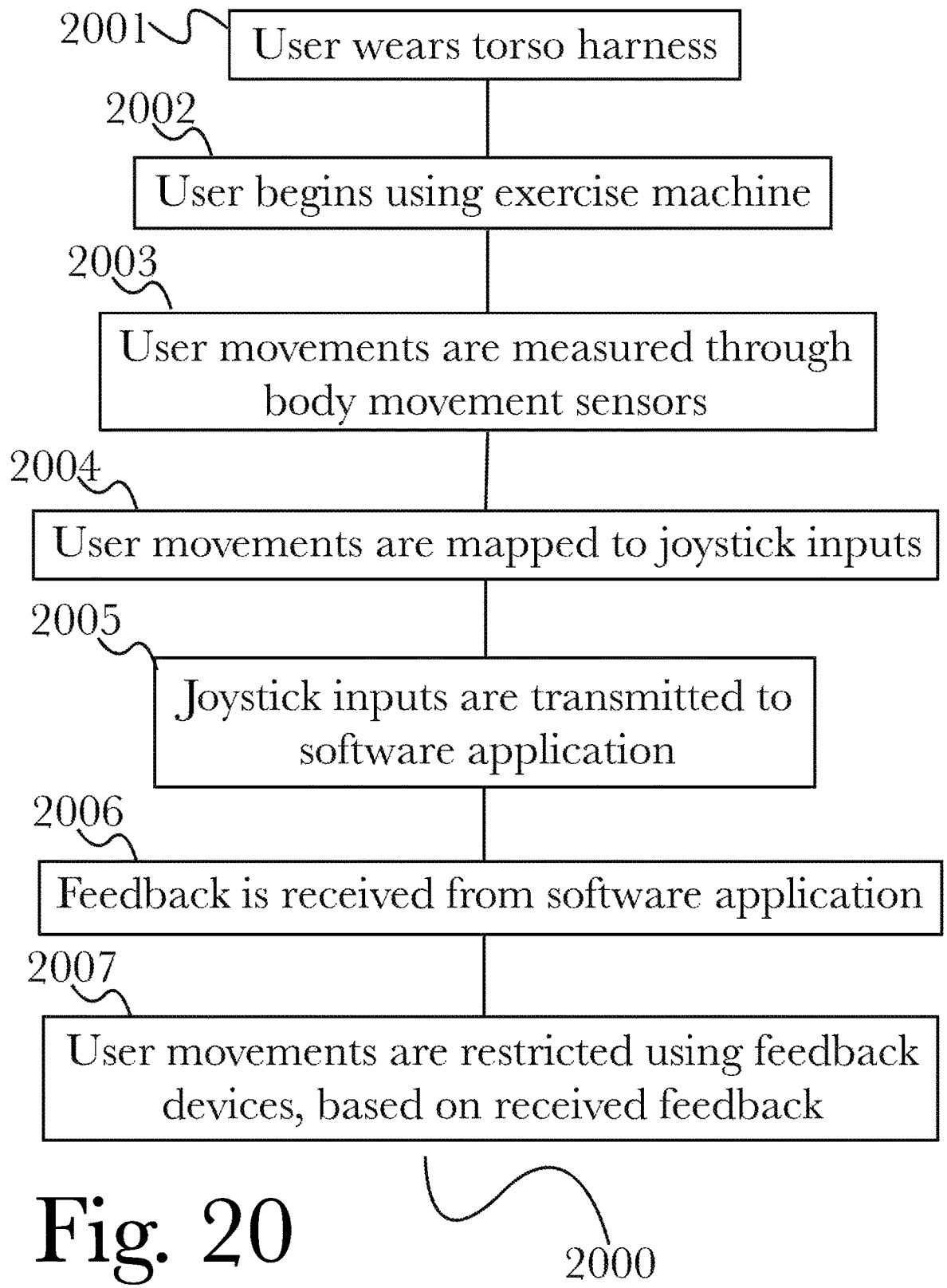
FIG. 20 is a flow diagram illustrating an exemplary method for operating a virtual and mixed-reality enhanced exercise machine.

FIG. 20 is a flow diagram illustrating an exemplary method 2000 for operating a virtual and mixed-reality enhanced exercise machine, according to one aspect. According to the aspect, a user may wear 2001 a torso harness such as a belt 420 or vest 1820 harness, while they engage in the use 2002 of an exercise machine 100. While using the exercise machine 100, the user's movements may be detected and measured 2003 through the use of a plurality of body movement sensors such as (for example, including but not limited to) strain sensors 1911, tethers 410*a-c*, 1912, pistons 1811, or optical sensors 1201*a-n*. These measured user movements may then be mapped by a composition server 801 to correspond to a plurality of movement inputs of a virtual joystick device 2004. These virtual joystick inputs may then be transmitted 2005 to a software application, for example a virtual reality or mixed reality application operating on a user device such as (for example, including but not limited to) a smartphone 930, personal computing device, or headset 302. Composition server 801 may then receive feedback from the software application 2006, and may direct the operation of a plurality of feedback devices such as tethers 410*a-c*, 1912 or pistons 1811 to resist or direct the user's movement 2007 to provide physical feedback to the user based on the received software feedback.

Figure 21:
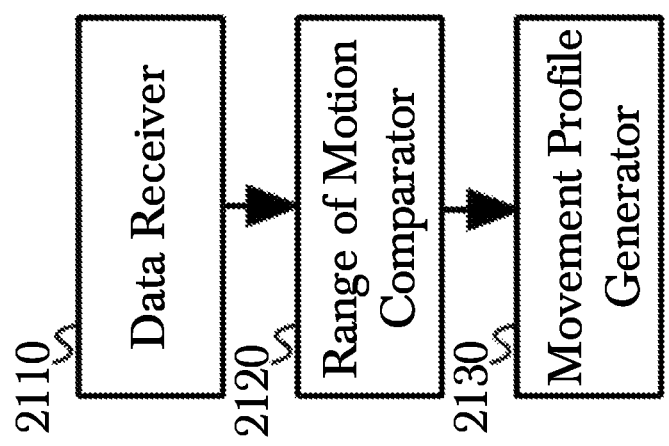
FIG. 21 is a system diagram of a key components in the analysis of a user's range of motion and balance training.

FIG. 21 is a system diagram of a key components in the analysis of a user's range of motion and balance training. A datastore containing statistical data 2110 on a user's age category, gender, and other demographic data, as well as a datastore containing balancing algorithms 2120, are connected to a collection of components integrated into an exercise system 2130, including a plurality of sensors 2131, a movement profile analyzer 2132, a balance trainer 2133, and a tuner 2134. A plurality of sensors 2131 may be connected to varying parts of an exercise system, tethered to a user, or otherwise connected to or able to sense a user during exercise, and may inform a movement profile analyzer 2132 of the performance of a user's exercise during such exercise. A movement profile analyzer 2132 may use data from a datastore containing statistical data on a user 2110 to generate movement profile of how a user performs and moves during exercise, in comparison with how they may be expected to move, and pass this data on to a balance trainer 2133 which is further connected to a datastore containing balance algorithms 2120. A balance trainer 2133 accesses and utilizes balance algorithms 2120 in conjunction with assembled movement profile data 2132 and determines if a user is in need of correcting their form or balance during exercise. A tuner 2134 is connected to a datastore containing user profile data 2150 and also connected to a balance tuner 2133, enabling a user's individual preferences or specifications, or exercise needs, to inform adjustments for a balance trainer 2133, for example if a user would initially be detected as stumbling by a balance trainer 2133 but the user were to specify that they are not falling, and continue to exercise in this fashion for whatever reason (such as physical limitations), a tuner 2134 may adjust the balance trainer 2133 in this instance. Such information is stored in a user's profile data 2150. A display 2140 is connected to core components 2130 and may display the warnings generated by a balance trainer 2133 or offer a user the opportunity to offer adjustments or physical information to a tuner 2134 for adjusting a balance trainer 2133.

Figure 22:
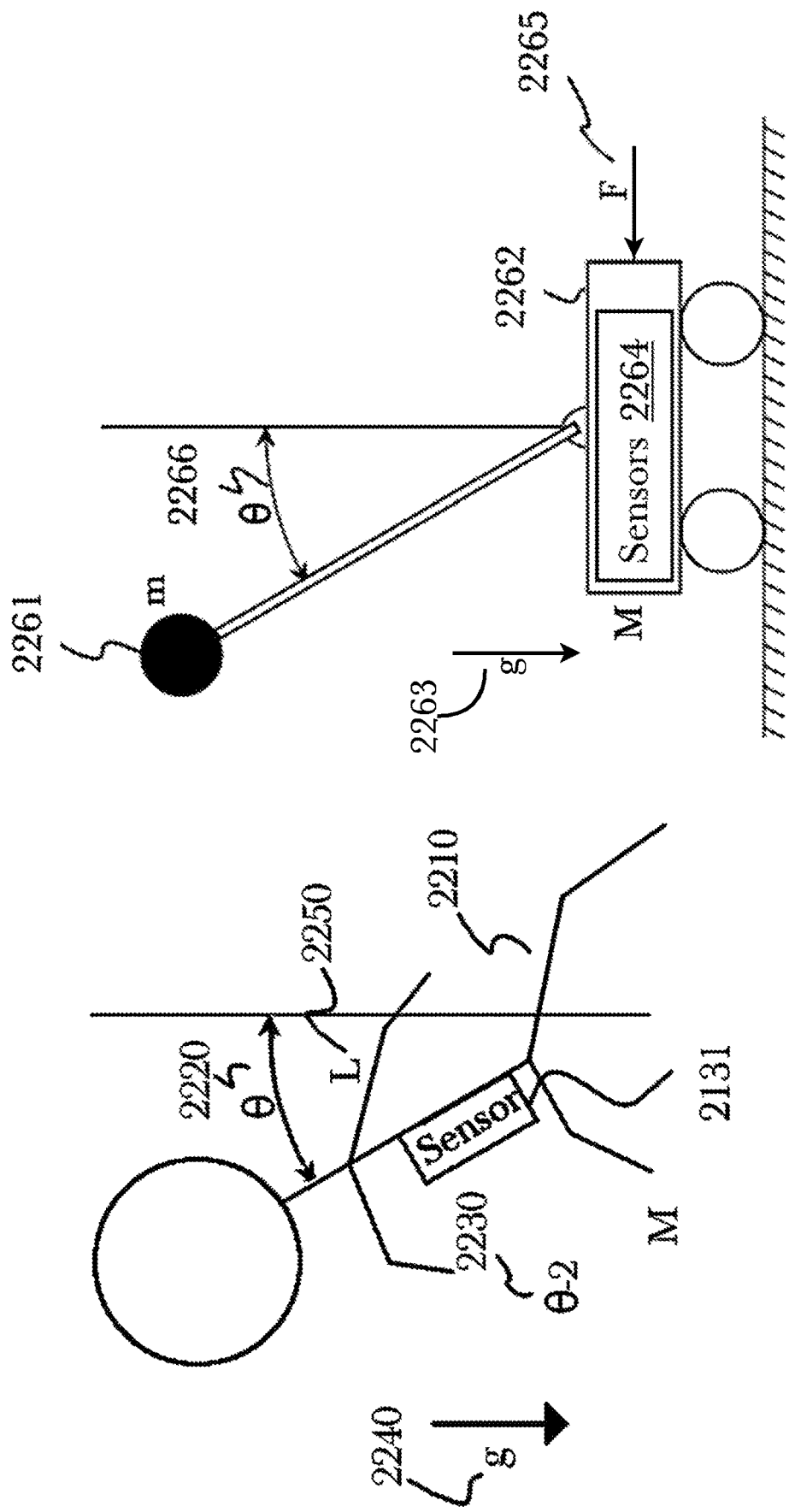
FIG. 22 is a diagram showing a system for balance measurement and fall detection.

FIG. 22 is a diagram showing a system for balance measurement and fall detection. A classic problem in control system theory is controlling an inverted pendulum such that it balances vertically without falling down. On the right side of the diagram is a drawing of the inverted pendulum problem in which a pendulum (a rod having some length, l, and some mass, m) 2261 is attached to a movable platform 2262. Sensors 2264 on the platform 2262 detect at least the angle, θ, 2266 of the pendulum 2261 from vertical, and may also be configured to detect or calculate the rate of change of the angle 2266, the acceleration of the platform 2262, and other variables. As the pendulum 2261 falls away from vertical due to the force of gravity, g, 2263, a control mechanism such as a proportional, integral, differential (PID) controller may calculate and apply a force F 2265 to the platform 2262 sufficient to swing the pendulum 2261 back to vertical against the force of gravity 2262.

A similar system may be used to measure balance and detect and predict falls by a person with impaired balance abilities. A user 2210 may wear a sensor and electronics package 2131 on the torso. The sensor and electronics package 2131 may be simply a collection of sensors (e.g. accelerometers, gyroscopes, etc.) configured to transmit data to an external computing device, or the sensor and electronics package 2131 may itself have a computing device. The user's body mass, m, can be entered manually or obtained from a wireless scale capable of communicating wirelessly with the sensor and electronics package 2131. As the user's torso moves from the vertical position 2220, the angle from vertical and rate of change of the angle, θ″, 2230 from vertical can be measured, tracked, and used to make predictions about the likelihood of a fall. Angular momentum 2230 may be represented by θ″ 2230, a user's angle deviation from vertical being represented by θ 2220, the force of gravity being represented by g 2240, and the approximate height of a user's body-part acting similar to the bar of an inverted pendulum being represented by L 2250. The data obtained from the sensors and electronics package 2131 may be used in conjunction with various algorithms (e.g. a PID controller) and the user's historical or manually-entered movement ability to determine when the rate of fall is likely to exceed the user's ability to accelerate toward the direction of fall fast enough to right the torso. It is therefore possible to analyze and characterize a user's motions that may lead to a stumble or fall.

Figure 23:
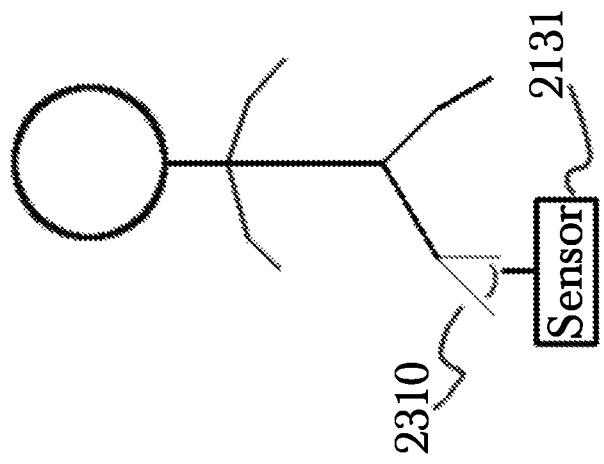
FIG. 23 is a system diagram of a sensor measuring the range of motion of a user during a specific exercise.

FIG. 23 is a system diagram of a sensor measuring the range of motion of a user during a specific exercise. A user performing an exercise with their leg is shown, with a sensor 2131 and angular movement 2310. A sensor 2131 may be used to characterize the angle of the user's motion, or be attached as an ankle weight for a more specific implementation (but by no means the only implementation of this process of using a sensor to measure an individual user's body parts during exercise), to achieve more information about user form in addition to or instead of using an inverted pendulum 2220 with a sensor 2131 inside.

Figure 24:
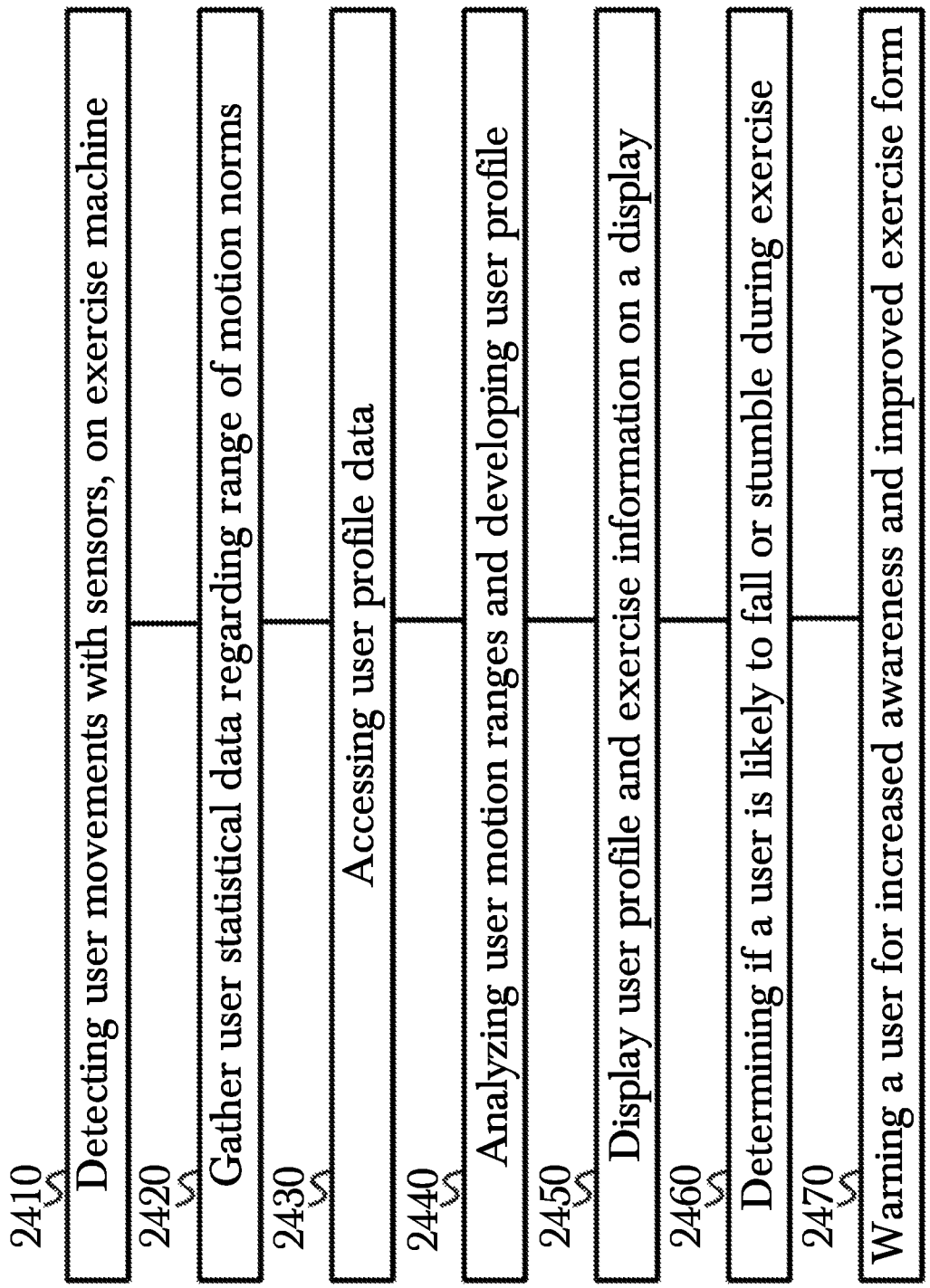
FIG. 24 is a method diagram illustrating behavior and performance of key components for range of motion analysis and balance training.

FIG. 24 is a method diagram illustrating behavior and performance of key components for range of motion analysis and balance training. A user's movements may first be detected on or with an exercise machine, using a plurality of sensors 2131, 2410. Given a user's movements 2410, statistical data on a user's demographics may be gathered 2420 using a datastore containing such information 2110, to compare a user's movements with expected or anticipated norms based on acquired or default statistical data. A user's profile data 2150 may then be accessed 2430, and using a user's profile data 2150 which may contain individual preferences or information beyond statistical norms 2110 or sensor-acquired exercise data 2131, analyses of a user's range of motion may occur 2440. Such analyses may include examining differences between a user's expected motion during an exercise, with their actual motion, measuring individual, anomalous movements during a user's exercise (such as a single motion that does not match with the rest of the user's movements), and other techniques to analyze anomalies in a user's displayed exercise ability. A user's profile is also generated from these analyses 2440, allowing a history of a user's exercise performance to be recorded for future analysis and for comparison with future observed exercise patterns and performance. A user's profile and exercise performance, along with any other notes, may be displayed 2450 with a graphical or textual display 2140, allowing a user to see for themselves their performance and deficiencies as determined by the system. A further step may be to detect if a user is detect to be likely to fall or stumble 2460, such as if a leg movement is not proper for a running motion on a treadmill, and display or sound a warning to a user 2470 using a display 2140 or any other method that may be available to the physical activity data capture device for warning a user of possible injury or failure. These warnings may further be recorded in a user profile 2150 for access by a tuner 2134 and balance trainer 2133 to help the user be aware of patterns of exercise performance that may lead to similar incidents in the future, before they happen, thereby helping to ensure safety of physically at-risk exercise machine users.

Figure 31:
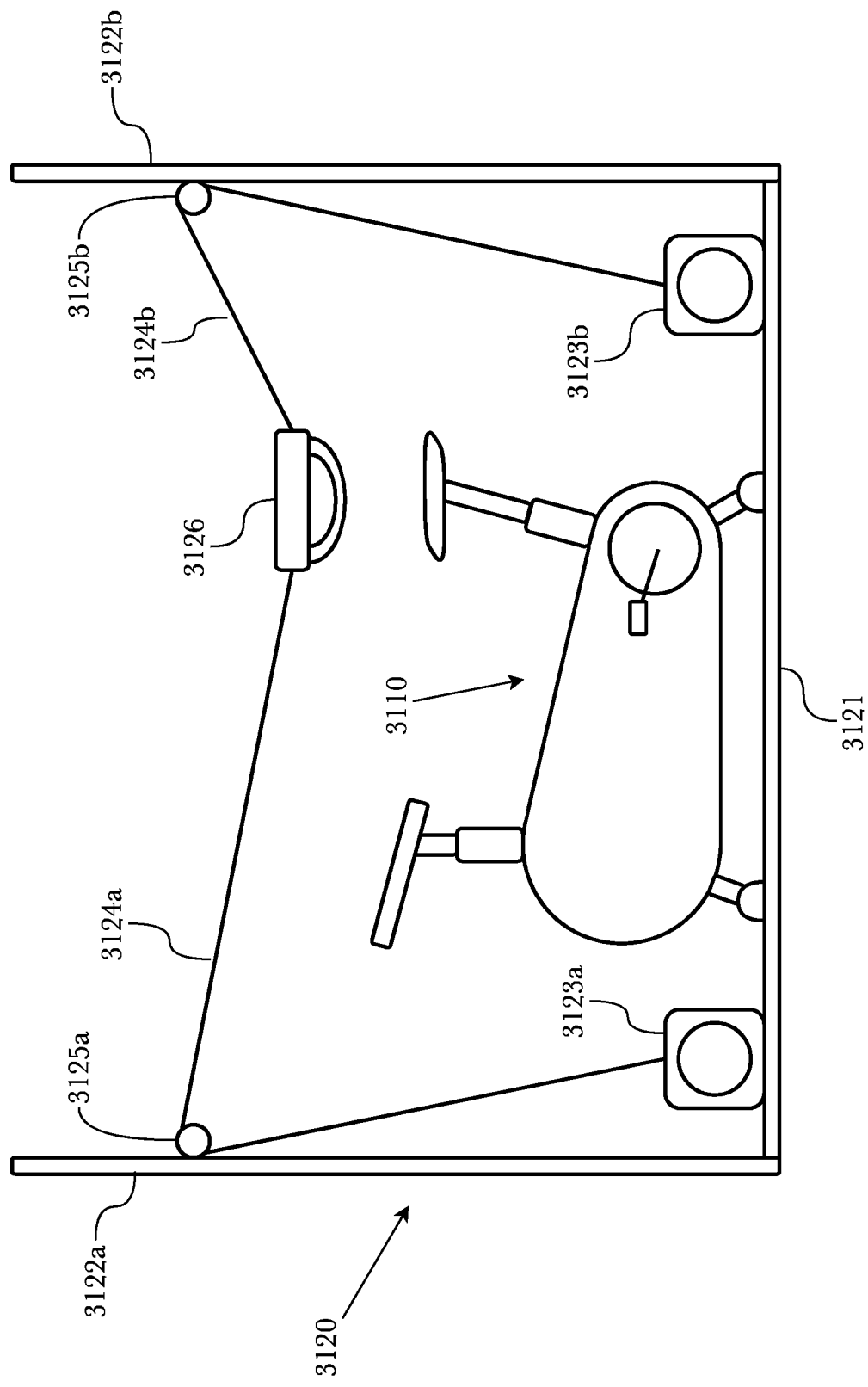
FIG. 31 is an exemplary human/machine interface and support system for using body movements to interface with computers while engaging in exercise.

FIG. 31 is an exemplary human/machine interface and support system for using body movements to interface with embedded or external computers while engaging in exercise. In this embodiment, an exercise machine 3110 is placed inside a frame 3120 which contains components for sensing the movement of an individual, providing haptic feedback, and providing support in case of a fall. In this embodiment, the exercise machine 3110 is depicted as a stationary bicycle, although any type of exercise machine 3110 (e.g., treadmill, stair-stepper, rowing machine, weight-lifting machines, etc.) may be used. The exercise machine 3110 may contain or be in communication with an embedded or external computer that communicates with other components of the system, although in some embodiments, the exercise machine 3110 is not communicatively coupled with other components. In some embodiments, no exercise machine 3110 at all is used, and the individual may freely engage in exercise or other physical movement such as running in place, jumping, dancing, lifting barbells or free weights, etc. The frame 3120 comprises a base 3121 and one or more vertical supports 3122a,b. Mounted to a point on the vertical supports are one or more pulleys or routing devices 3125a,b, which guide one or more tethers 3124a,b at a height above the waist level of the individual during exercise. The tethers 3124a,b are attached at one end to a belt, harness, vest, or other device 3126 attachable to the body of the individual, and at the other end to sensors/actuators 3123a,b. In this embodiment, the sensors/actuators 3126a,b are electric motors fitted with rotary encoders and the tethers 3124a,b are wound around a drum on the shaft of the motors. In this way, body movements of the individual may be sensed and recorded as rotational movements of the drum, and rotational movement data may be sent to a computing device which can perform calculations to determine position, distance of movement, speed of movement, acceleration, and other such calculations. For example, the linear distance of movement may be calculated from the number of rotations and the circumference of the drum. Linear speed may be calculated as the linear distance over time. The position of the individual may be calculated from speed and distance. The rotational movement, linear distance, linear speed, or other calculations may be used to control the computing device or the output from a computing device such as a game, virtual reality environment, etc. Further, the motors of the sensors/actuators 3123a,b may also act as actuators, and varying voltages and currents may be applied to the motors to provide haptic feedback to the individual, such as resistance to movement, jerking, or vibration. This haptic feedback may be provided in response to interactions with the computer, such as to indicate game events, interactions with the virtual reality environment, etc. In one aspect, the belt 3126, tethers 3124a,b, and sensors/actuators 3123a,b, may be used to support the individual in case of a slip or fall. Such support may be provided passively (e.g., a fixed resistance provided by the motors), actively (e.g., by sensing an acceleration and applying a resistance to the tethers), or by mechanical means (e.g., seatbelt-type mechanical locking mechanism that locks the tether upon a sudden pull). Other embodiments may use additional vertical supports 3122a,b, tethers, 3124a,b, and sensors/actuators 3123a,b. For example, some embodiments may have vertical supports 3122a,b and associated equipment at the front and back, and at the left and right sides of the individual. Many other configurations are possible.

Figure 32:
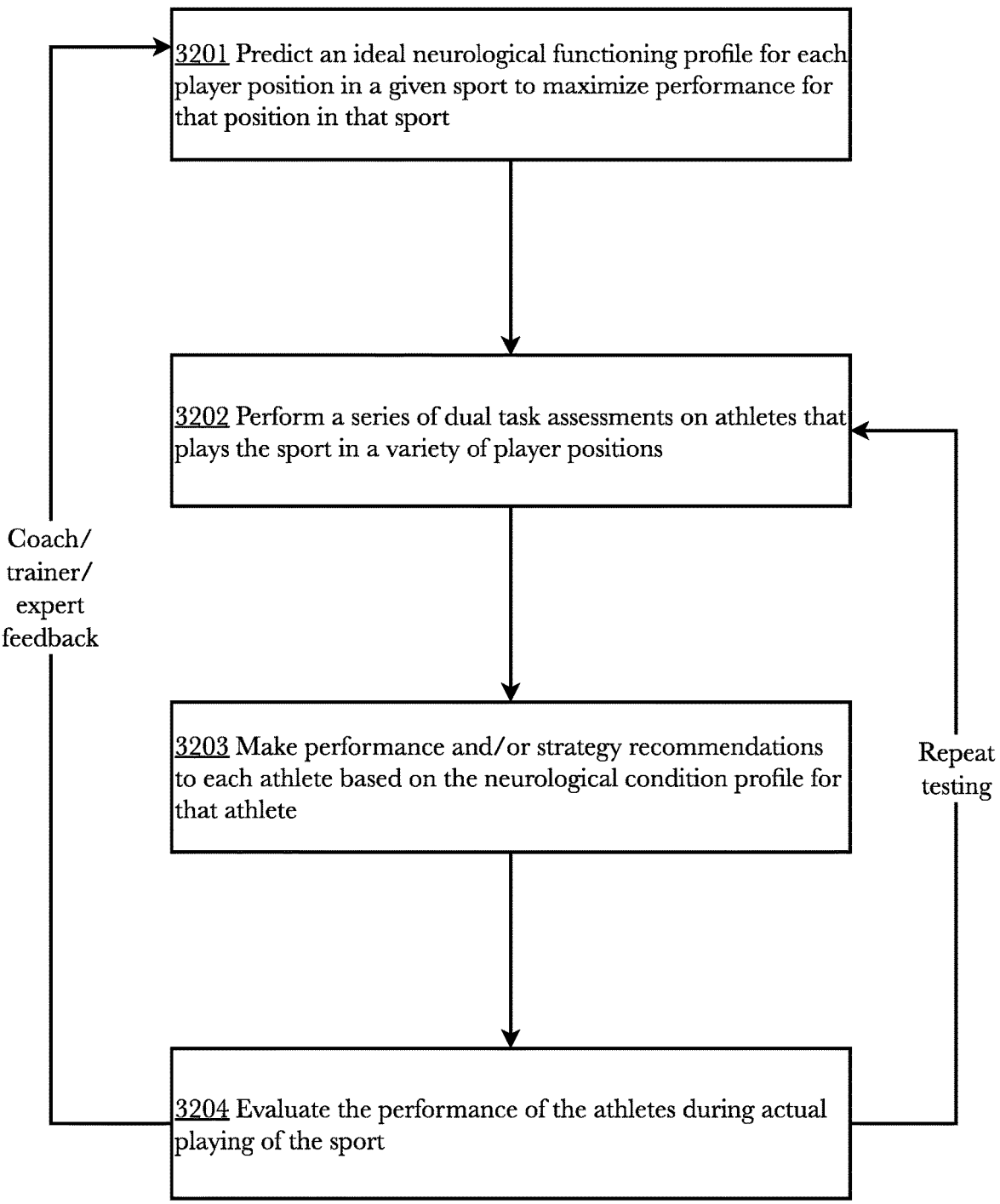
FIG. 32 is an exemplary method for application of the system to improve the performance of a sports team.

FIG. 32 is an exemplary method for application of the system to improve the performance of a sports team. In a first step, an ideal neurological functioning profile for each player position in a given sport is predicted by experts in the sport (e.g., coaches, trainers, athletes, sports bettors, etc.) for maximization of performance for that position in that sport 3201. Then, dual task assessments are performed for athletes from a variety of positions that play the sport 3202. Based on the neurological condition profile generated by the testing, performance and/or play strategy recommendations are made for performance improvements for that player for that position 3203. Performance of the athletes during actual play is evaluated by the experts in the sport 3204. The evaluation feedback from the experts is provided back to step 3201, and athletes are retested at step 3202. All of these steps may be performed repeatedly to continuously refine input and recommendations. In some embodiments, dual task assessments at step 3202 may be specifically selected to condition or train the aspects of neurological functioning determined to be ideal at step 3201 (i.e., step 3202 a can be both a conditioning/training step and an evaluation step).

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Figure 13:
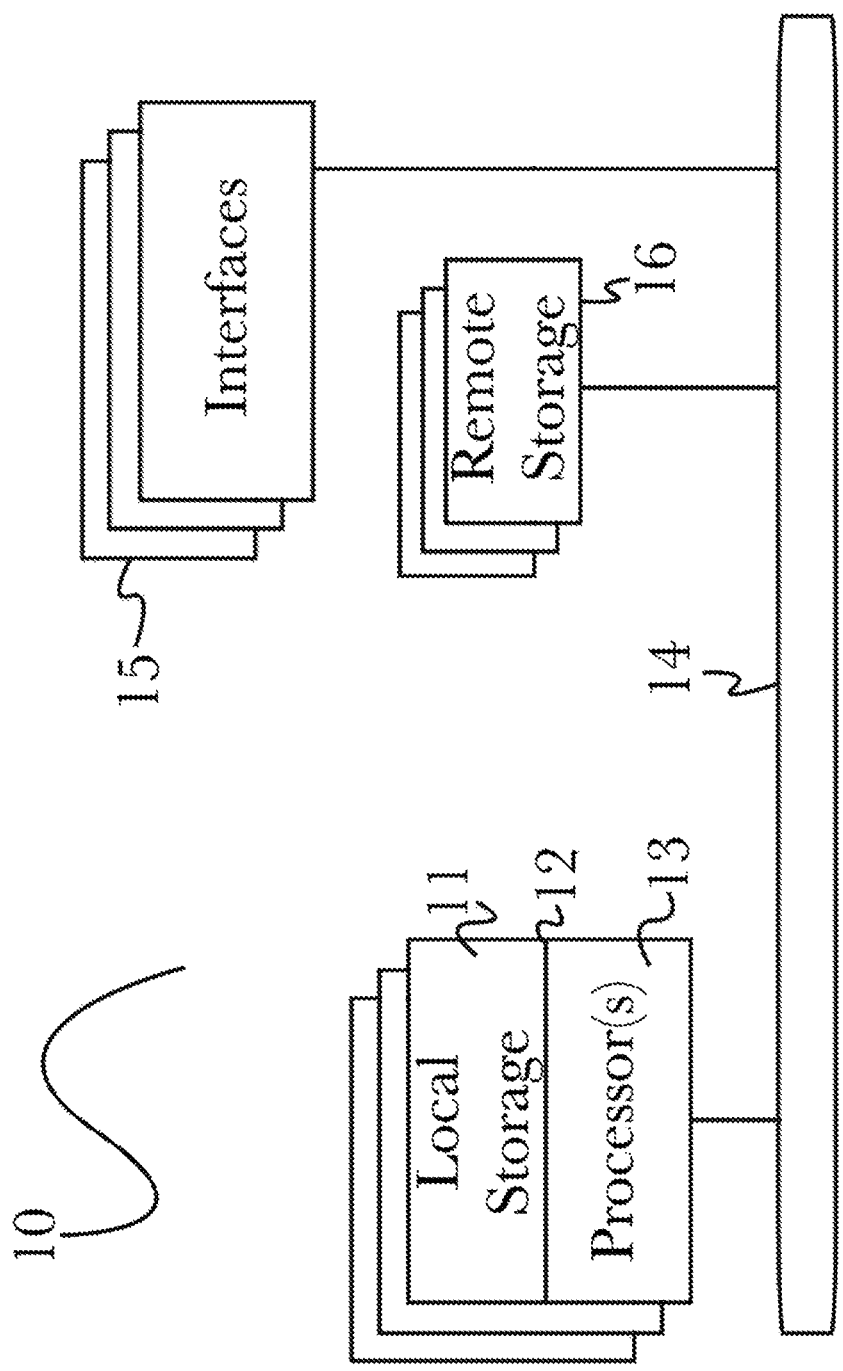
FIG. 13 is a block diagram illustrating an exemplary hardware architecture of a computing device.

Referring now to FIG. 13, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one embodiment, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one embodiment, a computing device 10 may be configured or designed to function as a server system utilizing CPU 12, local memory 11 and/or remote memory 16, and interface(s) 15. In at least one embodiment, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a specific embodiment, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one embodiment, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 13 illustrates one specific architecture for a computing device 10 for implementing one or more of the inventions described herein, it is by no means the only device architecture on which at least a portion of the features and techniques described herein may be implemented. For example, architectures having one or any number of processors 13 may be used, and such processors 13 may be present in a single device or distributed among any number of devices. In one embodiment, a single processor 13 handles communications as well as routing computations, while in other embodiments a separate dedicated communications processor may be provided. In various embodiments, different types of features or functionalities may be implemented in a system according to the invention that includes a client device (such as a tablet device or smartphone running client software) and server systems (such as a server system described in more detail below).

Regardless of network device configuration, the system of the present invention may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 14:
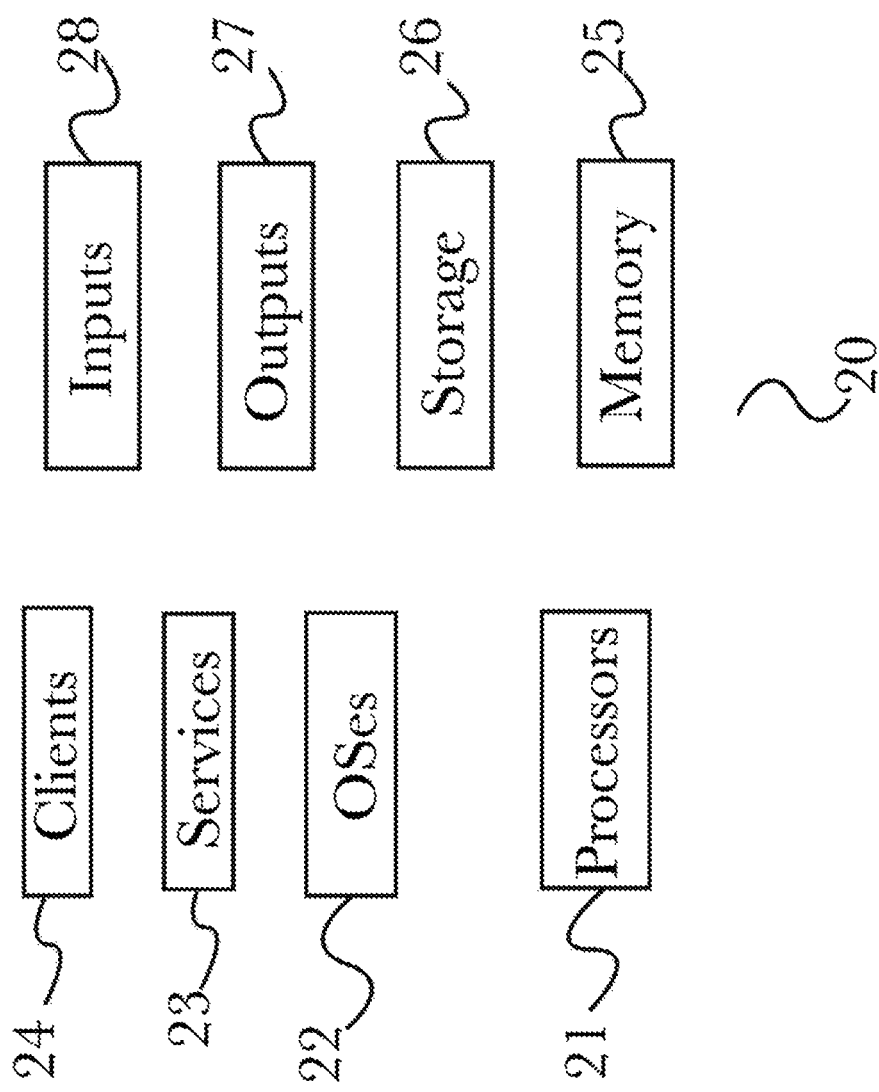
FIG. 14 is a block diagram illustrating an exemplary logical architecture for a client device.

In some embodiments, systems according to the present invention may be implemented on a standalone computing system. Referring now to FIG. 14, there is shown a block diagram depicting a typical exemplary architecture of one or more embodiments or components thereof on a standalone computing system. Computing device 20 includes processors 21 that may run software that carry out one or more functions or applications of embodiments of the invention, such as for example a client application 24. Processors 21 may carry out computing instructions under control of an operating system 22 such as, for example, a version of MICROSOFT WINDOWS™ operating system, APPLE MACOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 13). Examples of storage devices 26 include flash memory, magnetic hard drive, CD-ROM, and/or the like.

Figure 15:
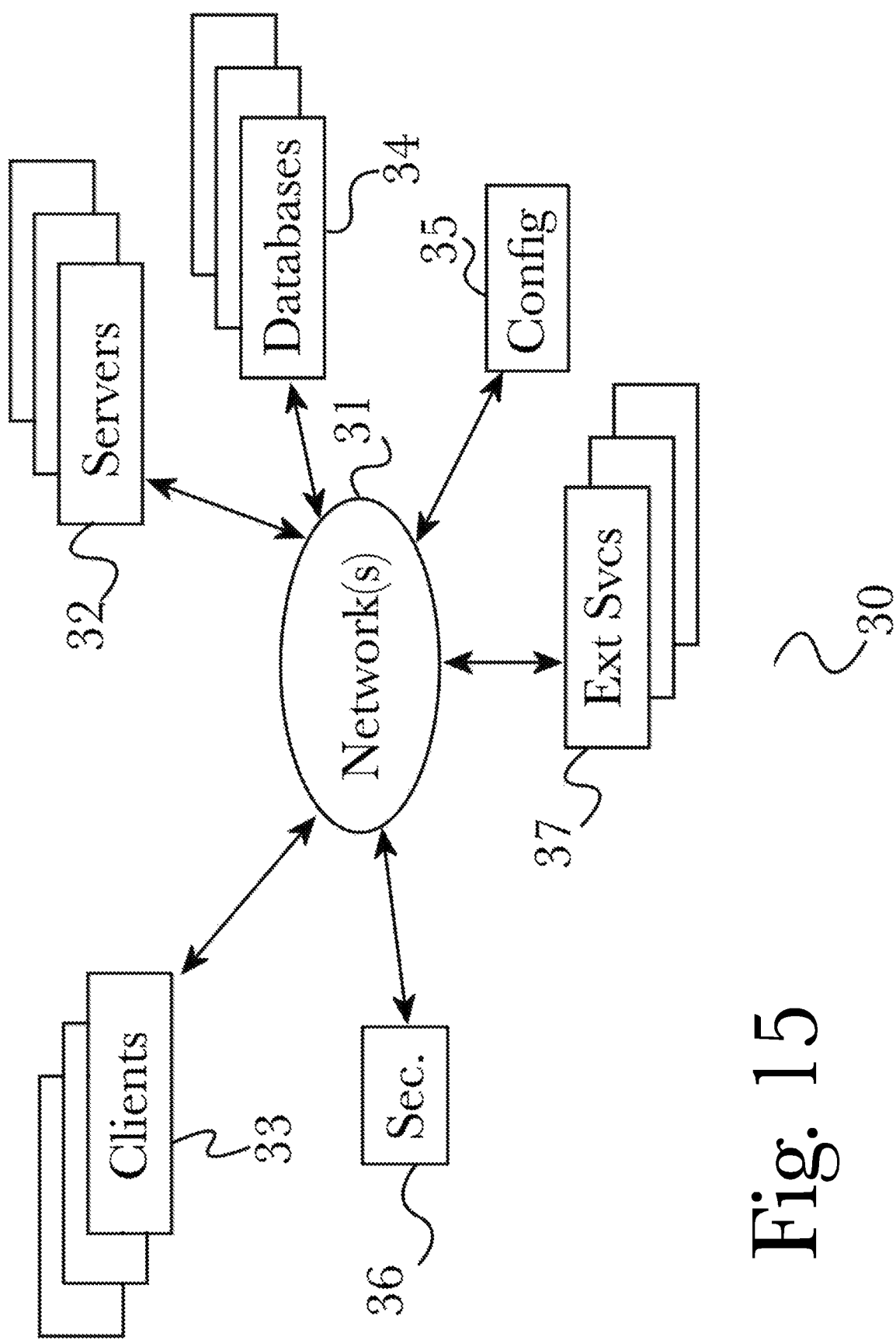
FIG. 15 is a block diagram showing an exemplary architectural arrangement of clients, servers, and external services.

In some embodiments, systems of the present invention may be implemented on a distributed computing network, such as one having any number of clients and/or servers. Referring now to FIG. 15, there is shown a block diagram depicting an exemplary architecture 30 for implementing at least a portion of a system according to an embodiment of the invention on a distributed computing network. According to the embodiment, any number of clients 33 may be provided. Each client 33 may run software for implementing client-side portions of the present invention; clients may comprise a system 20 such as that illustrated in FIG. 14. In addition, any number of servers 32 may be provided for handling requests received from one or more clients 33.

Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the invention does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in an embodiment where client applications 24 are implemented on a smartphone or other electronic device, client applications 24 may obtain information stored in a server system 32 in the cloud or on an external service 37 deployed on one or more of a particular enterprise's or user's premises.

In some embodiments of the invention, clients 33 or servers 32 (or both) may make use of one or more specialized services or appliances that may be deployed locally or remotely across one or more networks 31. For example, one or more databases 34 may be used or referred to by one or more embodiments of the invention. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the invention. It will be appreciated by one having ordinary skill in the art that any combination of known or future database technologies may be used as appropriate, unless a specific database technology or a specific arrangement of components is specified for a particular embodiment herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, most embodiments of the invention may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments of the invention without limitation, unless a specific security 36 or configuration system 35 or approach is specifically required by the description of any specific embodiment.

Figure 16:
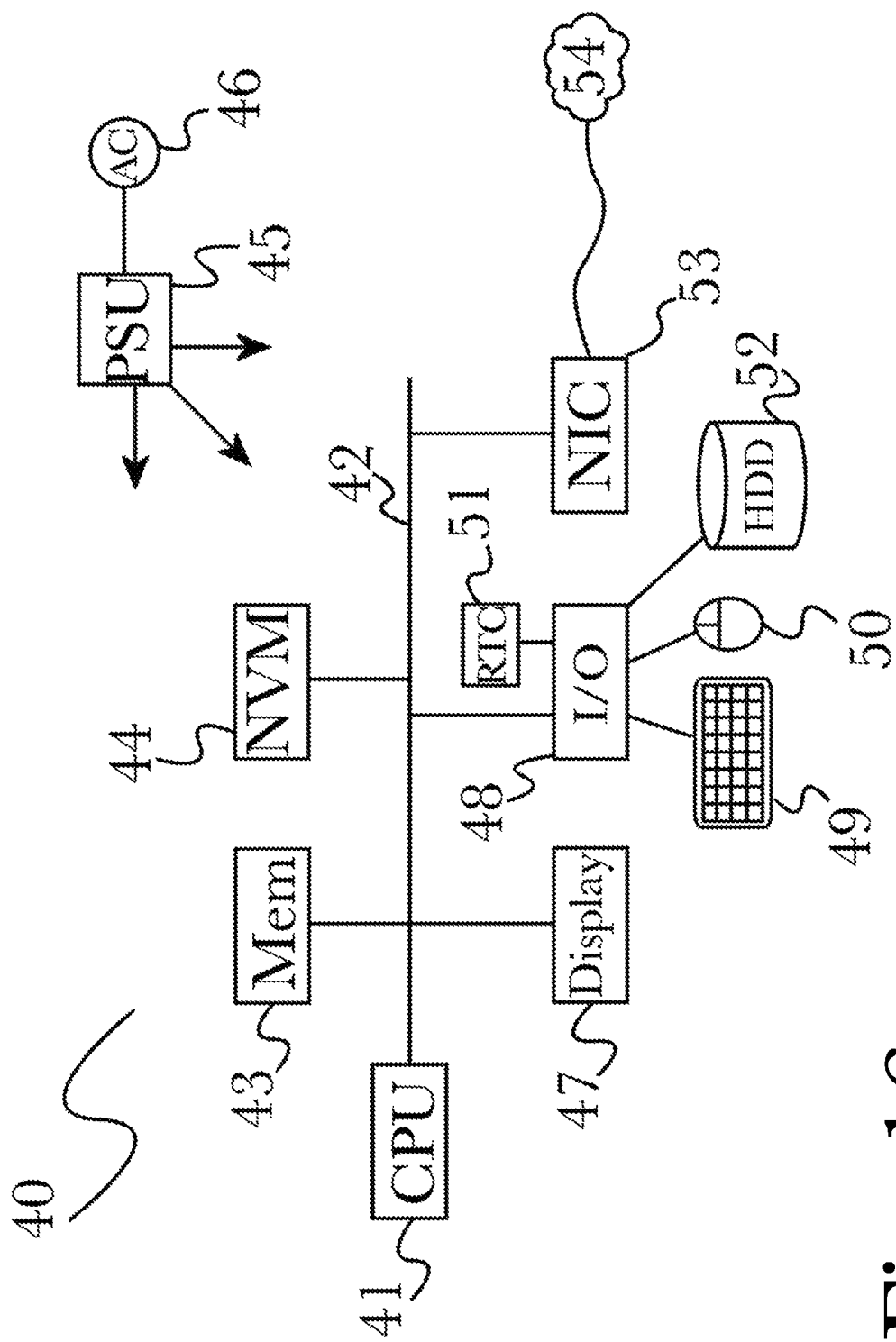
FIG. 16 is another block diagram illustrating an exemplary hardware architecture of a computing device.

FIG. 16 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of the present invention may be distributed among any number of client and/or server components. For example, various software modules may be implemented for performing various functions in connection with the present invention, and such modules may be variously implemented to run on server and/or client components.

The skilled person will be aware of a range of possible modifications of the various embodiments described above. Accordingly, the present invention is defined by the claims and their equivalents.

What is claimed is:

1. A system for detection of neurological functioning and conditions, comprising:
   a physical activity data capture device, configured to capture movement data and other biometric data of an individual during performance of a primary task;
   a software application, comprising a first plurality of programming instructions stored in a memory of, and operating on a processor of, a computing device, wherein the first plurality of programming instructions, when operating on the processor, cause the computing device to:
   assign a primary task to an individual under assessment;
   while the individual engages in the primary task, record movement data on the primary activity and other biometric data of the individual, using the physical activity data capture device;
   assign an associative activity to the individual which corresponds to a specific neurological function or region;
   while the individual engages in the associative activity, record performance data of the individual on the associative activity;
   assign a dual task to the individual, the dual task comprising simultaneous performance of the primary task and the associative activity;
   while the individual engages in the dual task, record movement data and other biometric data of the individual while performing the primary task, using the physical activity data capture device, and record performance data of the individual on the associative activity; and
   send the recorded data to a neurological functioning analyzer; and
   the neurological functioning analyzer, comprising a second plurality of programming instructions stored in the memory of, and operating on the processor of, the computing device, wherein the second plurality of programming instructions, when operating on the processor, cause the computing device to:
   receive the recorded movement data, other biometric data, and performance data;
   calculate a composite functioning score for the recorded movement data, other biometric data, and performance data, the composite functioning score comprising an indication of the level of functionality of an aspect of the individuals' nervous system; and
   generate a neurological condition profile of the individual comprising an indication of relative functioning of the aspect of the individual's nervous system.

2. The system of claim 1, wherein one or more primary tasks and one or more associative activities are assigned to the individual, a plurality of composite functioning scores are calculated comprising indications of the level of functionality of a plurality of aspects of the individuals' nervous system, and the neurological functioning profile comprises indications of relative functioning of the plurality of aspects of the individual's nervous system.

3. The system of claim 2, wherein the neurological functioning analyzer creates a composite functioning score spatial map based on the neurological functioning profile.

4. The system of claim 1, wherein the composite functioning score is compared to a history of composite functioning scores for the individual to determine changes in the composite functioning score over time.

5. The system of claim 1, wherein the composite functioning score is compared to statistical composite functioning score data for a larger population to determine the individual's relative position in the larger population with respect to the composite functioning score.

6. The system of claim 1, wherein the primary task is continuous exercise.

7. The system of claim 1, wherein the primary task is discontinuous, interval-based, or variable effort exercise.

8. The system of claim 1, wherein the associative activity involves overcoming a computer or video game-like challenge or a computer simulation of a life-like scenario or challenge.

9. The system of claim 1, wherein the recorded data is stored as a historical record of the individual's performance on primary tasks, associative activities, and dual tasks.

10. The system of claim 9, wherein the system selects the primary task and associative task based on changes to the individual's neurological condition profile over time that suggest improvements in the individual's performance.

* * * * *